(12) United States Patent
Heckel et al.

(10) Patent No.: US 6,300,342 B1
(45) Date of Patent: Oct. 9, 2001

(54) ANTITHROMBOTIC PHENYLALKYL DERIVATIVES

(75) Inventors: Armin Heckel; Rainer Soyka; Wolfgang Grell; Eric Haaksma, all of Biberach; Klaus Binder, Wiesbaden; Rainer Zimmerman, Mittelbiberach, all of (DE)

(73) Assignee: Boehringer Ingelheim Pharm KG, Ingelheim (DE)

( * ) Notice: Subject to any disclaimer, the term of this patent is extended or adjusted under 35 U.S.C. 154(b) by 0 days.

(21) Appl. No.: 09/457,961

(22) Filed: Dec. 9, 1999

Related U.S. Application Data

(63) Continuation of application No. PCT/EP98/03800, filed on Jun. 22, 1998.

(30) Foreign Application Priority Data

Jun. 26, 1997 (DE) .............................. 197 27 117

(51) Int. Cl.[7] .................. A61K 31/47; A61K 31/395; A61K 31/4709; C07D 215/36; C07D 215/38; A61P 7/02
(52) U.S. Cl. .................. 514/311; 514/314; 514/224.2; 514/230.5; 514/230.8; 514/249; 514/235.2; 514/307; 514/309; 514/637; 544/51; 544/52; 544/105; 544/353; 544/354; 544/128; 546/165; 546/141; 546/146; 546/148; 564/244
(58) Field of Search .......................... 546/165; 514/311, 514/314, 224.2, 230.5, 230.8, 249, 235.2; 544/51, 52, 105, 353, 354

(56) References Cited

U.S. PATENT DOCUMENTS 5,373,019  12/1994  Zilch et al. .

FOREIGN PATENT DOCUMENTS 43 06 506   9/1994  (DE) .
657166   *   6/1995  (EP) .

OTHER PUBLICATIONS

Chemical Abstracts, vol. 129, No. 5, Aug. 3, 1998; Columbus, Ohio, US; Abstract No. 5429w, Ito Kiyotaka et al: "Preparation of carbamoylindolines as 5–hydroxytryptamine antagonists", XP002081134, siehe Zusammenfassung & JP 98 158241 A (Fujisawa).

* cited by examiner

*Primary Examiner*—Evelyn Mei Huang
(74) *Attorney, Agent, or Firm*—R. P. Raymond; T. X. Witkowski; A. R. Stempel

(57) ABSTRACT

Antithrombotic phenylalkyl derivatives of the formula

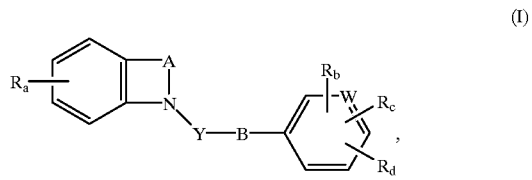

(I)

Exemplary compounds are:
(a) 1-[3-(4-amidino-phenyl)propionyl]-6-(4-fluoro-phenylsulphonamido)-1,2,3,4-tetrahydro-quinoline,
(b) 1-[3-(4-amidino-phenyl)propionyl]-6-butylsulphonamido-1,2,3,4-tetrahydro-quinoline,
(c) 1-[3-(4-amidino-phenyl)propionyl]-5-phenylsulphonamido-1,2,3,4-tetrahydro-quinoline,
(d) 1-[3-(4-amidino-phenyl)propionyl]-3-methyl-6-phenylsulphonamido-1,2,3,4-tetrahydro-quinoline, and,
(e) 1-[3-(4-amidino-phenyl)propionyl]-6-(5-chloro-thien-2-ylsulphonamido)-1,2,3,4-tetrahydro-quinoline.

10 Claims, No Drawings

ANTITHROMBOTIC PHENYLALKYL DERIVATIVES

RELATED APPLICATIONS

This application is a continuation of International Application PCT/EP 98/03800 (WO 99/00371), filed on Jun. 22, 1998.

FIELD OF THE INVENTION

The present invention relates to phenylalkyl derivatives, their use as pharmaceuticals, especially as antithrombotic agents, and methods for preparing such compounds.

DESCRIPTION OF THE INVENTION

The present invention relates to phenylalkyl derivatives of general formula

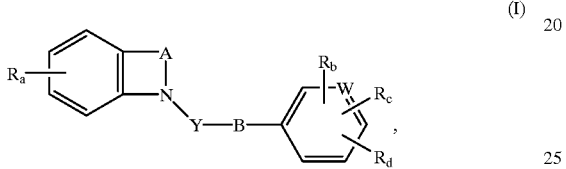

(I)

the tautomers, the stereoisomers and mixtures thereof and the salts thereof, particularly the physiologically acceptable salts thereof with inorganic or organic acid or bases, which have valuable properties.

The compounds of the above general formula I, wherein $R_b$ denotes a hydrogen atom, a nitro or cyano group, are valuable intermediate products for producing the other compounds of general formula I, and the compounds of the above general formula I, wherein $R_b$ denotes one of the optionally substituted aminomethyl or amidino groups mentioned below, and the tautomers and stereoisomers thereof have valuable pharmacological properties, particularly a thrombin-inhibiting activity, the effect of prolonging the thrombin time and an inhibitory effect on thrombocyte aggregation.

Thus, the present application relates to the new compounds of the above general formula I and the preparation thereof, pharmaceutical compositions containing the pharmacologically active compounds and their use.

In the above general formula I $R_a$ denotes a hydrogen atom, a carboxy, $C_{1-3}$-alkoxycarbonyl, benzoyl, phenylsulphonyl, nitro, $R_1NR_2$, $R_1NR_2$—X— or $(R_3X)NR_1$— group wherein $R_1$ denotes a hydrogen atom, a $C_{1-5}$-alkyl group, which may be substituted by a phenyl, carboxy, $C_{1-4}$-alkoxycarbonyl or aminocarbonyl group, whilst the amino group of the aminocarbonyl group may additionally be mono- or disubstituted by $C_{1-4}$-alkyl, phenyl-$C_{1-3}$-alkyl, phenyl, carboxy-$C_{1-3}$-alkyl- or $C_{1-3}$-alkoxycarbonyl-$C_{1-3}$-alkyl groups and the substituents may be identical or different, or a straight-chained $C_{2-3}$-alkyl group, which is terminally substituted by amino, $C_{1-3}$-alkylamino, di-($C_{1-3}$-alkyl)amino, $C_{1-4}$-alkanoylamino, phenylamino, N-benzyloxycarbonyl-phenylamino, pyrrolidino, piperidino or morpholino group, $R_2$ denotes a hydrogen atom, a $C_{1-3}$-alkyl group optionally substituted by one or two phenyl groups or by a naphthyl group, or a phenyl group which may be substituted by a fluorine, chlorine or bromine atom or by a straight-chained $C_{2-3}$-alkyl group, which is terminally substituted by an amino, $C_{1-3}$-alkylamino, $C_{1-3}$-alkanoylamino, di-($C_{1-3}$-alkyl)amino, pyrrolidino, piperidino or morpholino group, $R_1$ and $R_2$ together with the nitrogen atom between them denote a pyrrolidino or piperidino group optionally substituted by a $C_{1-3}$-alkyl, carboxy or $C_{1-3}$-alkoxycarbonyl group, a pyrrolidino or piperidino group substituted by two $C_{1-3}$-alkyl groups or a morpholino group, $R_3$ denotes a straight-chained or branched $C_{1-7}$-alkyl group, which may be substituted in the 1, 2 or 3 position by a phenyl group or in the 2 to 7 position by a fluorine, chlorine or bromine atom, by a carboxy or $C_{1-3}$-alkoxycarbonyl group, a trifluoromethyl group, a phenyl, naphthyl or chromanyl group which may be substituted in each case by a fluorine, chlorine or bromine atom, by a trifluoromethyl, $C_{1-3}$-alkyl, $C_{1-3}$-alkoxy, amino, $C_{1-3}$-alkylamino, di-($C_{1-3}$-alkyl)amino or aminocarbonyl group, whilst the abovementioned phenyl, naphthyl or chromanyl groups may additionally be substituted by one to three methyl groups, a phenyl or aminophenyl group substituted by two chlorine or bromine atoms, a thienyl group optionally substituted by a chlorine or bromine atom or by a methyl group, a $C_{3-8}$-cycloalkyl, $C_{8-12}$-bicycloalkanone, quinolyl, isoquinolyl or benzimidazolyl group or $R_1$ and $R_3$ together denote an n-alkylene group with 3 to 5 carbon atoms, wherein an ethylene group linked to the $SO_2$— or CO— group may be replaced by a 1,2-phenylene group, and X denotes a carbonyl or sulphonyl group, or $R_a$ may also denote a $C_{2-3}$-alkanoyl group, which is substituted in the alkyl moiety by a carboxy-$C_{1-3}$-alkyl or $C_{1-3}$-alkoxycarbonyl-$C_{1-3}$-alkyl group and a benzoyl, naphthoyl, phenylsulphonyl or naphthylsulphonyl group, $R_b$ denotes an amidino group optionally substituted by a $C_{1-10}$-alkoxycarbonyl or phenyl-$C_{1-3}$-alkoxycarbonyl group, a cyano or aminomethyl group, $R_c$ and $R_d$, which may be identical or different, each denote a hydrogen, fluorine, chlorine, bromine or iodine atom, a methyl, methoxy, nitro, amino or aminocarbonyl group or an amino group optionally substituted by a straight-chained $C_{2-4}$-alkanoyl group, wherein the alkanoyl moiety may be terminally substituted by a carboxy or $C_{1-3}$-alkoxycarbonyl group, A denotes an ethylene, ethenylene, n-propylene or n-butylene group optionally substituted by one or two $C_{1-3}$-alkyl groups, whilst a methylene group of an ethylene or n-propylene group optionally substituted by one or two $C_{1-3}$-alkyl groups, which is (i) linked to the nitrogen atom, may be replaced by a carbonyl group, or (ii) linked to the phenyl nucleus, may be replaced by an oxygen or sulphur atom, by a sulphinyl or sulphonyl group or by an imino group optionally substituted by a $C_{1-3}$-alkyl group, B denotes a bond, a methylene, ethylene, ethenylene or n-propylene group optionally substituted by one or two $C_{1-3}$-alkyl groups, whilst (iii) in the abovementioned methylene, ethylene or n-propylene groups, if Y denotes a carbonyl or thiocarbonyl group, a methylene group may be replaced by an oxygen atom or by an imino group optionally substituted by a $C_{1-3}$-alkyl group, or (iv) in the abovementioned ethylene or n-propylene groups, if Y denotes a methylene group, a methylene group in the 3 or 4 position relative to the nitrogen atom may be replaced by an oxygen atom or by an imino group optionally substituted by a $C_{1-3}$-alkyl group, W denotes a methine group or a nitrogen atom and Y denotes a methylene, carbonyl or thiocarbonyl group.

Preferred compounds of the above general formula I however are those wherein $R_a$, $R_c$, $R_d$, A, B, W and Y are as hereinbefore defined and $R_b$ denotes an amidino group optionally substituted by a $C_{1-10}$-alkoxycarbonyl or phenyl-$C_{1-3}$-alkoxycarbonyl group, the optical antipodes and the salts thereof.

Particularly preferred compounds of the above general formula I however are those wherein $R_a$ denotes an $R_1NR_2$, $R_1'NR_2'$—X or $(R_3X)NR_1$— group wherein $R_1$ denotes a hydrogen atom, a $C_{1-4}$-alkyl group, which may be substituted by a phenyl, carboxy, $C_{1-2}$-alkoxycarbonyl or aminocarbonyl group, whilst the amino group of the aminocarbonyl group may additionally be mono or disubstituted by $C_{1-4}$-alkyl, phenyl, benzyl, carboxy-$C_{1-2}$-alklyl or $C_{1-2}$-alkoxycarbonyl-$C_{1-2}$-alkyl groups and the substituents may be identical or different, or an ethyl group, which is terminally substituted by an amino, acetylamino, morpholino, phenylamino or N-benzyloxycarbonyl-phenylamino group, $R_2$ denotes a hydrogen atom, a $C_{1-3}$-alky group optionally substituted by one or two phenyl groups or by a naphthyl group, a cyclohexyl group, or a phenyl group optionally substituted by a chlorine atom, by a 2-aminoethyl or 2-acetylamino group, $R_1'$ and $R_2'$ have the meanings given hereinbefore for $R_1$ and $R_2$ or together with the nitrogen atom between them denote a pyrrolidino or piperidino group optionally substituted by a methyl, carboxy or $C_{1-2}$-alkoxycarbonyl group, a pyrrolidino or piperidino group substituted by two methyl groups, or a morpholino group, $R_3$ denotes a straight-chained or branched $C_{1-5}$-alkyl group, which may be substituted in the 1, 2 or 3 position by a phenyl, carboxy or $C_{1-3}$-alkoxycarbonyl group or in the 2 or 3 position by a chlorine atom, a trifluoromethyl group, a phenyl or naphthyl group, which may be substituted in each case by a fluorine, chlorine or bromine atom, by a trifluoromethyl, $C_{1-3}$-alkyl, $C_{1-3}$-alkoxy, amino, $C_{1-3}$-alkylamino, di-($C_{1-3}$-alkyl)amino or aminocarbonyl group, whilst the abovementioned phenyl groups may additionally be substituted by one to three methyl groups, a phenyl or aminophenyl group substituted by two chlorine or bromine atoms, a thienyl group substituted by a chlorine or bromine atom, a $C_{3-7}$-cycloalkyl, quinolyl, isoquinolyl or benzimidazolyl group or $R_1$ and $R_3$ together denote an n-alkylene group with 3 to 5 carbon atoms, wherein an ethylene group linked to the $SO_2$ or CO— group may be replaced by a 1,2-phenylene group, and X denotes a carbonyl or sulphonyl group, or $R_a$ also denotes a $C_{2-3}$-alkanoyl group which is substituted by a carboxy-$C_{1-3}$-alkyl or $C_{1-3}$-alkoxycarbonyl-$C_{1-3}$-alkyl group and a benzoyl, naphthoyl, phenylsulphonyl or naphthylsulphonyl group, $R_b$ denotes an amidino group optionally substituted by a $C_{1-10}$-alkoxycarbonyl or phenyl-$C_{1-3}$-alkoxycarbonyl group, $R_c$ denotes a hydrogen, fluorine, chlorine, bromine or iodine atom, a methyl, methoxy, aminocarbonyl, amino or nitro group or an amino group optionally substituted by a straight-chained $C_{2-4}$-alkanoyl group, wherein the alkanoyl moiety may be terminally substituted by a carboxy or $C_{1-3}$-alkoxycarbonyl group, $R_d$ denotes a hydrogen atom, A denotes an ethylene, n-propylene or n-butylene group optionally substituted by one or two methyl groups, whilst a methylene group of an ethylene or n-propylene group optionally sub-stituted by one or two methyl groups, which is (i) linked to the nitrogen atom, may be replaced by a carbonyl group, B denotes a bond, a methylene, ethylene, ethenylene or n-propylene group optionally substituted by one or two methyl groups, whilst (iii) in the abovementioned methylene, ethylene or n-propylene groups, if Y denotes a carbonyl or thiocarbonyl group, a methylene group may be replaced by an oxygen atom or by an imino group optionally substituted by a methyl group, or (iv) in the abovementioned ethylene or n-propylene groups, if Y denotes a methylene group, a methylene group in the 3 or 4 position relative to the nitrogen atom may be replaced by an oxygen atom or by an imino group optionally substituted by a methyl group, W denotes a methine group and Y denotes a methylene, carbonyl or thiocarbonyl group, particularly the abovementioned compounds wherein $R_a$ denotes a $(R_3SO_2)NR_1$— group, the optical antipodes and the salts thereof.

Most particularly preferred compounds are those wherein $R_a$ denotes a $(R_3SO_2)NR_1$— group, whilst $R_1$ and $R_3$ are as hereinbefore defined, $R_b$ denotes an amidino group optionally substituted by a $C_{1-10}$-alkoxycarbonyl or phenyl-$C_{1-3}$-alkoxycarbonyl group, $R_c$ and $R_d$ each denote a hydrogen atom, A denotes an n-propylene group optionally substituted by a methyl group, B denotes an ethylene group, W denotes a methine group and Y denotes a carbonyl group, the optical antipodes and the salts thereof.

The following particularly preferred compounds are mentioned by way of example:

(a) 1-[3-(4-amidino-phenyl)propionyl]-6-(4-fluoro-phenylsulphonamido)-1,2,3,4-tetrahydro-quinoline, (b) 1-[3-(4-amidino-phenyl)propionyl]-6-butylsulphonamido-1,2,3,4-tetrahydro-quinoline, (c) 1-[3-(4-amidino-phenyl)propionyl]-5-phenylsulphonamido-1,2,3,4-tetrahydro-quinoline, (d) 1-[3-(4-amidino-phenyl)propionyl]-3-methyl-6-phenylsulphonamido-1,2,3,4-tetrahydro-quinoline, (e) 1-[3-(4-amidino-phenyl)propionyl]-6-(5-chloro-thien-2-ylsulphonamido)-1,2,3,4-tetrahydro-quinoline, (f) 1-[3-(4-amidino-phenyl)propionyl]-6-phenylsulphonamido-1,2,3,4-tetrahydro-quinoline, (g) 1-[3-(4-amidino-phenyl)propionyl]-6-(N-methyl-phenylsulphonamido)-1,2,3,4-tetrahydro-quinoline, (h) 1-[3-(4-amidino-phenyl)propionyl]-6-(N-ethoxycarbonylmethyl-phenylsulphonamido)-1,2,3,4-tetrahydro-quinoline,
(i) 1-[3-(4-amidino-phenyl)propionyl]-6-(N-carboxymethyl-phenylsulphonamido)-1,2,3,4-tetrahydro-quinoline,
(j) 1-[3-(4-aminomethyl-phenyl)propionyl]-6-phenylsulphonamido-1,2,3,4-tetrahydro-quinoline,
(k) 1-[3-(4-amidino-phenyl)propyl]-6-phenylsulphonamido-1,2,3,4-tetrahydro-quinoline,
(l) 1-[3-(4-methyloxycarbonyl-amidino-phenyl)propionyl]-6-phenylsulphonamido-1,2,3,4-tetrahydro-quinoline,
(m) 1-[3-(4-amidino-phenyl)-propionyl]-6-(N-phenyl-methylaminocarbonyl)-1,2,3,4-tetrahydro-quinoline,
(n) 1-[(4-amidino-phenoxy)-acetyl]-6-[N-(1-naphthylsulphonyl)-hydroxycarbonylmethylamino]-1,2,3,4-tetrahydro-quinoline,
(o) 1-[3-(4-amidino-phenyl)-propionyl]-6-diethylaminocarbonyl-1,2,3,4-tetrahydro-quinoline,
(p) 1-[3-(4-amidino-phenyl)-propionyl]-6-(N-benzoyl-methylamino)-1,2,3,4-tetrahydro-quinoline,
(q) 1-[3-(4-amidino-phenyl)-propionyl]-6-(N-benzoyl-methylamino)-1,2,3,4-tetrahydro-quinoline,
(r) 1-[3-(4-amidino-phenyl)-propionyl]-6-[N-(naphth-1-yl-sulphonyl)-hydroxycarbonylmethylamino]-1,2,3,4-tetrahydro-quinoline,
(s) 1-[3-(4-amidino-phenyl)-propionyl]-6-[N-(1-naphthoyl)-hydroxycarbonylmethylamino]-1,2,3,4-tetrahydro-quinoline,
(t) 1-[3-(4-amidino-phenyl)-propionyl]-6-(N-benzoyl-hydroxycarbonylmethylamino]-1,2,3,4-tetrahydro-quinoline,
(u) 1-[3-(4-amidino-phenyl)-propionyl]-6-[N-(quinoline-8-sulphonyl)-hydroxycarbonylmethylamino]-1,2,3,4-tetrahydro-quinoline and
(v) 1-[3-(4-amidino-phenyl)-propionyl]-6-[N-(n-butylsulphonyl)-hydroxycarbonylmethylamino]-1,2,3,4-tetrahydro-quinoline,
the optical antipodes and the salts thereof.

According to the invention, the new compounds of general formula I may be obtained by the following processes, for example:

a) In order to prepare a compound of general formula I wherein $R_b$ denotes a cyano group and Y denotes a methylene group:

reacting a compound of general formula

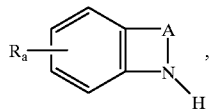

(II)

wherein

A and $R_a$ are as hereinbefore defined, with a compound of general formula

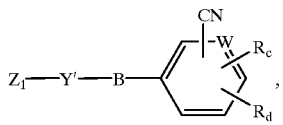

(III)

wherein

B, W, $R_c$ and $R_d$ are as hereinbefore defined,

Y' denotes a methylene group and $Z_1$ denotes a leaving group such as a halogen atom, a sulphonic acid group, e.g. a chlorine, bromine or iodine atom, a methanesulphonyloxy or p-toluenesulphonyloxy group.

The reaction is usefully carried out in a solvent or mixture of solvents such as methylene chloride, chloroform, ether, tetrahydrofuran, dioxan or dimethylformamide optionally in the presence of an inorganic or organic base, such as sodium hydroxide, potassium carbonate, triethylamine or pyridine, whilst these last two may simultaneously serve as solvent, at temperatures between −25 and 100° C., but preferably at temperatures between −10 and 80° C.

b) In order to prepare a compound of general formula I wherein $R_b$ denotes a cyano group and Y denotes a carbonyl group:

reacting a compound of general formula

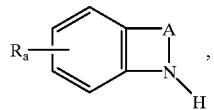

(II)

wherein

A and $R_a$ are as hereinbefore defined, with a compound of general formula

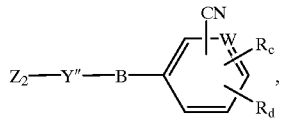

(IV)

wherein

B, W, $R_c$ and $R_d$ are as hereinbefore defined,

Y" denotes a carbonyl group and $Z_2$ denotes a hydroxy group or a leaving group such as a halogen atom, e.g. a chlorine or bromine atom.

The reaction is usefully carried out in a solvent such as methylene chloride, chloroform, carbon tetrachloride, ether, tetrahydrofuran, dioxan, benzene, toluene, acetonitrile or dimethylformamide optionally in the presence of an acid activating agent or a dehydrating agent, e.g. in the presence of ethyl chloroformate, thionyl chloride, phosphorus trichloride, phosphorus pentoxide, N,N'-dicyclohexylcarbodiimide, N,N'-dicyclohexylcarbodiimide/N-hydroxy-succinimide, NN-carbonyldiimidazole or N,N'-thionyldiimidazole or triphenylphosphine/carbon tetrachloride, and optionally in the presence of an inorganic base such as sodium carbonate or an organic base such as triethylamine or pyridine, which may simultaneously serve as solvent, at temperatures between −25° C. and 250° C., but preferably at temperatures between −10° C. and the boiling temperature of the solvent used.

c) In order to prepare a compound of general formula I wherein $R_a$ denotes an $R_1N(XR_3)-$ group and $R_b$ denotes a cyano group:

reacting a compound of general formula

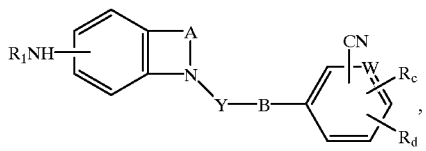

(V)

wherein

A, B, W, Y, $R_c$, $R_d$ and $R_1$ are as hereinbefore defined, with a compound of general formula $$Z_3—X—R_3, \quad (VI)$$

wherein

X and $R_3$ are as hereinbefore defined and $Z_3$ denotes a hydroxy group or a leaving group such as a halogen atom, e.g. a chlorine or bromine atom.

The reaction is usefully carried out in a solvent or mixture of solvents such as water, methylene chloride, chloroform, ether, tetrahydrofuran, dioxan or dimethylformamide optionally in the presence of an inorganic or organic base, such as sodium hydroxide, potassium carbonate, triethylamine or pyridine, whilst these last two may simultaneously serve as solvent, at temperatures between −25 and 100° C., but preferably at temperatures between −10 and 80° C.,.

If $Z_3$ denotes a hydroxy group and X denotes a carbonyl group, the reaction is preferably carried out in the presence of an acid activating agent or a dehydrating agent, e.g. in the presence of ethyl chloroformate, thionylchloride, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole or N,N'-thionyldiimidazole or triphenylphosphine/carbon tetrachloride, and optionally in the presence of an inorganic base such as sodium carbonate or an organic base such as triethylamine or pyridine, which may simultaneously serve as solvent, at temperatures between −25° C. and 150° C., but preferably at temperatures between −10° C. and the boiling temperature of the solvent used.

d) In order to prepare a compound of general formula I wherein $R_a$ denotes an $R_1NR_2$ or $R_1N(XR_3)$— group, wherein $R_1$ is as hereinbefore defined with the exception of the hydrogen atom, and $R_b$ denotes a cyano group or an amidino group substituted by a $C_{1-10}$-alkoxycarbonyl group or phenyl-$C_{1-3}$-alkoxycarbonyl group:

reacting a compound of general formula

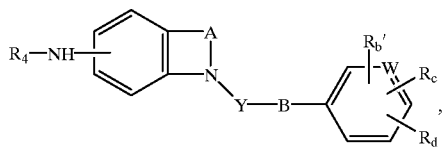

(VII)

wherein

A, B, W, Y, $R_c$ and $R_d$ are as hereinbefore defined, $R_4$ has the meanings given for $R_2$ hereinbefore or denotes an $R_3$—X— group, whilst $R_3$ and X are as hereinbefore defined, and $R_b'$ denotes a cyano group or an amidino group substituted by a $C_{1-10}$-alkoxycarbonyl group or phenyl-$C_{1-3}$-alkoxycarbonyl group, with a compound of general formula $$Z_4—R_1', \quad (VIII),$$

wherein $R_1'$ denotes a $C_{1-5}$-alkyl group, which may be substituted by a phenyl, carboxy, $C_{1-4}$-alkoxycarbonyl or aminocarbonyl group, whilst the amino group of the aminocarbonyl group may additionally be mono or disubstituted by $C_{1-4}$-alkyl, phenyl-$C_{1-3}$-alkyl, phenyl, carboxy-$C_{1-3}$-alkyl or $C_{1-3}$-alkoxycarbonyl-$C_{1-3}$-alkyl groups and the substituents may be identical or different, or a straight-chained $C_{1-3}$-alkyl group, which is terminally substituted by a di-($C_{1-3}$-alkyl)amino, pyrrolidino, piperidino or morpholino group, and $Z_4$ denotes a leaving group such as a halogen atom, e.g. a chlorine or bromine atom.

The reaction is usefully carried out in a solvent or mixture of solvents such as water, methylene chloride, chloroform, ether, tetrahydrofuran, dioxan or dimethylformamide optionally in the presence of an inorganic or organic base, such as sodium hydroxide, potassium carbonate, triethylamine or pyridine, whilst these last two may simultaneously serve as solvent, at temperatures between −25 and 100° C., but preferably at temperatures between −10 and 80° C.

e) In order to prepare a compound of general formula I wherein $R_a$ denotes a nitro group and $R_b$ denotes a cyano group:

nitrating a compound of general formula

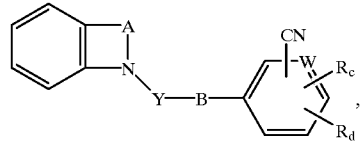

(IX)

wherein

A, B, W, Y, $R_c$ and $R_d$ are as hereinbefore defined.

The nitration is preferably carried out in a solvent such as glacial acetic acid or tetrahydrofuran in the presence of a nitration agent such as dilute or concentrated nitric acid or nitric acid/sulphuric acid at temperatures between 0 and 50° C., preferably at ambient temperature. The nitration may also be carried out without a solvent. Moreover, if a mixture of positional isomers is obtained it may be resolved into the individual isomers by conventional methods, e.g. by chromatography.

f) In order to prepare a compound of general formula I wherein $R_a$ denotes an amino group and $R_b$ denotes a cyano group:

reduction of a compound of general formula

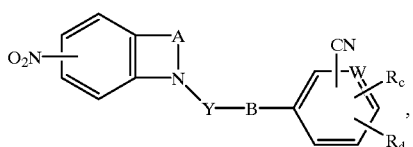

(X)

wherein

A, B, W, Y, $R_c$ and $R_d$ are as hereinbefore defined.

The reduction is preferably carried out in a solvent such as water, water/ethanol, methanol, glacial acetic acid, ethyl acetate or dimethylformamide, expediently with hydrogen in the presence of a hydrogenation catalyst such as Raney nickel, platinum or palladium/charcoal, with metals such as iron, tin or zinc in the presence of an acid, with salts such as iron(II)sulphate, tin(II)chloride, sodium sulphide, sodium hydrogen sulphite or sodium dithionite, or with hydrazine in the presence of Raney nickel at temperatures between 0 and 80° C., but preferably at temperatures between 20 and 40° C.

g) In order to prepare a compound of general formula I, wherein $R_b$ denotes an amidino group:

reacting a compound of general formula

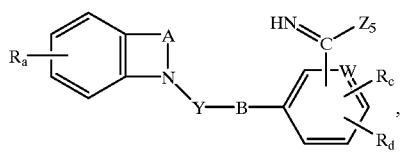
(XI)

optionally formed in the reaction mixture wherein

A, B, W, Y, $R_a$, $R_c$ and $R_d$ are as hereinbefore defined and $Z_5$ denotes an alkoxy or aralkoxy group such as the methoxy, ethoxy, n-propoxy, isopropoxy or benzyloxy group or an alkylthio or aralkylthio group such as the methylthio, ethylthio, n-propylthio or benzylthio group, with ammonia or with the acid addition salts thereof.

The reaction is usefully carried out in a solvent such as methanol, ethanol, n-propanol, water, methanol/water, tetrahydrofuran or dioxan at temperatures between −10 and 150° C., preferably at temperatures between 0 and 120° C., with a corresponding free amine or with a corresponding acid addition salt such as for example the corresponding ammonium carbonates, acetates or chlorides.

A compound of general formula XI is obtained for example by reacting a corresponding nitrite with a corresponding alcohol such as methanol, ethanol, n-propanol, isopropanol or benzyl alcohol in the presence of an acid such as hydrochloric acid or by reacting a corresponding amide with a trialkyloxonium salt such as triethyloxonium-tetrafluoroborate in a solvent such as methylene chloride, tetrahydrofuran or dioxan at temperatures between −10 and 50° C., but preferably at temperatures between 0 and 30° C., or a corresponding nitrite with hydrogen sulphide, conveniently in a solvent such as pyridine or dimethylformamide and in the presence of a base such as triethylamine and subsequent alkylation of the thioamide formed with a corresponding allyl or aralkyl halide or by reacting a corresponding nitrite with an alkoxide such as sodium methoxide in a solvent such as dioxan or tetrahydrofuran, but preferably in the corresponding alcohol. During the reactions with an alcohol any ester group present may be transesterified.

h) In order to prepare a compound of general formula I wherein $R_b$ denotes an amidino group substituted by a $C_{1-10}$-alkoxycarbonyl group or phenyl-$C_{1-3}$-alkoxycarbonyl group:

reacting a compound of general formula

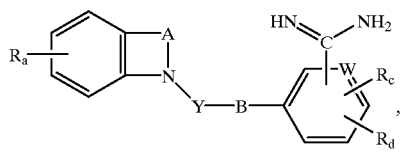
(XII)

wherein

A, B, W, Y, $R_a$, $R_c$ and $R_d$ are as hereinbefore defined, with a compound of general formula $$Z_6\text{—CO—OR}_4 \qquad (XIII)$$

wherein $R_4$ denotes a $C_{1-10}$-alkyl or phenyl-$C_{1-3}$-alkyl group and $Z_6$ denotes a leaving group such as a halogen atom, e.g. a chlorine or bromine atom.

The reaction is usefully carried out in a solvent such as tetrahydrofuran, methylene chloride, chloroform, dimethylformamide, water or mixtures of these solvents, optionally in the presence of a base such as sodium carbonate, potassium carbonate or sodium hydroxide solution or in the presence of an organic base such as triethylamine, N-ethyldiisopropylamine, N-methylmorpholine or pyridine, which may simultaneously serve as solvent, at temperatures between −30 and 100° C., but preferably at temperatures between −10 and 60° C.

i) In order to prepare a compound of general formula I wherein $R_b$ denotes an aminomethyl group:

reduction of a compound of general formula

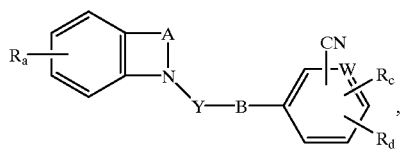
(XIV)

wherein

A, B, W, Y, $R_a$, $R_c$ and $R_d$ are as hereinbefore defined.

The reduction is preferably carried out in a suitable solvent such as methanol, methanol/water, methanol/water/ammonia, ethanol, ether, tetrahydrofuran, dioxan or dimethylformamide optionally with the addition of an acid such as hydrochloric acid in the presence of catalytically activated hydrogen, e.g. hydrogen in the presence of Raney nickel, platinum or palladium/charcoal, or in the presence of a metal hydride such as sodium borohydride, lithium borohydride or lithium aluminium hydride at temperatures between 0 and 100° C., preferably at temperatures between 20 and 80° C.

j) In order to prepare a compound of general formula I wherein $R_a$ denotes an $R_1NR_2$— group, wherein $R_1$ is as hereinbefore defined with the exception of the hydrogen atom, and $R_b$ denotes a cyano group or an amidino group substituted by a $C_{1-10}$-alkoxycarbonyl group or phenyl-$C_{1-3}$-alkoxycarbonyl group:

reacting a compound of general formula

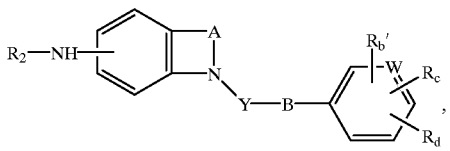 (XV)

wherein

A, B, W, Y, $R_2$, $R_c$ and $R_d$ are as hereinbefore defined and $R_b'$ denotes a cyano group or an amidino group substituted by a $C_{1-10}$-alkoxycarbonyl group or phenyl-$C_{1-3}$-alkoxycarbonyl group, with a compound of general formula $Z_7$—$R_1'$, (XVI), wherein $R_1'$ is as hereinbefore defined and $Z_7$ denotes a leaving group such as a halogen atom, e.g. a chlorine or bromine atom, or together with a hydrogen atom of the adjacent carbon atom denotes an oxygen atom.

The reaction is usefully carried out in a solvent or mixture of solvents such as water, methylene chloride, chloroform, ether, tetrahydrofuran, dioxan or dimethylformamide optionally in the presence of an inorganic or organic base, such as sodium hydroxide, potassium carbonate, triethylamine or pyridine, whilst these last two may simultaneously serve as solvent, at temperatures between −25 and 100° C., but preferably at temperatures between −10 and 80° C.

The reaction with a carbonyl compound of general formula XVI is preferably carried out in a suitable solvent such as methanol, methanol/water, methanol/water/ammonia, ethanol, ether, tetrahydrofuran, dioxan or dimethylformamide optionally with the addition of an acid such as hydrochloric acid in the presence of catalytically activated hydrogen, e.g. hydrogen in the presence of Raney nickel, platinum or palladium/charcoal, or in the presence of a metal hydride such as sodium borohydride, lithium borohydride or lithium aluminium hydride at temperatures between 0 and 100° C., preferably at temperatures between 20 and 80° C.

k) In order to prepare a compound of general formula I wherein $R_b$ denotes a cyano group and Y denotes a carbonyl group:

reacting a compound of general formula

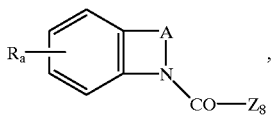 (XVII)

wherein

A and $R_a$ are as hereinbefore defined and $Z_8$ denotes a leaving group such as a halogen atom, e.g. a chlorine, bromine or iodine atom, with a compound of general formula

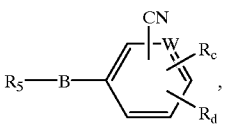 (XVIII)

wherein

B, W, $R_c$ and $R_d$ are as hereinbefore defined and $R_5$ denotes an amino group optionally substituted by a $C_{1-3}$-alkyl group.

The reaction is usefully carried out in a solvent or mixture of solvents such as water, methylene chloride, chloroform, ether, tetrahydrofuran, dioxan or dimethylformamide, optionally in the presence of an inorganic or organic base, such as sodium hydroxide, potassium carbonate, triethylamine or pyridine, whilst these last two may simultaneously serve as solvent, at temperatures between −25 and 100° C., but preferably at temperatures between −10 and 80° C.

If according to the invention a compound of general formula I is obtained wherein X denotes a carbonyl group, this may be converted by means of a sulphurising agent into a corresponding thiocarbonyl compound or if according to the invention a compound of general formula I is obtained wherein $R_a$ contains an acyl group, this may be converted by hydrolysis into a compound of general formula I wherein $R_a$ denotes an $R_1NH$— group or wherein $R_a$ contains a carboxy group, or if according to the invention a compound of general formula I is obtained wherein $R_a$ denotes or contains a carboxy or sulphonic acid group, this may be converted by amidation into a corresponding amide compound of general formula I.

The reaction is carried out with a sulphurising agent such as phosphorus pentasulphide or 2,4-bis(4-methoxyphenyl)-1,3-di-thia-2,4diphosphetan-2,4-disulphide usefully in a solvent such as toluene or xylene at temperatures between 50 and 150° C., e.g. at the boiling temperature of the reaction mixture.

The subsequent hydrolysis is preferably carried out hydrolytically in an aqueous solvent, e.g. in water, isopropanol/water, tetrahydrofuran/water or dioxan/water, in the presence of an acid such as hydrochloric acid or sulphuric acid or in the presence of an alkali metal base such as sodium hydroxide or potassium hydroxide at temperatures between 0 and 100° C., preferably at the boiling temperature of the reaction mixture.

The subsequent amidation is optionally carried out in a solvent or mixture of solvents such as methylene chloride, dimethylformamide, benzene, toluene, chlorobenzene, tetrahydrofuran, benzene/tetrahydrofuran or dioxan with a corresponding amine optionally in the presence of a dehydrating agent, e.g. in the presence of isobutyl chloroformate, tetraethyl orthocarbonate, trimethyl orthoacetate, 2,2-dimethoxypropane, tetramethoxysilane, thionylchloride, trimethylchlorosilane, phosphorus trichloride, phosphorus pentoxide, N,N'-dicyclohexyl-carbodiimide, N,N'-dicyclohexylcarbodiimide/N-hydroxy-succinimide, N,N'-dicyclohexylcarbodiimide/1-hydroxy-bentriazole, 2-(1H-benzotriazol-1-yl)-1,1,3,3-tetramethyluronium-tetrafluoroborate, 2-(1H-benzotriazol-1-yl)-1,1,3,3-tetramethyluronium-tetrafluoroborate/1-hydroxy-benztriazole, N,N'-carbonyldiimidazole or triphenylphosphine/carbon tetrachloride, and optionally with the addition of a base such as pyridine, 4-dimethylaminopyridine, N-methyl-morpholine or triethylamine, conveniently at temperatures between 0 and 150° C., preferably at temperatures between 0 and 100° C.

The reaction of a corresponding reactive carboxylic or sulphonic acid such as the esters, imidazolides or halides thereof with a corresponding amine is preferably carried out in a corresponding amine as solvent, optionally in the presence of another solvent such as methylene chloride or ether and preferably in the presence of a tertiary organic base such as triethylamine, N-ethyl-diisopropylamine or N-methyl-morpholine at temperatures between 0 and 150° C., preferably at temperatures between 50 and 100° C.

In the reactions described hereinbefore, any reactive groups present such as hydroxy, carboxy, amino, alkylamino or imino groups may be protected during the reaction by conventional protecting groups which are cleaved again after the reaction.

For example, a protecting group for a hydroxy group may be a trimethylsilyl, acetyl, benzoyl, tert.butyl, trityl, benzyl or tetrahydropyranyl group, protecting groups for a carboxy group may be a trimethylsilyl, methyl, ethyl, tert.butyl, benzyl or tetrahydropyranyl group and protecting groups for an amino, alkylamino or imino group may be an acetyl, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, tetrahydrofuran/water or dioxan/water, in the presence of an acid such as trifluoroacetic acid, hydrochloric acid or sulphuric acid or in the presence of an alkali metal base such as lithium hydroxide, sodium hydroxide or potassium hydroxide or by ether splitting, e.g. in the presence of iodotrimethylsilane, at temperatures between 0 and 100° C., preferably at temperatures between 10 and 50° C.

However, a benzyl, methoxybenzyl or benzyloxycarbonyl group is cleaved, for example, hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, but preferably 3 to 5 bar.

A tert.butyl or tert.butyloxycarbonyl group is preferably cleaved by treating with an acid such as trifluoroacetic acid or hydrochloric acid, optionally using a solvent such as methylene chloride, dioxan or ether.

Moreover, the compounds of general formula I obtained may be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-to-lyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds of formula I may be converted into the salts thereof, particularly for pharmaceutical use into their physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid, maleic acid or methanesulphonic acid.

Moreover, if the new compounds of formula I contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, arginine, cyclohexylamine, ethanolamine, diethanolamine and triethanolamine.

The compounds of general formulae II to XVIII used as starting materials are obtained by methods known from the literature or are known from the literature.

Thus, for example, a compound of general formula II may be obtained by hydrogenation of a corresponding unsaturated compound and a starting compound of general formulae V, VII, IX, X, XI and XIV by alkylation or acylation of a compound of general formula II thus obtained.

As already mentioned hereinbefore, the new compounds of general formula I and the salts thereof have valuable properties. Thus, the compounds of general formula I wherein $R_b$ denotes a hydrogen atom, a nitro or cyano group are valuable intermediate products for preparing the other compounds of general formula I, and the compounds of general formula I wherein $R_b$ denotes one of the abovementioned optionally substituted aminomethyl or amidino groups, and the physiologically acceptable salts thereof have valuable pharmacological properties, particularly a thrombin-inhibiting activity and an inhibitory effect on thrombocyte aggregation, an activity which extends the thrombin time and an inhibiting effect on related serine proteases such as, for example, trypsin, plasmin, urokinase factor VIIa, factor Xa, factor IX, factor XI and factor XII.

For example, the compounds

A=1-[3-(4-amidinophenyl)propionyl]-6-butylsulphonamido-1,2,3,4-tetrahydro-quinoline-hydrochloride, B=1-[3-(4-amidino-phenyl)-propionyl]-1,2,3,4-tetrahydro-quinoline-6-carboxylic acid -methyl-N-phenyl-amide, C=1-[3-(4-amidino-phenyl)-propionyl]-1,2,3,4-tetrahydro-quinoline-6-carboxylic acid-diethylamide, D=N-benzyl-N-{1-[3-(4-amidino-phenyl)-propionyl]-1,2,3,4-tetrahydro-quinoline-6-yl}-acetamide, E=({1-[3-(4-amidino-phenyl)-propionyl]-1,2,3,4-tetrahydro-quinoline-6-carbonyl}-phenyl-amino)-acetic acid, F=1-[3-(4-amidino-phenyl)propionyl]-6-phenylsulphonamido-1,2,3,4-tetrahydro-quinoline-hydrochloride,
G=(i) 1-[3-(4-amidino-phenyl)propionyl]-6-(N-carboxymethyl-phenylsulphonamido)-1,2,3,4-tetrahydro-quinoline,
H=[{1-[3-(4-amidino-phenyl)-propionyl]-1,2,3,4-tetrahydro-quinoline-6-yl}-(naphthalin-1-sulphonyl)-amino]-acetic acid and
I=[{1-[3-(4-amidino-phenyl)-propionyl]-1,2,3,4-tetrahydro-quinoline-6-yl}-(quinoline-8-sulphonyl)-amino]-acetic acid were investigated for their effect on the thrombin time as follows:
Material: Plasma, from human citrated blood.
  Test thrombin (bovine), 30 U/ml, Behring Werke, Marburg
  Diethylbarbiturate acetate buffer, ORWH 60/61, Behring Werke, Marburg
  Biomatic B10 coagulometer, Sarstedt
Method The thrombin time was determined using a Biomatic B10 coagulometer made by Messrs Sarstedt.

The test substance was added to the test vessels prescribed by the manufacturer with 0.1 ml of human citrate plasma and 0.1 ml of diethylbarbiturate buffer (DBA buffer). The mixture was incubated for one minute at 37° C. The clotting reaction was started by the addition of 0.3 U of test thrombin in 0.1 ml of DBA buffer. Because of the design of the apparatus, the time taken for the mixture to clot was measured as the thrombin was added. Mixtures to which 0.1 ml of DBA buffer had been added were used as controls.

According to the definition the effective concentration of substance at which the thrombin time was double that of the control was determined by means of a dosage/activity curve.

The following Table contains the values found:

| Substance | Thrombin time ($ED_{200}$ in $\mu M$) |
|---|---|
| A | 0.08 |
| B | 0.02 |
| C | 0.10 |
| D | 0.05 |
| E | 0.04 |
| F | 0.04 |
| G | 0.03 |
| H | 0.02 |
| I | 0.03 |

Moreover, no toxic side effects could be detected in rats when the above compounds were administered in a dosage of 20 mg/kg i.v. or 100 mg/kg p.o. The compounds are therefore well tolerated.

In view of their pharmacological properties the new compounds and the physiologically acceptable salts thereof are suitable for the prevention and treatment of venous and arterial thrombotic diseases, such as for example the treatment of deep leg vein thrombosis, for preventing reocclusions after bypass operations or angioplasty (PT(C)A), and occlusion in peripheral arterial diseases such as pulmonary embolism, disseminated intravascular coagulation, for preventing coronary thrombosis, stroke and the occlusion of shunts. In addition, the compounds according to the invention are suitable for antithrombotic support in thrombolytic treatment, such as for example with rt-PA or streptokinase, for preventing long-tern restenosis after PT(C)A, for preventing metastasis and the growth of clot-dependent tumours and fibrin-dependent inflammatory processes.

The dosage required to achieve such an effect is appropriately 0.1 to 50 mg/kg, preferably 0.5 to 30 mg/kg by intravenous route, and 1 to 100 mg/kg, preferably 0.5 to 50 mg/kg by oral route, in each case administered 1 to 4 times a day. For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The Examples which follow are intended to illustrate the invention:
Preparation of the Starting Compounds

EXAMPLE I 3-(4-cyano-phenyl)propionic Acid 100.1 g (0.578 mol) of 4-cyano-cinnamic acid are taken up in 1400 ml 1N potassium carbonate solution and hydrogenated over palladium-charcoal at 5 bar for 2.5 hours. Then the solution is made slightly acidic and the precipitate is suction filtered, and then dried in the circulating air drier.
  Yield: 90.8 g (89.6% of theory),
  Melting point: 137–139° C.

EXAMPLE II 6-phenylsulphonamido-quinoline 61.5 g (0.426 mol) of 6-amino-quinoline are dissolved in 210 ml pyridine and combined with 82.8 g (0.469 mol) of benzenesulphonic acid chloride whilst cooling with ice. Then the solution is heated to 100° C. and after 20 minutes slowly cooled to 45° C. Then 85 ml of 6N sodium hydroxide solution are added and the mixture is evaporated to dryness. The precipitate remaining is washed first with water, then with ethanol and then dried.
  Yield: 106.6 g (87.9% of theory),
  Melting point: 219–221° C.
  The following are prepared analogously:
  (1) 6-(2-naphthyl-sulphonamido)-quinoline
    Melting point: 152° C.
  (2) 6-(1-naphthyl-sulphonamido)-quinoline
    Melting point: 248° C.
  (3) 6-(4-fluoro-phenylsulphonamido)-quinoline
    Melting point: 220–221° C.
  (4) 6-butylsulphonamido-quinoline
    Melting point: 82–84° C.
  (5) 5-phenylsulphonamido-quinoline
    Melting point: 112° C.
  (6) 7-phenylsulphonamido-quinoline
    Melting point: 185–187° C.
  (7) 7-benzylsulphonanido-quinoline
    $R_f$ value: 0.73 (silica gel; methylene chloride/methanol=9:1)
  (8) 6-benzylcarboxamido-quinoline
    Melting point: 146–149° C.
  (9) 6-phenylsulphonamido-2-methyl-quinoline
    $R_f$ value: 0.61 (silica gel; ethyl acetate)
  (10) 6-benzylsulphonamido-quinoline
    Melting point: 179–181° C.
  (11) 6-benzoylamino-quinoline
    Melting point: 155–158° C.

(12) 6-(4-chloro-phenylsulphonamido)-quinoline
(13) 6-(4-bromo-phenylsulphonamido)-quinoline
(14) 6-(3-chloro-phenylsulphonamido)-quinoline
(15) 6-(3-bromo-phenylsulphonamido)-quinoline
(16) 6-(4-methyl-phenylsulphonamido)-quinoline EXAMPLE III
6-(N-methyl-phenylsulphonamido)-quinoline 4.0 g of 6-phenylsulphonamido-quinoline are dissolved in 50 ml dimethylsulphoxide and combined at ambient temperature with 1.83 g of potassium tert. butoxide. Then 2.13 g of methyliodide are added dropwise and the mixture is stirred overnight. Then it is poured onto 300 ml of ice water and extracted with ethyl acetate. The organic phase is dried and concentrated by evaporation.

Yield: 3.0 g (71.8% of theory),
Melting point: 101–103° C.

The following are prepared analogously:
(1) 6-[N-(2-phenylethyl)-phenylsulphonamido]quinoline
(2) 6-[N-(ethoxycarbonylmethyl)-phenylsulphonamido] quinoline EXAMPLE IV
6-phenylsulphonamido-1,2,3,4-tetrahydro-quinoline 106.6 g (0.375 mol) of 6-phenylsulphonamido-quinoline are dissolved in 1400 ml glacial acetic acid and hydrogenated over 17 g platinum oxide at 3 bar for 70 minutes. Then the catalyst is removed by suction filtering, concentrated by evaporation and the residue is washed with a little ethanol and dried.

Yield: 98.4 g (91.0% of theory),
Melting point: 160–162° C.

The following are prepared analogously:
(1) 6-(2-naphthyl-sulphonamido)-1,2,3,4-tetrahydro-quinoline
   Melting point: 152–154° C.
(2) 6-(1-naphthyl-sulphonamido)-1,2,3,4-tetrahydro-quinoline
   Melting point: 175–176° C.
(3) 6-(4-fluoro-phenylsulphonamido)-1,2,3,4-tetrahydro-quinoline
   Melting point: 85° C.
(4) 6-butylsulphonamido-1,2,3,4-tetrahydro-quinoline
   $C_{13}H_{20}N_2O_2S$ (268,36)

| | | | | | | |
|---|---|---|---|---|---|---|
| Calc.: | C | 58.18 | H | 7.51 | N | 10.43 |
| Found: | | 57.95 | | 7.70 | | 10.22 |

(5) 6-(N-methyl-phenylsulphonamido)-1,2,3,4-tetrahydro-quinoline
(6) 7-benzylsulphonamido-1,2,3,4-tetrahydro-quinoline
   $R_f$ value: 0.72 (silica gel; ethyl acetate)
(7) 5-phenylsulphonamido-1,2,3,4-tetrahydro-quinoline
   $R_f$ value: 0.82 (silica gel; ethyl acetate)
(8) 7-phenylsulphonamido-1,2,3,4-tetrahydro-quinoline
   $R_f$ value: 0.83 (silica gel; ethyl acetate)
(9) 6-phenylacetylamino-1,2,3,4-tetrahydro-quinoline
   Melting point: 116–118° C.
(10) 2-methyl-6-phenylsulphonamido-1,2,3,4-tetrahydro-quinoline
   $R_f$ value: 0.66 (silica gel; toluene/ethyl acetate=6:4)
(11) 6-benzylsulphonamido-1,2,3,4-tetrahydro-quinoline
(12) 6-benzoylamino-1,2,3,4-tetrahydro-quinoline
   Melting point: 150–153° C.
(13) 6-(4-fluoro-phenylsulphonamido)-1,2,3,4-tetrahydro-quinoline
   Melting point: 85° C.
(14) 6-n-butylsulphonamido-1,2,3,4-tetrahydro-quinoline
   $C_{13}H_{20}N_2O_2S$ (268,38)

| | | | | | | |
|---|---|---|---|---|---|---|
| Calc.: | C | 58.18 | H | 7.57 | N | 10.43 |
| Found: | | 57.95 | | 7.70 | | 10.22 |

(15) 6-[N-(2-phenylethyl)-phenylsulphonamido]-1,2,3,4-tetrahydro-quinoline
   $R_f$ value: 0.60 (silica gel; ethyl acetate/petroleum ether= 1:1)
(16) 6[N-(ethoxycarbonylmethyl)-phenylsulphonamido]-1,2,3,4-tetrahydro-quinoline
(17) 6-(4-chloro-phenylsulphonamido)-1,2,3,4-tetrahydro-quinoline
(18) 6-(4-bromo-phenylsulphonamido)-1,2,3,4-tetrahydro-quinoline
(19) 6-(3chloro-phenylsulphonamido)-1,2,3,4-tetrahydro-quinoline
(20) 6-(3-bromo-phenylsulphonamido)-1,2,3,4-tetrahydro-quinoline
(21) 6-(4-methyl-phenylsulphonamido)-1,2,3,4-tetrahydro-quinoline
(22) 6-morpholinocarbonyl-1,2,3,4-tetrahydrochinolin
   Prepared from the compound prepared according to Example VII(6)
   Yield: 96% of theory,
   $R_f$ value: 0.64 (silica gel; ethyl acetate)
(23) 6-piperidinocarbonyl-1,2,3,4-tetrahydrochinolin
   Prepared from the compound prepared according to Example VII Yield: 36% of theory,
   $R_f$ value: 0.57 (silica gel; ethyl acetate)
(24) 6-benzylaminocarbonyl-1,2,3,4-tetrahydroquinoline
   Prepared from the compound prepared according to Example VII(1)
   Yield: 50% of theory,
   $R_f$ value: 0.89 (silica gel; ethyl acetate)
(25) 6-(N-methyl-phenylaminocarbonyl)-1,2,3,4-tetrahydroquinoline
   Prepared from the compound prepared according to Example VII(2)
   Yield: 62% of theory,
   $R_f$ value: 0.84 (silica gel; ethyl acetate)
(26) 6-Diethylaminocarbonyl-1,2,3,4-tetrahydroquinoline
   Yield: 98% of theory,
   Prepared from the compound prepared according to Example VII(3)
   $R_f$ value: 0.60 (silica gel; ethyl acetate)
(27) 6-(3',5'-dimethyl-piperidinocarbonyl)-1,2,3,4-tetrahydroquinoline
   Prepared from the compound prepared according to Example VII(4)
   Yield: 97% of theory,
   $R_f$ value: 0.67 (silica gel; ethyl acetate)
(28) 6-methoxycarbonyl-1,2,3,4-tetrahydroquinoline
   Prepared from methyl quinoline-6-carboxylate (prepared analogously to
   J.Amer.Chem.Soc.68, 2721 (1946))
   Yield: 60% of theory
(29) 6-(4'-methylpiperidinocarbonyl)-1,2,3,4-tetrahydroquinoline
   Prepared from the compound prepared according to Example VII(5)
   Yield: 96% of theory,
   $R_f$ value: 0.67 (silica gel; ethyl acetate)

EXAMPLE V
6-trifluoroacetylamino-quinoline 7.2 g (0.05 mol) of 6-amino-quinoline and 14.2 g (0.11 mol) of N,N-diisopropylethylamine are dissolved in 100 ml methylene chloride. Then 11.55 g (0.055 mol) of trifluoroacetic acid anhydride are added dropwise at about 0° C. and the mixture is stirred at this temperature for 1 hour. The precipitate formed is suction filtered and washed with methylene chloride and water and then dried. The mother liquor is extracted three times with methylene chloride, then the organic phase is separated off, dried over sodium sulphate, concentrated by rotary evaporation and combined with the precipitate obtained above.

Yield: 10.69 g (89.0% of theory),
Melting point: 183–185° C.

EXAMPLE VI
6-trifluoroacetylamino-1,2,3,4-tetrahydro-quinoline 2,4 g (0.01 mol) of 6-trifluoroacetylamino-quinoline are dissolved in 20 ml glacial acetic acid and hydrogenated for I hour with 0.6 g platinum oxide at 3 bar. Then the catalyst is suction filtered and the solution is concentrated by evaporation. The residue is washed with a little sodium hydrogen carbonate solution and dried.

Yield: 1.79 g (74% of theory)
Melting point: 95–97° C.

EXAMPLE VII
6-piperidinocarbonyl-quinoline 3.0 g quinolin-6-carboxylic acid chloride (prepared analogously to J. Med. Chem. 38, 3094–3105 (1995)) are combined with 4.25 ml piperidine in 70 ml pyridine at ambient temperature and stirred for 20 minutes. Then the mixture is concentrated by evaporation, the residue is taken up in a little water and extracted with methylene chloride. The organic phase is concentrated by evaporation and filtered over a silica gel column with ethyl acetate.

Yield: 2.1 g (52% of theory),
$R_f$ value: 0.24 (silica gel; ethyl acetate)
The following are prepared analogously:
(1) 6-benzylaminocarbonyl-quinoline
Yield: 73% of theory,
$R_f$ value: 0.45 (silica gel; ethyl acetate)
(2) 6-(N-methyl-phenylaminocarbonyl)-quinoline
Yield: 83% of theory,
$R_f$ value: 0.49 (silica gel; ethyl acetate)
(3) 6-diethylaminocarbonyl-quinoline
Yield: 72% of theory,
$R_f$ value: 0.24 (silica gel; ethyl acetate)
(4) 6-(3',5'-dimethyl-piperidinocarbonyl)-quinoline
Yield: 33% of theory,
$R_f$ value: 0.25 (silica gel; ethyl acetate)
(5) 6-(4'-methylpiperidinocarbonyl)-quinoline
Yield: 50% of theory,
$R_f$ value: 0.21 (silica gel; ethyl acetate)
(6) 6-morpholinocarbonyl-quinoline
Yield: 69% of theory,
$R_f$ value: 0.22 (silica gel; ethyl acetate)

Preparation of the Compounds of General Formula I

EXAMPLE 1
1-[3-(4-cyano-phenyl)propionyl]-5-nitro-2,3-dihydro-indole 1.6 g of 5-nitro-2,3-dihydro-indole are dissolved in 40 ml methylene chloride, then combined with 1.5 ml of triethylamine and then with 1.93 g of 3-(4cyano-phenyl)propionic acid chloride in 4 ml methylene chloride. After being stirred overnight, the mixture is concentrated to dryness by evaporation. The product (3 g, 93% of theory) is processed without any further purification.

The following are prepared analogously:
(1) 1-[3-(4-cyanophenyl)propionyl]-3-methyl-6-phenylsulphon-amido1,2,3,4-tetrahydro-quinoline
Yield: 94% of theory,
$R_f$ value: 0.67 (silica gel; toluene/ethyl acetate=6:4)
(2) 1-[3-(4-cyano-phenyl)propionyl]-2,3,4,5-tetrahydro-benzo[b]azepine
Yield: 82% of theory,
$R_f$ value: 0.55 (silica gel; toluene/ethyl acetate=7:3)
(3) 1-[3-(4-cyanophenyl)propionyl]4-methyl-6-nitro-tetrahydro-quinoline
Prepared from 3-(4cyano-phenyl)propionylchloride and 4-methyl-6-nitro-tetrahydro-quinoline
Yield: 55% of theory,
$R_f$ value: 0.45 (silica gel; toluene/ethyl acetate=9:1)

EXAMPLE 2
5-amino-1-[3-(4-cyano-phenyl)propionyl]-2,3-dihydro-indole 2 g 1-[3-(4-cyano-phenyl)propionyl]-5-nitro-2,3-dihydro-indole are dissolved in 100 ml of methanol/methylene chloride and hydrogenated at 3 bar over palladium/charcoal. Then the mixture is concentrated by evaporation.

Yield: 2 g (74% of theory),
$R_f$ value: 0.20 (silica gel; toluene/ethyl acetate=6:4)
The following are prepared analogously:
(1) 6-amino-1-[3-(4-cyano-phenyl)propionyl]-3-methyl-1,2,3,4-tetrahydro-quinoline
Prepared from the compound prepared according to Example 3(1)
Yield: 60% of theory,
$R_f$ value: 0.35 (silica gel; toluene/ethyl acetate=8:2)
(2) 7-amino-1-[3-(4-cyano-phenyl)-propionyl]-2,3,4,5-tetrahydro-1H-benzo[b]azepine
Prepared from the compound prepared according to Example 3
Yield: 74% of theory,
$R_f$ value: 0.13 (silica gel; toluene/ethyl acetate=7:3)
(3) 6-amino-1-[3-(4-cyano-phenyl)propionyl]4methyl-1,2,3,4-tetrahydro-quinoline
Yield: 75% of theory,
Melting point: sinters from 80° C.
(4) 1-[3-(2-amino-4-cyanophenyl)propionyl]-6-phenylsulphonylamino-1,2,3,4-tetrahydro-quinoline
Prepared from the compound prepared according to Example 9(28)
Yield: 67% of theory,
$R_f$ value: 0.58 (silica gel; methylene chloride/methanol=4:1)

EXAMPLE 3
1-[3-(4-cyano-phenyl)propionyl]-7-nitro-2,3,4,5-tetrahydro-1H-benzo[b]azepine 3 g 1-[3-(4-cyano-phenyl)propionyl]-2,3,4,5-tetrahydro-1H-benzo[b]azepine (see Example 1(2)) are dissolved in 17 ml glacial acetic acid and stirred with 1 ml of nitric acid in 3 ml of glacial acetic acid overnight at ambient temperature. Then the mixture is concentrated by evaporation and the residue is taken up in water and extracted 3 times with methylene chloride. The organic phase is dried, concentrated by evaporation and the residue is chromatographed over a silica gel column with toluene/ethyl acetate=8:2.

Yield: 1.2 g (35% of theory),
Melting point: from 127° C.
The following is prepared analogously:
(1) 1-[3-(4-cyano-phenyl)propionyl]-3-methyl-6-nitro-1,2,3,4-tetrahydro-quinoline Yield: 85% of theory,
R$_f$ value: 0.72 (silica gel; toluene/ethyl acetate=8:2)

EXAMPLE 4

1-[3-(4-cyano-phenyl)propionyl]-6-trifluoroacetylamino-1,2,3,4-tetrahydro-quinoline 10 g (0.057 mol) of 3-(4-cyano-phenyl)propionic acid and 6.6 g (0.065 mol) of N-methyl-morpholine are dissolved in 250 ml tetrahydrofuran and cooled to −20° C. Then 8.2 g (0.06 mol) of isobutyl chloroformate are added dropwise. 13.9 g (0.057 mol) of 6-(trifluoroacetylamino)-1,2,3,4-tetrahydro-quinoline in 200 ml tetrahydrofuran are then added and the solution is left to heat up to ambient temperature overnight. It is then diluted with 200 ml of ethyl acetate and washed with 2×80 ml of 0.5 N hydrochloric acid and then 100 ml of sodium hydrogen carbonate solution. The organic phase is dried over sodium sulphate and concentrated by evaporation in vacuo.

Yield: 16 g (70% of theory),
Melting point: 151–152° C.
$C_{21}H_{18}F_3N_3O_2$ (401.39)

| Calc.: | C | 62.83 | H | 4.51 | N | 10.46 |
|---|---|---|---|---|---|---|
| Found: | | 62.45 | | 4.55 | | 10.44 |

EXAMPLE 5

6-amino-1-[3-(4-cyano-phenyl)propionyl]-1,2,3,4-tetrahydro-quinoline 16 g of 1-[3-(4cyano-phenyl)propionyl]-6-trifluoracetylamino-1,2,3,4-tetrahydro-quinoline are dissolved in 70 ml of methanol and 50 ml of dioxan and stirred with 200 ml of 1N sodium hydroxide solution for 2 hours at 40° C. Then the mixture is extracted with methylene chloride, the organic phase is dried over sodium sulphate and concentrated by evaporation.

Yield: 10.7 g (88% of theory),
Melting point 180–200° C.
$C_{19}H_{19}N_3O$ (305.38)

| Calc.: | C | 74.72 | H | 6.27 | N | 13.75 |
|---|---|---|---|---|---|---|
| Found: | | 74.41 | | 6.37 | | 13.56 |

EXAMPLE 6

6-(N-ethoxycarbonylmethyl-amino)-1-[3-(4-cyano-phenyl)-propionyl]-1,2,3,4-tetrahydro-quinoline 10.7 g (35 mmol) of 6-amino-1-[3-(4cyano-phenyl)-propionyl]-1,2,3,4-tetrahydro-quinoline are dissolved with 9.2 ml (53 mmol) of N-ethyl-diisopropylamine in 70 ml of dimethylformamide and 9 g (42 mmol) of ethyl iodoacetate are added whilst cooling with ice. The solution is stirred overnight and then poured onto water, extracted with ethyl acetate and the organic phase is concentrated by rotary evaporation.

Yield: 12.7 g (92% of theory),
Melting point: 117–119° C.

The following are prepared analogously:

(1) 6-(N-ethoxycarbonylmethyl-benzylamino)-1-[3-(4-cyano-phenyl)-propionyl]-1,2,3,4-tetrahydro-quinoline Prepared from 6benzylamino-1-[3-(4cyano-phenyl)-propionyl]-1,2,3,4-tetrahydro-quinoline (see Example 14) and ethyl iodoacetate
Yield: 91% of theory, R$_f$ value: 0.36 (silica gel; methylene chloride/ethyl acetate 19:1)

(2) 6-[N-ethoxycarbonylmethyl-(naphthalin-2-ylmethyl)-amino]-1-[3-(4-cyano-phenyl)-propionyl]-1,2,3,4-tetrahydro-quinoline Prepared from 6-[(naphthalin-2-ylmethyl)-amino]-1-[3-(4-cyano-phenyl)-propionyl]-1,2,3,4-tetrahydro-quinoline (see Example 14(2)) and ethyl iodoacetate
Melting point: oil
Yield: 93% of theory, (3) 6-[N-ethoxycarbonylmethyl-(naphthalin-1-ylmethyl)-amino]-1-[3-(4-cyano-phenyl)-propionyl]-1,2,3,4-tetrahydro-quinoline Prepared from 6-[(naphthalin-1-ylmethyl)-amino]-1-[3-(4-cyano-phenyl)-propionyl]-1,2,3,4-tetrahydro-quinoline (see Example 14(1)) and ethyl iodoacetate
Melting point: 80° C.
Yield: 96% of theory, (4) 1-[3-(4-cyano-phenyl)-propionyl]-6-(N-ethoxycarbonylmethyl-2,2-diphenyl-ethylamino)-1,2,3,4-tetrahydro-quinoline Prepared from 1-[3-(4-cyano-phenyl)-propionyl]-6-(2,2-diphenyl-ethylamino)-1,2,3,4-tetrahydro-quinoline (see Example 14(4)) and ethyl iodoacetate
Yield: 93% of theory,
Melting point: 156–158° C.

EXAMPLE 7

1-[3-(4-cyano-phenyl)-propionyl]-6-[N-ethoxycarbonylmethyl-(isoquinoline-5-sulphonyl)-amino]-1,2,3,4-tetrahydro-quinoline 2.8 g 1-[3-(4-cyano-phenyl)-propionyl]-6-(isoquinoline-5-sulphonamido)-1,2,3,4-tetrahydro-quinoline (see Example 10(14)) are dissolved in 40 ml of dimethylsulphoxide, combined with 670 mg of potassium tert. butoxide and stirred for 1 hour at ambient temperature. Then 1.0 g ethyl bromoacetate are added and the solution is stirred overnight. It is then poured onto ice water, extracted 3× with ethyl acetate and the organic phase is dried and concentrated by rotary evaporation.

Yield: 2.1 g (64% of theory),
Melting point: 116–117° C.

The following are prepared analogously:

(1) 1-[3-(4-cyano-phenyl)-propionyl]-6-(N-ethoxycarbonylmethyl-n-butylsulphonylamino)-1,2,3,4-tetrahydro-quinoline Prepared from the compound prepared according to Example 9(4)
Yield: 77% of theory,
Melting point: oil (2) 1-[(4-cyano-phenoxy)-acetyl]-6-(N-ethoxycarbonylmethyl-1-naphthalinsulphonylamido)-1,2,3,4-tetrahydro-quinoline Prepared from the compound prepared according to Example 9(27)
Yield: 77% of theory,
$C_{32}H_{29}N_3O_6S$ (583.61)

| Calc.: | C | 65.85 | H | 5.00 | N | 7.19 |
|---|---|---|---|---|---|---|
| Found: | | 65.31 | | 5.15 | | 7.02 |

(3) 6-[N-(3-methoxycarbonylpropyl)-naphth-1-yl-sulphonylamido]-1-[3-(4-benzyloxycarbonylamidino-phenyl)-propionyl]-1,2,3,4-tetrahydro-quinoline Prepared from 6-(naphth-1-yl-sulphonylamido)-1-[3-(4-benzyloxycarbonylamidino-phenyl)-propionyl]-1,2,3,4-tetrahydro-quinoline (see Example 32) and methyl 4-bromobutyrate Yield: 79% of theory, (4) 6-[N-(2-ethoxycarbonylethyl)-naphth-1-yl-sulphonylamido]-1-[3-(4-benzyloxycarbonylamidino-phenyl)-propionyl]-1,2,3,4-tetrahydro-quinoline Prepared from 6-(naphth-1-yl-sulphonylamido)-1-[3-(4-benzyloxycarbonylamidino-phenyl)-propionyl]-1,2,3,4-tetrahydro-quinoline (see Example 32) and ethyl 2-bromopropionate Yield: 72% of theory, $R_f$ value: 0.24 (silica gel; methylene chloride/ethyl acetate=8:2)

(5) 6-[N-methyl-(naphth-1-yl-sulphonyl)-amido]-1-[3-(4-benzyloxycarbonylamidino-phenyl)-propionyl]-1,2,3,4-tetrahydro-quinoline Prepared from 6-[(naphth-1-yl-sulphonyl)-amido]-1-[3-(4-benzyloxycarbonylamidino-phenyl)-propionyl]-1,2,3,4-tetrahydro-quinoline and methyliodide Yield: 68% of theory, $R_f$ value: 0.57 (silica gel; methylene chloride/ethyl acetate=7:3)

(6) 6-[N-benzyl-(naphth-1-yl-sulphonyl)amido]-1-[3-(4-benzyloxycarbonylamidino-phenyl)-propionyl]-1,2,3,4-tetrahydro-quinoline Prepared from 6-[(naphth-1-yl-sulphonyl)-amido]-1-[3-(4-benzyloxycarbonylamidino-phenyl)-propionyl]-1,2,3,4-tetrahydro-quinoline and benzylbromide Yield: 72% of theory, $R_f$ value: 0.44 (silica gel; methylene chloride/ethyl acetate=7:3)

(7) 6-[N-ethoxycarbonylmethyl-(naphth-1-yl-sulphonyl)-amido]-1-[3-(4-benzyloxycarbonylamidino-phenyl)-propionyl]-1,2,3,4-tetrahydro-quinoline Prepared from 6-[(naphth-1-yl-sulphonyl)-amido]-1-[3-(4-benzyloxycarbonylamidino-phenyl)-propionyl]-1,2,3,4-tetrahydro-quinoline and ethyl bromoacetate Yield: 83% of theory, (8) 1-[3-(4-benzyloxycarbonylamidino-phenyl)-propionyl]-6-[N-(naphth-1-yl-sulphonyl)-N,N-(di(methoxycarbonylmethyl)-aminocarbonylmethyl)-amino]-1,2,3,4-tetrahydro-quinoline Prepared from the compound prepared according to Example 32 and methyl bromoacetylmethoxycarbonylmethylamino-acetate Yield: 59% of theory, $R_f$ value: 0.27 (silica gel; ethyl acetate/petroleum ether=4:1)

EXAMPLE 8

1-[3-(4-cyanophenyl)-propionyl]-6-methylamino-1,2,3,4-tetrahydro-quinoline 10.5 g (34 mmol) of 1-(3-cyanophenyl-propionyl)-6-amino-1,2,3,4-tetrahydro-quinoline are boiled with 40 ml of triethyl orthoformate and 1 ml of trifluoro-acetic acid for 6 hours and then concentrated by rotary evaporation. The residue is taken up in 50 ml of ethanol and at 0° C. 1.45 g of sodium cyanoborohydride is added in batches. This solution is left overnight at ambient temperature with stirring and then refluxed for 4 hours. Finally, it is diluted with ice water and made acidic with hydrochloric acid. Then it is neutralised with ammonia, extracted with methylene chloride, the organic phase is dried and evaporated down. The residue is chromatographed over silica gel with methylene chloride/ethyl acetate 8:2.

Yield: 5.4 g (49% of theory),
Melting point: 120° C.
$C_{20}H_{21}N_3O$ (319.40)

| | | | | | | | |
|---|---|---|---|---|---|---|---|
| Calc.: | C | 75.20 | H | 6.62 | N | 13.15 | |
| Found: | | 75.02 | | 6.73 | | 12.98 | |

EXAMPLE 9

1-[3-(4-cyano-phenyl)propionyl]-6-phenylsulphonamido-1,2,3,4-tetrahydro-quinoline 4.6 g 3-(4-cyano-phenylpropionic acid are dissolved with 2.8 g of N-methyl-morpholine in 120 ml of tetrahydrofuran and cooled to −35° C. To this solution are added 3.6 ml of isobutyl chloroformate, stirring is continued for half an hour and then at −40° C. 7.2 g of 6-phenylsulphonamido-1,2,3,4-tetrahydro-quinoline are added (see Example IV). After 2 hours the solution is slowly allowed to come back to ambient temperature and stirring is continued overnight. Then it is concentrated by evaporation and the residue is taken up in ethyl acetate and water. The organic phase is again washed with water, dried and concentrated by evaporation. The oil remaining is chromatographed over a silica gel column with ethyl acetate/petroleum ether (7:3).

Yield: 10.3 g (92.4% of theory),
Melting point: 87–89° C.
$C_{25}H_{23}N_3O_3S$ (445.54)

| | | | | | | | |
|---|---|---|---|---|---|---|---|
| Calc.: | C | 67.40 | H | 5.20 | N | 9.43 | S | 7.20 |
| Found: | | 67.47 | | 5.61 | | 9.09 | | 7.38 |

The following are prepared analogously:

(1) 1-[3-(4-cyano-phenyl)propionyl]-6-(2-naphthyl-sulphonamido)-1,2,3,4-tetrahydro-quinoline Prepared from the compound prepared according to Example IV(1)

Yield: 68% of theory,
Melting point: 70° C.
$C_{29}H_{25}N_3O_3S$ (495.60)

| | | | | | | |
|---|---|---|---|---|---|---|
| Calc.: | C | 70.28 | H | 5.08 | N | 8.48 |
| Found: | | 70.42 | | 5.30 | | 8.21 |

(2) 1-[3-(4-cyano-phenyl)propionyl]-6-(1-naphthyl-sulphonamido)-1,2,3,4-tetrahydro-quinoline Prepared from the compound prepared according to Example IV(2)

Yield: 14% of theory,
$R_f$ value: 0.56 (silica gel; toluene/ethyl acetate=1:1)

(3) 1-[3-(4-cyano-phenyl)propionyl]-6-(4-fluoro-phenyl-sulphonamido)-1,2,3,4-tetrahydro-quinoline Prepared from the compound prepared according to Example IV(3)

Yield: 64% of theory,
Melting point: 62–64° C.
$C_{25}H_{22}FN_3O_3S$ (463.53)

| | | | | | | |
|---|---|---|---|---|---|---|
| Calc.: | C | 64.78 | H | 4.78 | N | 9.07 |
| Found: | | 65.00 | | 5.16 | | 8.73 |

(4) 6-(n-butylsulphonamido)-1-[3-(4-cyano-phenyl)propionyl]-1,2,3,4-tetrahydro-quinoline Prepared from the compound prepared according to Example IV(4)
Yield: 53% of theory,
Melting point: 138–140° C.
(5) 1-[3-(4-cyano-phenyl)propionyl]-5-phenylsulphonamido-1,2,3,4-tetrahydro-quinoline
Prepared from the compound prepared according to Example IV(7)
$R_f$ value: 0.32 (silica gel; toluene/ethyl acetate=6:4)
(6) 1-[3-(4-cyano-phenyl)propionyl]-7-phenylsulphonamido-1,2,3,4-tetrahydro-quinoline
Prepared from the compound prepared according to Example IV(8)
Melting point: 74–76° C.
(7) 7-benzylsulphonamido-1-[3-(4-cyano-phenyl)propionyl]-1,2,3,4-tetrahydro-quinoline
Prepared from the compound prepared according to Example IV(6)
Melting point: 177–180° C.
(8) 1-[3-(4-cyanophenyl)propionyl]-6-(N-methyl-phenylsulphonamido)-1,2,3,4-tetrahydro-quinoline
Prepared from the compound prepared according to Example IV(5)
Yield:. 74% of theory,
Melting point: 114–116° C.
$C_{26}H_{25}N_3O_3S$ (459.57)

| Calc.: | C | 67.95 | H | 5.48 | N | 9.14 | S | 6.98 |
|---|---|---|---|---|---|---|---|---|
| Found: | | 68.02 | | 5.56 | | 9.25 | | 7.04 |

(9) 1-[3-(4-cyano-phenyl)propionyl]-6-phenylacetylamino-1,2,3,4-tetrahydro-quinoline
Prepared from the compound prepared according to Example IV(9)
Yield: 81% of theory,
(10) 1-[3-(4-cyano-phenyl)propionyl]-6-[N-(ethoxycarbonylmethyl)-phenylsulphonamido]-1,2,3,4-tetrahydro-quinoline
Prepared from the compound prepared according to Example 6
Melting point: 148–150° C.
$C_{29}H_{29}N_3O_5S$ (531.65)

| Calc.: | C | 65.52 | H | 5.50 | N | 7.90 | S | 6.03 |
|---|---|---|---|---|---|---|---|---|
| Found: | | 65.34 | | 5.54 | | 7.86 | | 6.03 |

(11) 1-[3-(4-cyano-phenyl)propionyl]-6-[N-(2-phenylethyl)-phenylsulphonamido]-1,2,3,4-tetrahydro-quinoline
Prepared from the compound prepared according to Example IV(15)
(12) 6-benzylsulphonamido-1-[3-(4-cyano-phenyl)propionyl]-1,2,3,4-tetrahydro-quinoline
Prepared from the compound prepared according to Example IV(11)
Melting point: 161–163° C.
$C_{26}H_{25}N_3O_3S$ (459.57)

| Calc.: | C | 67.95 | H | 5.48 | N | 9.14 |
|---|---|---|---|---|---|---|
| Found: | | 67.93 | | 5.56 | | 9.07 |

(13) 6-benzoylamino-1-[3-(4-cyano-phenyl)propionyl]-1,2,3,4-tetrahydro-quinoline
Prepared from the compound prepared according to Example IV(12)
Yield: 83% of theory,
$C_{26}H_{23}N_3O_3$ (409.49)

| Calc.: | C | 76.26 | H | 5.66 | N | 10.26 |
|---|---|---|---|---|---|---|
| Found: | | 76.17 | | 5.85 | | 10.19 |

(14) 1-[3-(4-cyano-phenyl)propionyl]-2-methyl-6-phenyl-sulphonamido-1,2,3,4-tetrahydro-quinoline
Prepared from the compound prepared according to Example IV(10)
Yield: 41% of theory,
(15) 1-[3-(4-cyano-phenyl)propionyl]-6-(4-chloro-phenylsulphonamido)-1,2,3,4-tetrahydro-quinoline
Prepared from the compound prepared according to Example IV(17)
(16) 1-[3-(4-cyano-phenyl)propionyl]-6-(4-bromo-phenyl-sulphonamido)-1,2,3,4-tetrahydro-quinoline
Prepared from the compound prepared according to Example IV(18)
(17) 1-[3-(4cyano-phenyl)propionyl]-6-(3-chloro-phenylsulphonamido)-1,2,3,4-tetrahydro-quinoline
Prepared from the compound prepared according to Example IV(19)
(18) 1-[3-(4-cyano-phenyl)propionyl]-6-(3-bromophenyl-sulphonamido)-1,2,3,4-tetrahydro-quinoline
Prepared from the compound prepared according to Example IV(20)
(19) 1-[3-(4cyano-phenyl)propionyl]-6-(4-methyl-phenylsulphonamido)-1,2,3,4-tetrahydro-quinoline
Prepared from the compound prepared according to Example IV(21)
(20) 1-[3-(4-cyano-phenyl)propionyl]-6-(4-methoxy-phenylsulphonamido)-1,2,3,4-tetrahydro-quinoline
Prepared from the compound prepared according to Example IV(22)
(21) 1-[3-(4-cyano-phenyl)propionyl]-6-[-(2-phenylethyl)-phenylsulphonamido]-1,2,3,4-tetrahydro-quinoline
Prepared from the compound prepared according to Example IV(11)
Yield: 69% of theory,
(22) 1-[3-(4-cyano-phenyl)-propionyl]-6-(4-methyl-piperidino-carbonyl)-1,2,3,4-tetrahydro-quinoline
Prepared from the compound prepared according to Example IV(29)
Yield: 67% of theory
$R_f$ value: 0.73 (silica gel; methylene chloride/ethyl acetate=8:2)
(23) 1-[3-(4-cyano-phenyl)-propionyl]-6-(morpholinocarbonyl)-1,2,3,4-tetrahydro-quinoline
Prepared from the compound prepared according to Example IV(22)
Yield: 37% of theory
$R_f$ value: 0.61 (silica gel; methylene chloride/ethyl acetate=8:2)
(24) 1-[3-(3-cyanophenyl)propionyl)-6-phenylsulphonamido-1,2,3,4-tetrahydro-quinoline
Prepared from the compound prepared according to Example IV
Yield: 78% of theory
Melting point: 130–133° C.
(25) 1-[2-(4-cyano-phenyloxy)-acetyl]-6-phenylsulphonamido-1,2,3,4-tetrahydro-quinoline
Prepared from the compound prepared according to Example IV and 4-cyano-phenoxyacetic acid Yield: 68% of theory
Melting point: 76–78° C.
(26) 1-[2-((4-cyano-phenyl)-methylamino)-acetyl]-6-benzolsulphonamido-1,2,3,4-tetrahydro-quinoline
Prepared from the compound prepared according to Example IV
Yield: 82% of theory
Melting point: 193–194° C.
(27) 1-[2-(4-cyano-phenyloxy)-acetyl]-6-(1-naphthyl-sulphonamido)-1,2,3,4-tetrahydro-quinoline
Prepared from the compound prepared according to Example IV(2)
Yield: 41% of theory
(28) 1-[3-(4-cyano-2-nitro-phenyl)-propionyl]-6-phenyl-sulphonylamido-1,2,3,4-tetrahydro-quinoline
$R_f$ value: 0.56 (silica gel; methylene chloride/methanol=9:1)
(29) 1-(4-cyano-benzoyl)-6phenylsulphonamido-1,2,3,4-tetrahydro-quinoline
Prepared from the compound prepared according to Example IV and 4-cyano-benzoic acid
Yield: 71% of theory,
Melting point: 132–134° C.
(30) 1-[3-(4cyano-3-methyl-phenyl)-propionyl]-6-phenylsulphonamido-1,2,3,4-tetrahydro-quinoline
Prepared from the compound prepared according to Example IV and 4-cyano-3-methyl-phenylpropionic acid
$R_f$ value: 0.40 (silica gel; methylene chloride/ethanol=40:1)
(31) 1-[3-(4-cyano-3-fluoro-phenyl)-propionyl]-6-phenylsulphonamido-1,2,3,4-tetrahydro-quinoline
Prepared from the compound prepared according to Example IV and 4-cyano-3-fluorophenylpropionic acid
Yield: 36% of theory,
Melting point: 138–140° C.
(32) 1-[3-(2-cyano-pyridine-5-yl)-propionyl]-6-phenyl-sulphonamido-1,2,3,4-tetrahydro-quinoline
Prepared from the compound prepared according to Example IV
Yield: 73% of theory,
$R_f$ value: 0.35 (silica gel; methylene chloride/methanol=40:1)
(33) 1-3-(4-cyano-phenyl)-acryloyl]-6-phenylsulphonamido-1,2,3,4-tetrahydro-quinoline
Yield: 74% of theory,
Melting point: 175–180° C.
(34) 1-[3-(4-cyano-phenyl)-propionyl]-6-piperidinocarbonyl-1,2,3,4-tetrahydro-quinoline
Prepared from the compound prepared according to Example IV(23)
Yield: 97% of theory,
$R_f$ value: 0.38 (silica gel; ethyl acetate)
(35) 1-[3-(4-cyano-phenyl)-propionyl]-6-benzylamidocarbonyl-1,2,3,4-tetrahydro-quinoline
Prepared from the compound prepared according to Example IV(24)
Yield: 60% of theory,
$R_f$ value: 0.24 (silica gel; toluene/ethyl acetate=4:6)
(36) 1-[3-(4-cyanophenyl)-propionyl]-6N-methyl-phenyl-aminocarbonyl)-1,2,3,4-tetrahydro-quinoline
Prepared from the compound prepared according to Example IV(25)
Yield: 82% of theory,
$R_f$ value: 0.72 (silica gel; ethyl acetate)
(37) 1-[3-(4cyano-phenyl)-propionyl]-6-(diethylamino-carbonyl)-1,2,3,4-tetrahydro-quinoline
Prepared from the compound prepared according to Example IV(26)
Yield: 55% of theory,
$R_f$ value: 0.21 (silica gel; methylene chloride/ethyl acetate=8:2)
(38) 1-[3-(4-cyano-phenyl)-propionyl]-6-(3,5-dimethyl-piperidinocarbonyl)-1,2,3,4-tetrahydro-quinoline
Prepared from the compound prepared according to Example IV(27)
Yield: 96% of theory,
$R_f$ value: 0.14 (silica gel; methylene chloride/ethyl acetate=8:2)
(39) 1-[3-(4-cyano-phenyl)-propionyl]-6-methoxycarbonyl-1,2,3,4-tetrahydro-quinoline
Prepared from methyl 1,2,3,4-tetrahydroquinoline-6-carboxylate
Yield: 65% of theory

EXAMPLE 10

1-[3-(4-cyano-phenyl)propionyl]-6-(4-amino-3,5-dichloro-phenyl-sulphonamido)-1,2,3,4-tetrahydro-quinoline 1.0 g 6-amino-1-[3-(4-cyano-phenyl)propionyl]-1,2,3,4-tetrahydro-quinoline (see Example, 5) are dissolved in 8 ml of pyridine, combined with 1 g of 4-amino-3,5-dichloro-phenylsulphonic acid chloride in batches and then heated for 40 minutes to 100° C. Then the solvent is eliminated, the residue is triturated with 1N hydrochloric acid and extracted with methylene chloride. The organic phase is dried over sodium sulphate and concentrated by evaporation.

Yield: 1.5 g (86% of theory),
Melting point: 183–184° C.
$C_{25}H_{22}N_4Cl_2O_3S$ (529.45)

| Calc.: | C | 56.72 | H | 4.19 | N | 10.58 |
|---|---|---|---|---|---|---|
| Found: | | 56.54 | | 4.25 | | 10.44 |

The following are prepared analogously:
(1) 1-[3-(4-cyano-phenyl)propionyl]-6-(5-dimethylamino-naphtho-1-yl-sulphonamido)-1,2,3,4-tetrahydro-quinoline
Prepared from the compound prepared according to Example 5
Yield: 95% of theory,
Melting point: 78–80° C.
$C_{31}H_{30}N_4O_3S$ (538.67)

| Calc.: | C69.12 | H5.61 | N10.43 |
|---|---|---|---|
| Found: | 70.11 | 5.82 | 9.79 |

(2) 1-[3-(4-cyano-phenyl)propionyl]-6-propylsulphonamido-1,2,3,4-tetrahydro-quinoline
Prepared from the compound prepared according to Example 5
Yield: 95% of theory,
Melting point: 152–153° C.
$C_{22}H_{25}N_3O_3S$ (411.52)

| Calc.: | C64.21 | H6.12 | N10.21 |
|---|---|---|---|
| Found: | 64.05 | 6.10 | 10.02 |

(3) 6-(5-chloro-thien-2-yl-sulphonamido)-1-[3-(4-cyano-phenyl)propionyl]-1,2,3,4-tetrahydro-quinoline
Prepared from the compound prepared according to Example 5

Yield: 69% of theory,
Melting point: 153–154° C.
$C_{23}H_{20}ClN_3O_3S_2$ (486.01)

| Calc.: | C56.84 | H4.14 | N8.64 | Cl7.29 |
|---|---|---|---|---|
| Found: | 56.88 | 4.24 | 8.24 | 7.08 |

(4) 1-[3-(4-cyano-phenyl)propionyl]-6isopropylsulphonamido-1,2,3,4-tetrahydro-quinoline
Prepared from the compound prepared according to Example 5
Yield: 37% of theory,
Melting point: 151–152° C.
$C_{22}H_{25}N_3O_3S$ (411.52)

| Calc.: | C64.21 | H6.12 | N10.21 |
|---|---|---|---|
| Found: | 64.70 | 6.25 | 9.89 |

(5) 6-(3-chloro-propylsulphonamido)-1-[3-(4-cyano-phenyl)propionyl]-1,2,3,4-tetrahydro-quinoline
Prepared from the compound prepared according to Example 5
Yield: 55% of theory,
$C_{22}H_{24}ClN_3O_3S$ (445.97)

| Calc.: | C59.25 | H5.42 | N9.42 | Cl7.95 |
|---|---|---|---|---|
| Found: | 58.68 | 5.44 | 9.26 | 8.32 |

(6) 1-[3-(4-cyano-phenyl)propionyl]-5-phenylsulphonamido-2,3-dihydro-indole
Prepared from the compound prepared according to Example 2
Yield: 78% of theory,
$R_f$ value: 0.46 (silica gel; toluene/ethyl acetate=6:4)
(7) 1-[3-(4-cyano-phenyl)propionyl]-7-phenylsulphonamido-2,3,4,5-tetrahydro-1H-benzo[b]azepine
Prepared from the compound prepared according to Example 2(2)
Yield: 57% of theory,
Melting point: from 148° C.
$R_f$ value: 0.30 (silica gel; toluene/ethyl acetate=13:7)
(8) 1-[3-(4-cyano-phenyl)propionyl]-3-methyl-6-phenyl-sulphonamido-1,2,3,4-tetrahydro-quinoline
Prepared from the compound prepared according to Example 2(1)
Yield: 79% of theory,
$R_f$ value: 0.35 (silica gel; toluene/ethyl acetate=7:3)
(9) 1-[3-(4-cyano-phenyl)propionyl]-4-methyl-6-phenyl-sulphonamido-1,2,3,4-tetrahydro-quinoline
Prepared from the compound prepared according to Example 2(3)
Yield: 89% of theory,
$R_f$ value: 0.21 (silica gel; toluene/ethyl acetate=7:3)
(10) 1-[3-(4cyano-phenyl)propionyl]-6-(3-trifluoromethyl-phenylsulphonamido)-1,2,3,4-tetrahydro-quinoline
Prepared from the compound prepared according to Example 5
Yield: 72% of theory,
$R_f$ value: 0.55 (silica gel; methylene chloride/ethanol=4:1)
(11) 1-[3-(4-cyano-phenyl)-propionyl]-6-(2,5-dichloro-phenylsulphonamido)-1,2,3,4-tetrahydro-quinoline Yield: 89% of theory,
Melting point: 219–220° C.
$C_{25}H_{21}Cl_2N_3O_3S$ (514.43)

| Calc.: | C58.37 | H4.11 | N8.17 |
|---|---|---|---|
| Found: | 58.10 | 4.33 | 8.05 |

(12) 1-[3-(4-cyano-phenyl)-propionyl]-6-(2,3,5,6-tetramethyl-phenylsulphonamido)-1,2,3,4-tetrahydro-quinoline
Prepared from the compound prepared according to Example 5
Yield: 89% of theory,
Melting point: 228° C.
(13) 1-[3-(4-cyano-phenyl)-propionyl]-6-(2,4,6-trimethyl-phenylsulphonamido)-1,2,3,4-tetrahydro-quinoline
Prepared from the compound prepared according to Example 5
Yield: 86% of theory,
Melting point: 182° C.
$C_{28}H_{29}N_3O_3S$ (501.65)

| Calc.: | C68.97 | H5.99 | N8.62 |
|---|---|---|---|
| Found: | 68.91 | 6.08 | 8.68 |

(14) 1-[3-(4-cyano-phenyl)-propionyl]-6-(isoquinoline-5-yl-sulphonamido)-1,2,3,4-tetrahydro-quinoline
Prepared from the compound prepared according to Example 5
Yield: 89% of theory,
Melting point: 210–211° C.
$R_f$ value: 0.46 (silica gel; methylene chloride/ethanol= 20:1)
(15) 1-[3-(4-cyanophenyl)-propionyl]-6-(cyclopropyl-sulphonamido)-1,2,3,4-tetrahydro-quinoline
Prepared from the compound prepared according to Example 5
Yield: 74% of theory,
Melting point: 138–139° C.
(16) 1-[3-(4-cyano-phenyl)-propionyl]-6-(benzimidazol:ol-5-yl-sulphonamido)-1,2,3,4-tetrahydro-quinoline
Prepared from the compound prepared according to Example 5
Yield: 36% of theory,
$R_f$ value: 0.29 (silica gel; methylene chloride/ethanol= 20:1)
(17) 1-[3-(4-cyano-phenyl)-propionyl]-6-(cyclohexyl-sulphonamido)-1,2,3,4-tetrahydro-quinoline
Prepared from the compound prepared according to Example 5
Yield: 57% of theory,
Melting point: 159–163° C.
(18) 1-[3-(4-cyano-phenyl)-propionyl]-6-(3-tolylsulphonamido)-1,2,3,4-tetrahydro-quinoline
Prepared from the compound prepared according to Example 5
Yield: 78% of theory,
Melting point: 130° C.

$C_{26}H_{25}N_3O_3S$ (459.57)

| Calc.: | C67.95 | H5.48 | N9.14 |
|---|---|---|---|
| Found: | 67.68 | 5.54 | 8.89 |

(19) 1-[3-(4-cyano-phenyl)-propionyl]-6-(4-methoxy-benzolsulphonamido)-1,2,3,4-tetrahydro-quinoline
Prepared from the compound prepared according to Example 5
Yield: 87% of theory,
Melting point: decomposition from 65° C.
$C_{26}H_{25}N_3O_4S$ (475.57)

| Calc.: | C65.66 | H5.29 | N8.83 |
|---|---|---|---|
| Found: | 65.75 | 5.61 | 8.64 |

(20) 1-[3-(4-cyano-phenyl)-propionyl]-6-(N-ethoxycarbonylmethyl-quinoline-8-sulphonylamido)-1,2,3,4-tetrahydro-quinoline
Prepared from 1-[3-(4cyano-phenyl)-propionyl]-6-(N-ethoxycarbonylmethylamino)-1,2,3,4-tetrahydro-quinoline (see Example 6) and quinolinesulphonic acid chloride
Yield: 57% of theory

(21) 1-[3-(4-cyano-phenyl)-propionyl]-6-[N-ethoxycarbonylmethyl-(2-naphthylsulphonylamido]-1,2,3,4-tetrahydro-quinoline
Prepared from 1-[3-(4-cyano-phenyl)-propionyl]-6-ethoxy-carbonylamino-1,2,3,4-tetrahydro-quinoline (see Example 6) and naphthalene-2-sulphonic acid chloride
Yield: 69% of theory

(22) 1-[3-(4-cyano-phenyl)-propionyl]-6-(N-benzyl-methanesulphonamido)-1,2,3,4-tetrahydro-quinoline
Prepared from the compound prepared according to Example 14 and methanesulphonic acid chloride
Yield: 51% of theory,
$R_f$ value: 0.34 (silica gel; toluene/ethyl acetate 1:1)

(23) 1-[3-(4-cyano-phenyl)-propionyl]-6-[N-(ethoxycarbonyl-methylamino)-phenylmethanesulphonamido]-1,2,3,4-tetrahydro-quinoline
Prepared from the compound prepared according to Example 6 and phenylmethanesulphonic acid chloride
Yield: 78% of theory

EXAMPLE 11

1-[3-(4-cyano-phenyl)-propionyl]-6-(N-benzoyl-ethoxycarbonylmethylamino)-1,2,3,4-tetrahydro-quinoline
1.57 g of 1-[3-(4-cyano-phenyl)-propionyl]-6-(N-ethoxycarbonylmethyl-amino)-1,2,3,4-tetrahydro-quinoline (see Example 6) and 1 g triethylamine are dissolved in 20 ml of methylene chloride and 0.7 g benzoyl chloride are slowly added dropwise whilst cooling with ice. Then the solution is left overnight at ambient temperature with stirring. The solution is then evaporated down, the residue is taken up in water and extracted with ethyl acetate. The organic phase is dried and concentrated by rotary evaporation. The residue is filtered over a silica gel column.
Yield: 1.7 g (85% of theory),
The following are prepared analogously:

(1) 1-[3-(4-cyano-phenyl)-propionyl]-6-[N-ethoxycarbonyl-methyl-(naphtho-1-yl)-amino]-1,2,3,4-tetrahydro-quinoline
Yield: 82% of theory (2) 1-[3-(4-cyano-phenyl)-propionyl]-6-(N-benzoyl-methyl-amino)-1,2,3,4-tetrahydro-quinoline
Prepared from the compound prepared according to Example 8 and benzoyl chloride
Yield: 83% of theory,
$R_f$ value: 0.37 (silica gel; toluene/ethyl acetate=1:1)

(3) 1-[3-(4-cyano-phenyl)-propionyl]-6-[N-(4-chloro-benzoyl)-methylamino]-1,2,3,4-tetrahydro-quinoline
Prepared from the compound prepared according to Example 8 and 4-chlorobenzoylchloride
Yield: 91% of theory,
$C_{27}H_{24}N_3O_2S$ (475.57)

| Calc.: | C70.81 | H5.28 | N9.17 |
|---|---|---|---|
| Found: | 71.52 | 5.51 | 8.50 |

(4) 1-[3-(4-cyano-phenyl)-propionyl]-6-(N-naphtho-1-yl-methyl-amino)-1,2,3,4-tetrahydro-quinoline
Prepared from the compound prepared according to Example 8 and naphthalene-1-carboxylic acid chloride
Yield: 94% of theory,
$C_{31}H_{27}N_3O_2$ (473.57)

| Calc.: | C78.62 | H5.74 | N8.87 |
|---|---|---|---|
| Found: | 78.30 | 6.03 | 8.52 |

(5) 1-[3-(4-cyano-phenyl)-propionyl]-6-(N-naphtho-2-yl-methyl-amino)-1,2,3,4-tetrahydro-quinoline
Prepared from the compound prepared according to Example 8 and naphthalin-2-carboxylic acid chloride
Yield: 93% of theory,
$C_{31}H_{27}N_3O_2$ (473.57)

| Calc.: | C78.62 | H5.74 | N8.87 |
|---|---|---|---|
| Found: | 78.62 | 5.88 | 8.19 |

(6) 1-[3-(4-cyano-phenyl)propionyl]-6-(N-butyryl-methyl-amino)-1,2,3,4-tetrahydro-quinoline
Prepared from the compound prepared according to Example 8 and butyric acid chloride
Yield: 98% of theory,
$C_{24}H_{27}N_3O_2$ (389.49)

| Calc.: | C74.00 | H6.98 | N10.78 |
|---|---|---|---|
| Found: | 74.09 | 7.01 | 10.43 |

(7) 1-[3-(4-cyano-2-acetylamino-phenyl)-propionyl-6-phenylsulphonylamido-1,2,3,4-tetrahydro-quinoline
Prepared from the compound prepared according to Example 2(4) and acetyl chloride
Yield: 90% of theory,
$R_f$ value: 0.58 (silica gel; methylene chloride/methanol=9:1)

(8) 1-[3-(4-cyano-2-(2-ethoxycarbonylethylcarbonylamino)-propionyl]-6-phenylsulphonamido-1,2,3,4-tetrahydro-quinoline
Prepared from the compound prepared according to Example 2(4) and ethyl succinate chloride
$R_f$ value: 0.63 (silica gel; methylene chloride/methanol=9:1)

(9) 1-[3-(4-cyano-phenyl)-propionyl]-6-(N-benzyl-acetylamino)-1,2,3,4-tetrahydro-quinoline Prepared from the compound prepared according to Example 14 and acetyl chloride
Yield: 91% of theory,
$R_f$ value: 0.27 (silica gel; toluene/ethyl acetate=1:1)
(10) 1-[3-(4-cyano-phenyl)-propionyl]-6-(N-benzyl-N-pentanoyl-amino)-1,2,3,4-tetrahydro-quinoline
Prepared from the compound prepared according to Example 14 and valeric chloride
Yield: 83% of theory,
$R_f$ value: 0.57 (silica gel; toluene/ethyl acetate=1:1)
(11) 1-[3-(4-cyano-phenyl)-propionyl]-6-[N-benzyl-N-(2-ethoxy-carbonylethylcarbonyl)-amino]-1,2,3,4-tetrahydro-quinoline
Prepared from the compound prepared according to Example 14 and ethyl succinate chloride
Yield: 86% of theory,
$R_f$ value: 0.19 (silica gel; methylene chloride/ethyl acetate=8:2)
(12) 1-[3-(4-cyano-phenyl)-propionyl]-6-(2-oxo-pyrrolidino)-1,2,3,4-tetrahydro-quinoline
Prepared from 6-amino-1-[3-(4-cyano-phenyl) propionyl]-1,2,3,4-tetrahydro-quinoline and 4-chloro-butyric acid chloride
Yield: 77% of theory,
$R_f$ value: 0.40 (silica gel; ethyl acetate)
(13) 1-[3-(4-cyano-phenyl)-propionyl]-6-(2-oxo-piperidino)-1,2,3,4-tetrahydro-quinoline
Prepared from 6-amino-1-[3-(4-cyano-phenyl) propionyl]-1,2,3,4-tetrahydro-quinoline and 5-chloro-pentanoic acid chloride
Yield: 69% of theory,
$R_f$ value: 0.11 (silica gel; ethyl acetate)

EXAMPLE 12

1-[3-(4-cyano-phenyl)-propionyl]-6-(N-phenyl-butylaminocarbonyl)-1,2,3,4-tetrahydro-quinoline 0.9 g (4 mmol) of 1-[3-(4-cyano-phenyl)-propionyl]-6-methoxycarbonyl-1,2,3,4-tetrahydro-quinoline (see Example 9(39)) are dissolved in 10 ml of dioxan and stirred with 10 ml of 1 N sodium hydroxide solution at 40° C. for 4 hours. Then the solution is neutralised with hydrochloric acid, concentrated by evaporation and the precipitate formed is suction filtered and dried. The product is suspended in 10 ml of thionyl chloride and refluxed for 3 hours. It is then concentrated by evaporation and the residue is taken up in 10 ml of methylene chloride and combined with 0.93 ml of triethylamine and 0.6 g N-phenylbutylamine in a little methylene chloride. After 20 minutes the reaction has ended and the mixture is washed with 10 ml of 1N sodium hydroxide solution and then 10 ml of water. Then the solution is dried and concentrated by rotary evaporation and the residue is chromatographed over a silica gel column with toluene/ethyl acetate (8:2).
Yield: 1.35 g (70% of theory),
$R_f$ value: 0.29 (silica gel; toluene:ethyl acetate=7:3)
The following were prepared analogously:
(1) 1-[3-(4-cyano-phenyl)-propionyl]-6-[N-(4chloro-phenyl)-methylaminocarbonyl]-1,2,3,4-tetrahydro-quinoline
Yield: 75% of theory,
$R_f$ value: 0.19 (silica gel; toluene:ethyl acetate=7:3)
(2) 1-[3-(4-cyano-phenyl)-propionyl]-6-(N-phenyl-ethylaminocarbonyl)-1,2,3,4-tetrahydro-quinoline
Yield: 71% of theory,
$R_f$ value: 0.16 (silica gel; toluene:ethyl acetate=7:3)
(3) 1-[3-(4-cyano-phenyl)-propionyl]-6-(diphenylaminocarbonyl)-1,2,3,4-tetrahydro-quinoline
Yield: 34% of theory,
$R_f$ value: 0.37 (silica gel; toluene:ethyl acetate=7:3)
(4) 1-[3-(4-cyano-phenyl)-propionyl]-6-(N-phenyl-benzylaminocarbonyl)-1,2,3,4-tetrahydro-quinoline
Yield: 29% of theory,
$R_f$ value: 0.31 (silica gel; toluene:ethyl acetate=7:3)
(5) 1-[3-(4-cyano-phenyl)-propionyl]-6-N-methoxycarbonylmethyl-phenylaminocarbonyl)-1,2,3,4-tetrahydro-quinoline
Yield: 66% of theory,
$R_f$ value: 0.18 (silica gel; toluene:ethyl acetate=7:3)
(6) 1-[3-(4-cyano-phenyl)-propionyl]-6-(N-cyclohexyl-methylaminocarbonyl)-1,2,3,4-tetrahydro-quinoline
Yield: 88% of theory,
$R_f$ value: 0.20 (silica gel; toluene:ethyl acetate=7:3)
(7) 1-[3-(4-cyano-phenyl)-propionyl]-6-(N-ethoxycarbonyl-methyl-cyclohexylaminocarbonyl)-1,2,3,4tetrahydro-quinoline
Yield: 34% of theory,
$R_f$ value: 0.13 (silica gel; toluene:ethyl acetate=7:3)
(8) 1-[3-(4-cyano-phenyl)-propionyl]-6-(2-methoxycarbonyl-pyrrolidinocarbonyl)-1,2,3,4-tetrahydro-quinoline
Yield: 62% of theory,
$R_f$ value: 0.12 (silica gel; toluene:ethyl acetate=1:1)
(9) 1-{1-3-(4-cyano-phenyl)-propionyl]-6-(2-methoxycarbonyl-piperidinocarbonyl)-1,2,3,4-tetrahydro-quinoline
Yield: 64% of theory,
$R_f$ value: 0.22 (silica gel; toluene:ethyl acetate=1:1)
(10) 1-{1-[3-(4-cyano-phenyl)-propionyl]-6-(3-ethoxycarbonyl-piperidinocarbonyl)-1,2,3,4-tetrahydro-quinoline
Yield: 75% of theory,
$R_f$ value: 0.18 (silica gel; toluene:ethyl acetate=1:1)
(11) 1-[3-(4-cyano-phenyl)-propionyl]-6-[N-(2-acetylamino-ethyl)-phenylaminocarbonyl]-1,2,3,4-tetrahydro-quinoline
Yield: 67% of theory,
$R_f$ value: 0.27 (silica gel; ethyl acetate: ethanol 19:1)
(12) 1-[3-(4-cyanophenyl)-propionyl]-6-[N-(N-benzyloxycarbonyl-N-phenyl-2-aminoethyl)-aminocarbonyl]-1,2,3,4-tetrahydro-quinoline
Yield: 73% of theory,
$R_f$ value: 0.31 (silica gel; toluene/ethyl acetate=1:1)

EXAMPLE 13

1-[3-(4-cyano-phenyl)-propionyl]-6-[N-(N-phenyl-2-amino-ethyl)-amidocarbonyl]-1,2,3,4-tetrahydro-quinoline
Prepared from 1-[3-(4-cyano-phenyl)-propionyl]-6-[N-(N-benzyl-oxycarbonyl-N-phenyl-2-aminoethyl)-amidocarbonyl]-1,2,3,4-tetrahydro-quinoline (see Example 12(12)) by catalytic reduction analogously to Example 25.
Yield: 75% of theory.

EXAMPLE 14

1-[3-(4-cyano-phenyl)-propionyl]-6-benzylamino-1,2,3,4-tetrahydro-quinoline 2.9 g (9.5 mmol) of 6-amino1-[3-(4-cyano-phenyl) propionyl]-1,2,3,4-tetrahydro-quinoline are dissolved in 80 ml of methanol and 0.6 ml of acetic acid, combined with 1.06 g (10 mmol) of benzaldehyde and stirred for 20 minutes at 0° C. Then 0.63 g sodium cyanoborohydride are added in small batches, stirring is continued for half an hour and the mixture is then allowed to warm up to ambient temperature. The solution is then concentrated by rotary evaporation and the residue is taken up in a little ice water. Then the solution is acidified and sodium hydroxide solution is added until an alkaline reaction is obtained and the mixture is then extracted with me-thylene chloride. The dried solution is concentrated by rotary evaporation and the residue is chromatographed over a silica gel column with toluene/ethyl acetate (1:1).

Yield: 3.7 g (98% of theory),
$C_{26}H_{25}N_3O$ (395.51)

| Calc.: | C78.95 | H6.37 | N10.62 |
|---|---|---|---|
| Found: | 79.08 | 6.54 | 9.76 |

The following are prepared analogously:
(1) 1-[3-(4-cyano-phenyl)-propionyl]-6-[(naphth-1-yl-methyl)-amino]-1,2,3,4-tetrahydro-quinoline
Yield: 78% of theory,
$C_{30}H_{27}N_3O$ (445.57)

| Calc.: | C80.87 | H6.10 | N9.43 |
|---|---|---|---|
| Found: | 80.33 | 6.36 | 8.98 |

(2) 1-[3-(4-cyano-phenyl)-propionyl]-6-[(naphth-2-yl-methyl)-amino]-1,2,3,4-tetrahydro-quinoline
Yield: 90% of theory,
$C_{30}H_{27}N_3O$ (445.57)

| Calc.: | C80.87 | H6.10 | N9.43 |
|---|---|---|---|
| Found: | 80.66 | 6.30 | 8.89 |

(3) 1-[3-(4-cyano-phenyl)-propionyl]-6-(N-methyl-benzylamino)-1,2,3,4-tetrahydro-quinoline
Prepared from 6-benzylamino-1-[3-(4-cyano-phenyl)-propionyl]-1,2,3,4-tetrahydro-quinoline (see Example 14) and formaldehyde
$R_f$ value=0.42 (silica gel; methylene chloride/ethyl acetate=19:1)
(4) 1-[3-(4-cyano-phenyl)propionyl]-6-(2,2-diphenyl-ethyl-amino)-1,2,3,4-tetrahydro-quinoline
Prepared from 6-amino-1-[3-(4-cyano-phenyl)propionyl]-1,2,3,4-tetrahydro-quinoline and diphenylacetyl-dehyde
Yield: 80% of theory,
$R_f$ value=0.49 (silica gel; methylene chloride/ethyl acetate=9:1)

EXAMPLE 15

1-[3-(4-cyano-phenyl)-propionyl]-6-(N-ethylaminocarbonylmethyl-benzylamino)-1,2,3,4-tetrahydro-quinoline To a solution of 1.2 g of 1-[3-(4-cyano-phenyl)-propionyl]-6-[N-hydroxycarbonylmethyl-N-benzyl-amino]-1,2,3,4-tetrahydro-quinoline [prepared analogously to Example 32 from 1-[3-(4-cyano-phenyl)-propionyl]-6-[N-ethoxycarbonylmethyl-N-benzyl-amino]-1,2,3,4-tetrahydro-quinoline] (see Example 6(1)) in 15 ml of dim-ethylformamide are added 0.8 g of dicyclohexyl carbodiimide and the mixture is stirred for 10 minutes at 40° C. Then it is cooled to 0° C. and 0.22 g of ethylamine in 5 ml of dimethylformamide are added and left overnight with stirring. Then the solution is evaporated down and the residue is chromatographed over a silica gel column with methylene chloride/ethyl acetate (8:2).
Yield: 94% of theory,
$R_f$ value: 0.29 (silica gel; methylene chloride/ethyl acetate=8:2)

The following are prepared analogously:
(1) 1[-3-(4-cyano-phenyl)propionyl]-6-[N-(N,N-dipropylaminocarbonylmethyl)-benzylamino]-1,2,3,4-tetrahydro-quinoline
Yield: 51% of theory,
$R_f$ value: 0.43 (silica gel; methylene chloride/ethyl acetate=9:1)
(2) 1-[3-(4-cyano-phenyl)-propionyl]-6-[N-(benzylamino-carbonylmethyl)-benzylamino]-1,2,3,4-tetrahydro-quinoline
Yield: 92% of theory,
$R_f$ value: 0.38 (silica gel; methylene chloride/ethyl acetate=8:2)
(3) 1-[3-(4-cyano-phenyl)-propionyl]-6-[N-(phenylaminocarbonylmethyl)-benzylamino]-1,2,3,4-tetrahydro-quinoline
Yield: 60% of theory,
$R_f$ value: 0.58 (silica gel; methylene chloride/ethyl acetate=9:1)

EXAMPLE 16

1-[3-(4-cyano-phenyl)-propionyl]-6-phenylaminosulphonyl-1,2,3,4-tetrahydro-quinoline
(a) 1-[3-(4-cyano-phenyl)-propionyl]-1,2,3,4-tetrahydro-quinoline-6-sulphonylchloride (0.04 mol) of 1-[3-(4-cyano-phenyl)-propionyl]-1,2,3,4-tetrahydro-quinoline are dissolved in 16 ml of chlorosulphonic acid at 0° C. The thickly liquid mass is heated to 60° C. and hydrochloric acid develops. Then the mixture is carefully added to ice and extracted with methylene chloride, dried and concentrated by rotary evaporation.
Yield: 5.9 g (38% of theory),
(b) 1-[3-(4-cyano-phenyl)-propionyl]-6-phenylaminosulphonyl-1,2,3,4-tetrahydro-quinoline 2.33 g (6 mmol) of crude 1-[3-(4-cyano-phenyl)-propionyl]-1,2,3,4-tetrahydro-quinoline-6-sulphonylchloride are added dropwise, whilst cooling with ice, to a solution of 0.56 g of aniline in 15 ml of pyridine. Then the mixture is heated for 30 minutes to 100° C. and evaporated to dryness. The residue is chromatographed over a silica gel column with methylene chloride:ethyl acetate.
Yield: 0.5 g (18% of theory).
The following are prepared analogously:
(1) 1-[3-(4-cyano-phenyl)-propionyl]-6-benzylaminosulphonyl-1,2,3,4-tetrahydro-quinoline
Yield: 12% of theory
(2) 1-[3-(4-cyano-phenyl)-propionyl]-6-phenylsulphonyl-1,2,3,4-tetrahydro-quinoline
Prepared from 1-[3-(4-cyano-phenyl)-propionyl]-1,2,3,4-tetrahydro-quinoline with benzenesulphonic acid chloride and aluminium chloride in dimethylformamide.
Yield: 38% of theory,
$R_f$ value: 0.19 (toluene/ethyl acetate=8:2)
(3) 1-[3-(4-cyano-phenyl)-propionyl]-6-benzoyl-1,2,3,4-tetrahydro-quinoline
Prepared from 1-[3-(4-cyano-phenyl)-propionyl]-1,2,3,4-tetrahydro-quinoline with benzoic acid chloride and aluminium chloride in dimethylformamide.
Yield: 10% of theory,
$R_f$ value: 0.61 (toluene/ethyl acetate=7:3)

EXAMPLE 17

1-[N-(4-cyano-benzyl)-methylaminocarbonyl]-6-phenylsulphonylamino-1,2,3,4-tetrahydro-quinoline A suspension of 0.87 g (3 mmol) of 6-phenylsulphonamido-1,2,3,4-tetrahydro-quinoline in 8 ml of toluene and 1.55 ml of a 20% solution of phosgene in toluene are stirred for 3 hours at ambient temperature, then combined with 0.44 g p-cyano-N-methyl-benzylamine and refluxed for three hours. Then the reaction mixture is concentrated by rotary evaporation and the residue is chromatographed over a silica gel column with methylene chloride/methanol (39:1).

Yield: 0.81 g (58% of theory), $R_f$ value: 0.32 (silica gel; methylene chloride/ethyl acetate=4:1)

The following is prepared analogously:

(1) 1-[N-(4-cyano-benzyl)-aminocarbonyl]-6-phenylsulphonyl-amino-1,2,3,4-tetrahydro-quinoline Yield: 64% of theory.

$R_f$ value: 0.18 (silica gel; methylene chloride/methanol=4:1)

EXAMPLE 18

1-[3-(4-cyano-phenyl)propyl]-6-phenylsulphonamido-1,2,3,4-tetrahydro-quinoline 1.73 g 6-phenylsulphonamido-1,2,3,4-tetrahydro-quinoline are dissolved with 0.7 g triethylamine in 10 ml of dimethylformamide and combined with 1.62 g of 3-(4-cyanophenyl)propyliodide in 15 ml of dimethylformamide and stirred for 5 hours at 40–50° C. Then the mixture is evaporated down, the residue is dissolved in ethyl acetate/water, the organic phase is dried and concentrated by evaporation in vacuo. The product is chromatographed with methylene chloride/ethyl acetate (19:1) over a silica gel column.

Yield: 600 mg (23% of theory),

Melting point: 131–132° C.

EXAMPLE 19

1-[3-(4-cyano-phenyl)thiopropionyl]-6-phenylsulphonamido-1,2,3,4-tetrahydro-quinoline 4.9 g of 1-[3-(4-cyano-phenyl)propionyl]-6-phenylsulphonamido-1,2,3,4-tetrahydro-quinoline are dissolved in 110 ml of toluene and boiled with 2.5 g Lawesson reagent [2,4-bis(4-methoxy-phenyl)-1,3-dithia-2,4-diphosphetane-2,4-disulphide] for 1 hour at 110–120° C. Then the mixture is evaporated to dryness and the residue is chromatographed over a silica gel column with methylene chloride/ethyl acetate=19:1.

Yield: 3.5 g (69% of theory),

Melting point: 169–171° C.

$C_{25}H_{23}N_3O_2S_2$ (461.61)

| Calc.: | C65.08 | H5.02 | N9.10 | S13.89 |
|---|---|---|---|---|
| Found: | 64.84 | 5.09 | 9.02 | 13.71 |

EXAMPLE 20

1-[3-(4-cyano-phenyl)propionyl]-2,3,4,5-tetrahydro-1H-benzo[b]azepine

Prepared analogously to Example 1 by reacting 2,3,4,5-tetrahydro-1H-benzo[b]azepine and 3-(4-cyano-phenyl) propionic acid chloride.

Yield: 3.0 g (82% of theory), $R_f$ value: 0.54 (silica gel; toluene/ethyl acetate=7:3)

EXAMPLE 21

1-[3-(4-cyano-phenyl)propyl]-dihydrocarbostyryl 1.47 g of dihydrocarbostyryl are dissolved in 10 ml of dimethylsulphoxide and combined with 0.49 g sodium hydride in oil at ambient temperature. Then 2.71 g of 3-(4-cyano-phenyl)propyliodide in 5 ml of dimethylsulphoxide are added and the mixture is stirred for 1½ hours at ambient temperature. Then the solution is added to 20 ml of water and extracted three times with ethyl acetate. The combined organic phases are dried and concentrated by evaporation in vacuo. The oil obtained is chromatographed over silica gel with toluene/ethyl acetate (8:2).

Yield: 2.5 g (86% of theory), $R_f$ value: 0.63 (silica gel; toluene/ethyl acetate=8:2).

EXAMPLE 22

1-[3-(4-cyano-phenyl)propyl]-6-nitro-dihydrocarbostyryl

Prepared analogously to Example 3 by nitrating 1-[3-(4-cyano-phenyl)propyl]-dihydrocarbostyryl.

Yield: 70% of theory, $R_f$ value: 0.30 (silica gel; toluene/ethyl acetate=8:2).

EXAMPLE 23

1-[3-(4-cyano-phenyl)propyl]-6amino-dihydrocarbostyryl

Prepared analogously to Example 2 by reduction of 1-[3-(4-cyano-phenyl)propyl]-6-nitro-dihydrocarbostyryl.

Yield: 86% of theory, $R_f$ value: 0.45 (silica gel; ethyl acetate).

EXAMPLE 24

1-[3-(4-amidino-phenyl)propionyl]-6-phenylsulphonamido-1,2,3,4-tetrahydro-quinoline-hydrochloride At −10° C., 1.3 g of 1-[3-(4-cyano-phenyl)propionyl]-6-phenylsulphonamido-1,2,3,4-tetrahydro-quinoline (see Example 9) are added to 25 ml of ethanol saturated with hydrogen chloride and at −5° C. a weak current of hydrogen chloride is passed through the solution for one hour. Then the mixture is allowed to come up to ambient temperature and stirred overnight. It is then concentrated by evaporation and the residue is washed with ethanol. Then the residue is suspended in 50 ml of methanol, 2.25 g of ammonium carbonate are added and the mixture is left to stand overnight. The solution is then concentrated by evaporation and the residue is chromatographed over a silica gel column with methylene chloride/methanol=8:2.

Yield: 1.15 g (77% of theory),

Melting point: from 140° C. (decomp.)

$C_{25}H_{26}N_4O_3S \times HCl \times H_2O$ (517.06)

| Calc.: | C58.08 | H5.65 | N10.84 | S6.20 |
|---|---|---|---|---|
| Found: | 58.39 | 5.73 | 10.54 | 6.07 |

The following are prepared analogously:

(1) 1-[3-(4-amidino-phenyl)propionyl]-6-(2-naphthyl-sulphonamido)-1,2,3,4-tetrahydro-quinoline-hydrochloride Prepared from the compound prepared according to Example 9(1)

Yield: 83% of theory,

Melting point: from 115° C. (decomp.)

$C_{29}H_{28}N_4O_3S \times 1.25$ HCl (558.20)

| Calc.: | C | 62.41 | H | 5.30 | N | 10.03 |
|---|---|---|---|---|---|---|
| Found: |  | 61.94 |  | 5.65 |  | 9.82 |

(2) 1-[3-(4-amidino-phenyl)propionyl]-6-(1-naphthyl-sulphonamido)-1,2,3,4-tetrahydro-quinoline-hydrochloride Prepared from the compound prepared according to Example 9(2)

Yield: 55% of theory,

Melting point: 100° C. (decomp.)

$C_{29}H_{28}N_4O_3S \times HCl \times 2\,H_2O$ (585.13)

| Calc.: | C | 59.50 | H | 5.68 | N | 9.75 |
|---|---|---|---|---|---|---|
| Found: |  | 59.66 |  | 5.84 |  | 10.03 |

(3) 1-[3-(4-amidino-phenyl)propionyl]-6-(4-fluoro-phenylsulphonamido)-1,2,3,4-tetrahydro-quinoline-hydrochloride Prepared from the compound prepared according to Example 9(3)
Yield: 86% of theory,
Melting point: 135° C. (decomp.)
$C_{25}H_{25}FN_4O_3S \times 1.25\,HCl$ (526.14)

| Calc.: | C | 57.08 | H | 5.03 | N | 10.65 |
|---|---|---|---|---|---|---|
| Found: |  | 57.08 |  | 5.39 |  | 10.72 |

(4) 1-[3-(4-amidino-phenyl)propionyl]-6-butylsulphonamido-1,2,3,4-tetrahydro-quinoline-hydrochloride Prepared from the compound prepared according to Example 9(4)
Yield: 76% of theory,
Melting point: 122° C. (decomp.)
$C_{23}H_{30}N_4O_3S \times HCl \times 0.5\,H_2O$ (488.06)

| Calc.: | C | 56.60 | H | 6.60 | N | 11.48 |
|---|---|---|---|---|---|---|
| Found: |  | 56.56 |  | 6.60 |  | 11.50 |

(5) 1-[3-(4-amidino-phenyl)propionyl]-5-phenylsulphonamido-1,2,3,4-tetrahydro-quinoline-hydrochloride Prepared from the compound prepared according to Example 9(5)
Yield: 56% of theory,
Melting point: from 116° C. (sintering from 95° C.)
$C_{25}H_{26}N_4O_3S \times HCl \times H_2O$ (517.05)

| Calc.: | C | 58.07 | H | 5.65 | N | 10.84 |
|---|---|---|---|---|---|---|
| Found: |  | 58.53 |  | 5.80 |  | 10.94 |

(6) 1-[3-(4-amidino-phenyl)propionyl]-7-phenylsulphonamido-1,2,3,4-tetrahydro-quinoline-hydrochloride Prepared from the compound prepared according to Example 9(6)
Yield: 67% of theory,
Melting point: from 105° C.
$C_{25}H_{26}N_4O_3S \times HCl \times H_2O$ (517.05)

| Calc.: | C | 58.08 | H | 5.65 | N | 10.84 |
|---|---|---|---|---|---|---|
| Found: |  | 58.25 |  | 5.72 |  | 10.44 |

(7) 1-[3-(4-amidino-phenyl)propionyl]-7-benzylsulphonamido-1,2,3,4-tetrahydro-quinoline-hydrochloride Prepared from the compound prepared according to Example 9(7)
Yield: 51% of theory,
Melting point: from 108° C. (decomp.)
$C_{26}H_{28}N_4O_3S \times HCl \times 0.5\,H_2O$ (522.07)

| Calc.: | C | 59.82 | H | 5.79 | N | 10.73 |
|---|---|---|---|---|---|---|
| Found: |  | 59.66 |  | 5.87 |  | 10.45 |

(8) 1-[3-(4-amidino-phenyl)propionyl]-6-(4-amino-3,5-dichlorophenylsulphonamido)-1,2,3,4-tetrahydro-quinoline-hydrochloride Prepared from the compound prepared according to Example 10
Yield: 73% of theory,
Melting point: 115° C. (decomp.)
$C_{25}H_{25}Cl_2N_5O_3S \times HCl$ (582.44)

| Calc.: | C | 51.51 | H | 4.50 | N | 12.01 |
|---|---|---|---|---|---|---|
| Found: |  | 51.52 |  | 4.71 |  | 11.94 |

(9) 1-[3-(4-amidino-phenyl)propionyl]-6-propylsulphonamido-1,2,3,4-tetrahydro-quinoline-hydrochloride Prepared from the compound prepared according to Example 10(2)
Yield: 46% of theory,
Melting point: 123° C. (decomp.)
$C_{22}H_{28}N_4O_3S \times HCl$ (465.02)

| Calc.: | C | 56.82 | H | 6.29 | N | 12.05 |
|---|---|---|---|---|---|---|
| Found: |  | 57.19 |  | 6.52 |  | 11.77 |

(10) 1-[3-(4-amidino-phenyl)propionyl]-6-(5-chloro-thien-2-yl-sulphonamido)-1,2,3,4-tetrahydro-quinoline-hydrochloride Prepared from the compound prepared according to Example 10(3)
Yield: 96% of theory,
Melting point: 100° C. (decomp.)
$C_{23}H_{23}ClN_4O_3S_2 \times HCl \times 0.5\,H_2O$ (548.51)

| Calc.: | C | 50.36 | H | 4.50 | N | 10.21 |
|---|---|---|---|---|---|---|
| Found: |  | 50.66 |  | 4.70 |  | 10.01 |

(11) 1-[3-(4-amidino-phenyl)propionyl]-6-isopropylsulphonamido-1,2,3,4-tetrahydro-quinoline-hydrochloride Prepared from the compound prepared according to Example 10(4)
Yield: 62% of theory,
Melting point: 110° C. (decomp.)
$C_{22}H_{28}N_4O_3S \times HCl \times 0.5\,H_2O$ (474.02)

| Calc.: | C | 55.74 | H | 6.26 | N | 11.82 |
|---|---|---|---|---|---|---|
| Found: |  | 55.62 |  | 6.62 |  | 11.07 |

(12) 1-[3-(4-amidino-phenyl)propionyl]-6-(3-chloropropylsulphonamido)-1,2,3,4-tetrahydro-quinoline-hydrochloride Prepared from the compound prepared according to Example 10(5)
Yield: 100% of theory,
Melting point: 85° C. (decomp.)
$C_{22}H_{27}ClN_4O_3S \times HCl \times C_2H_5OH$ (545.53)

| Calc.: | C | 52.84 | H | 6.28 | N | 10.27 |
|---|---|---|---|---|---|---|
| Found: | | 54.01 | | 6.41 | | 9.98 |

(13) 1-[3-(4-amidino-phenyl)propionyl]-6-benylsulphonamido-1,2,3,4-tetrahydro-quinoline-hydrochloride
Yield: 62% of theory,
Melting point: from 80° C.
$C_{26}H_{28}N_4O_3S \times HCl \times H_2O$ (531.08)

| Calc.: | C | 58.80 | H | 5.88 | N | 10.55 | S | 6.04 |
|---|---|---|---|---|---|---|---|---|
| Found: | | 58.75 | | 5.90 | | 10.61 | | 5.95 |

(14) 1-[3-(4-amidino-phenyl)propionyl]-6-phenylacetylamino-1,2,3,4-tetrahydro-quinoline-hydrochloride
Prepared from the compound prepared according to Example 9(9)
Yield: 53% of theory,
Melting point: from 150° C.
$C_{27}H_{28}N_4O_2 \times HCl \times H_2O$ (495.03)

| Calc.: | C | 65.51 | H | 6.31 | N | 11.32 |
|---|---|---|---|---|---|---|
| Found: | | 65.58 | | 6.38 | | 11.13 |

(15) 1-[3-(4-amidino-phenyl)propionyl]-6-benzoylamino-1,2,3,4-tetrahydro-quinoline-hydrochloride
Yield: 75% of theory,
Melting point: from 170° C.
$C_{26}H_{26}N_4O_2 \times HCl \times H_2O$ (487.00)

| Calc.: | C | 64.93 | H | 6.08 | N | 11.65 |
|---|---|---|---|---|---|---|
| Found: | | 65.02 | | 6.22 | | 11.66 |

(16) 1-[3-(4-amidino-phenyl)propyl]-6-phenylsulphonamido-1,2,3,4tetrahydro-quinoline-hydrochloride
Prepared from the compound prepared according to Example 18
Yield: 26% of theory,
Melting point: from 140° C.
$C_{25}H_{28}N_4O_2S \times HCl \times H_2O$ (503.07);

| Calc.: | C | 59.69 | H | 6.21 | N | 11.14 | S | 6.37 |
|---|---|---|---|---|---|---|---|---|
| Found: | | 59.72 | | 6.08 | | 10.97 | | 6.38 |

(17) 1-[3-(4-amidino-phenyl)thiopropionyl]-6-phenyl-sulphonamido-1,2,3,4-tetrahydro-quinoline-hydrochloride
Prepared from the compound prepared according to Example 19
Yield: 14% of theory,
Melting point: from 140° C. (decomp.)
$C_{25}H_{26}N_4O_2S_2 \times HCl \times H_2O$ (533.12)

| Calc.: | C | 56.33 | H | 5.48 | N | 10.51 | S | 12.03 | Cl | 6.65 |
|---|---|---|---|---|---|---|---|---|---|---|
| Found: | | 56.45 | | 5.52 | | 10.28 | | 11.87 | | 6.93 |

(18) 1-[3-(4-amidino-phenyl)propionyl]-5-phenylsulphonamido2,3-dihydro-indole-hydrochloride
Prepared from the compound prepared according to Example 10(6)
Melting point: from 128° C. (decomp.)
$C_{24}H_{24}N_4O_3S \times HCl \times 1.5\ H_2O$ (512.01)

| Calc.: | C | 56.14 | H | 5.31 | N | 10.96 |
|---|---|---|---|---|---|---|
| Found: | | 56.30 | | 5.51 | | 10.96 |

(19) 1-[3-(4-amidino-phenyl)propionyl]-7-phenylsulphonamido-2,3,4,5-tetrahydro-1H-benzo[b]azepine-hydrochloride
Prepared from the compound prepared according to Example 10(7)
Yield: 22.0% of theory,
Melting point: from 207° C. (decomp.)
$C_{26}H_{28}N_4O_3S \times HCl \times C_2H_5OH$ (559.07)

| Calc.: | C | 60.16 | H | 6.31 | N | 10.02 |
|---|---|---|---|---|---|---|
| Found: | | 60.44 | | 6.42 | | 9.41 |

(20) 1-[3-(4-amidino-phenyl)propionyl]-3-methyl-6-phenylsulphonamido-1,2,3,4-tetrahydro-quinoline-hydrochloride
Prepared from the compound prepared according to Example 10(8)
Yield: 55% of theory,
Melting point: from 140° C.
$C_{26}H_{28}N_4O_3S \times HCl$ (513.07)

| Calc.: | C | 60.86 | H | 5.70 | N | 10.92 |
|---|---|---|---|---|---|---|
| Found: | | 61.09 | | 6.05 | | 10.21 |

(21) 1-[3-(4-amidino-phenyl)propionyl]-4-methyl-6-phenylsulphonamido-1,2,3,4-tetrahydro-quinoline-hydrochloride
Prepared from the compound prepared according to Example 10(9)
Yield: 68% of theory,
Melting point: from 133° C. (decomp.)
$C_{26}H_{28}N_4O_3S \times HCl$ (513.07)

| Calc.: | C | 60.86 | H | 5.70 | N | 10.92 |
|---|---|---|---|---|---|---|
| Found: | | 59.82 | | 5.79 | | 20.73 |

(22) 1-[3-(4-amidino-phenyl)propionyl]-2-methyl-6-phenyl-sulphonamido-1,2,3,4-tetrahydro-quinoline-hydrochloride
Prepared from the compound prepared according to Example 9(14)
Yield: 37% of theory, Melting point: from 112° C. (decomp.)
$C_{26}H_{29}ClN_4O_3S \times HCl \times 2\ H_2O$ (549.07)

| Calc.: | C | 56.87 | H | 6.06 | N | 10.02 |
|---|---|---|---|---|---|---|
| Found: |  | 56.43 |  | 5.98 |  | 9.90 |

(23) 1-[3-(4-amidino-phenyl)propionyl]-6-[(5-dimethylamino-naphth-1-yl)sulphonamido]-1,2,3,4-tetrahydro-quinoline-hydrochloride Prepared from the compound prepared according to Example 10(1)
Yield: 52% of theory,
$C_{31}H_{33}N_5O_3S \times 1.25$ HCl (601.03)

| Calc.: | C | 61.98 | H | 5.87 | N | 11.65 |
|---|---|---|---|---|---|---|
| Found: |  | 61.64 |  | 6.43 |  | 10.38 |

(24) 1-[N-(4-amidino-benzyl)-aminocarbonyl]-6-phenylsulphonylamino-1,2,3,4-tetrahydro-quinoline-hydrochloride
Yield: 64% of theory,
$C_{24}H_{25}N_5O_3S$ (463.57)
mass spectrum: FAB-MS: $(M+H)^+=464$

(25) 1-[3-(4-amidino-phenyl)propyl]-6-phenylsulphonamido-dihydrocarbostyryl-hydrochloride
Melting point: from 136° C.
$C_{25}H_{26}N_4O_3S \times HCl \times 2\ H_2O$ (535.07)

| Calc.: | C | 56.22 | H | 5.85 | N | 10.49 |
|---|---|---|---|---|---|---|
| Found: |  | 55.15 |  | 5.58 |  | 10.58 |

(26) 1-[3-(4-amidino-phenyl)propionyl]-6-(3-trifluoromethyl-benzolsulphonylamino)-1,2,3,4-tetrahydro-quinoline-hydrochloride Prepared from the compound prepared according to Example 10(10)
Yield: 72% of theory,
Melting point: 146–147° C.
$C_{26}H_{25}F_3N_4O_3S \times HCl \times C_2H_5OH$ (613.14)

| Calc.: | C | 54.85 | H | 5.26 | N | 9.14 | Cl | 5.78 |
|---|---|---|---|---|---|---|---|---|
| Found: |  | 54.71 |  | 5.23 |  | 9.10 |  | 6.00 |

(27) 1-[3-(4-amidino-phenyl)propionyl]-6-(2,5-dichlorobenzolsulphonylamino)-1,2,3,4-tetrahydro-quinoline-hydrochloride Prepared from the compound prepared according to Example 10(11)
Yield: 77% of theory,
Melting point: 239° C.
$C_{25}H_{24}Cl_2N_4O_3S \times HCl$ (567.93)

| Calc.: | C | 52.67 | H | 4.44 | N | 9.87 |
|---|---|---|---|---|---|---|
| Found: |  | 50.33 |  | 4.86 |  | 10.39 |

(28) 1-[3-(4-amidino-phenyl)propionyl]-6-(2,3,5,6-tetramethyl-benzolsulphonylamino)-1,2,3,4-tetrahydro-quinoline-hydrochloride Prepared from the compound prepared according to Example 10(12)
Yield: 12% of theory,
Melting point: 224–225° C.
$R_f$ value: 0.28 (silica gel; methylene chloride/ethanol= 4:1)

(29) 1-[3-(4-amidino-phenyl)propionyl]-6-(5-isoquinolinyl-sulphonylamino)-1,2,3,4-tetrahydro-quinoline-hydrochloride Prepared from the compound prepared according to Example 10(14)
Yield: 66% of theory,
Melting point: 195° C.
$C_{28}H_{27}N_5O_3S \times HCl \times H_2O$ (568.1)

| Calc.: | C | 58.45 | H | 5.24 | N | 12.17 |
|---|---|---|---|---|---|---|
| Found: |  | 57.49 |  | 5.64 |  | 11.97 |

(30) 1-[3-(4-amidino-phenyl)propionyl]-6-(cyclopropyl-sulphonylamino)-1,2,3,4-tetrahydro-quinoline-hydrochloride Prepared from the compound prepared according to Example 10(15)
Yield: 87% of theory,
Melting point: from 85° C.
$C_{22}H_{26}N_4O_3S \times HCl$ (463.0)

| Calc.: | C | 57.07 | H | 5.88 | N | 12.10 |
|---|---|---|---|---|---|---|
| Found: |  | 56.35 |  | 6.55 |  | 11.33 |

(31) 1-[3-(4-amidino-phenyl)propionyl]-6-(benzimidazol-5-yl-sulphonylamino)-1,2,3,4-tetrahydro-quinoline-hydrochloride Prepared from the compound prepared according to Example 10(16)
Yield: 66% of theory,
Melting point: from 220° C.
$C_{26}H_{26}N_6O_3S \times HCl \times H_2O$ (557.08)

| Calc.: | C | 56.06 | H | 5.25 | N | 15.09 |
|---|---|---|---|---|---|---|
| Found: |  | 55.76 |  | 5.37 |  | 14.74 |

(32) 1-[3-(3-amidino-phenyl)propionyl]-6-phenylsulphonylamino-1,2,3,4-tetrahydro-quinoline-hydrochloride Prepared from the compound prepared according to Example 9(24)
Yield: 17% of theory
Melting point: from 134–139° C.
$C_{25}H_{26}N_4O_3S \times HCl \times H_2O$ (517.05)

| Calc.: | C | 58.08 | H | 5.65 | N | 10.84 |
|---|---|---|---|---|---|---|
| Found: |  | 57.52 |  | 5.83 |  | 10.04 |

(33) 1-[(4-amidino-phenyloxy)acetyl]-6-phenylsulphonylamino-1,2,3,4-tetrahydro-quinoline-hydrochloride Prepared from the compound prepared according to Example 9(25)
Yield: 44% of theory, Melting point: 137–143° C.
$C_{24}H_{24}N_4O_4S \times HCl \times H_2O$ (519.02)

| Calc.: | C | 55.54 | H | 5.24 | N | 10.79 |
|---|---|---|---|---|---|---|
| Found: |  | 54.57 |  | 5.31 |  | 10.50 |

(34) 1-[2-((4-amidino-phenyl)-methyl-amino]acetyl]-6-phenylsulphonylamino-1,2,3,4-tetrahydro-quinoline-hydrochloride
Prepared from the compound prepared according to Example 9(26)
Yield: 77% of theory,
Melting point: sinters from 180° C.
$C_{25}H_{27}N_5O_3S \times HCl \times H_2O$ (532.07)

| Calc.: | C | 56.44 | H | 5.68 | N | 13.16 | S | 6.03 |
|---|---|---|---|---|---|---|---|---|
| Found: |  | 55.71 |  | 5.53 |  | 13.03 |  | 5.87 |

(35) 1-[3-(4-amidino-phenyl)-propionyl]-6-(cyclohexyl-sulphonylamino)-1,2,3,4-tetrahydro-quinoline-hydrochloride
Prepared from the compound prepared according to Example 10(17)
Yield: 62% of theory,
Melting point: decomposition from 125° C.
$C_{25}H_{32}N_4O_3S \times HCl \times H_2O$ (523.10)

| Calc.: | C | 57.40 | H | 6.74 | N | 10.71 | S | 6.13 |
|---|---|---|---|---|---|---|---|---|
| Found: |  | 57.22 |  | 6.56 |  | 10.58 |  | 6.07 |

(36) 1-[3-(4-amidino-phenyl)propionyl]-6-(3-tolyl-sulphonylamino)-1,2,3,4-tetrahydro-quinoline-hydrochloride
Prepared from the compound prepared according to Example 10(18)
Yield: 69% of theory,
Melting point: from 260° C.
$C_{26}H_{28}N_4O_3S \times HCl \times H_2O$ (531.08)

| Calc.: | C | 58.80 | H | 5.88 | N | 10.54 |
|---|---|---|---|---|---|---|
| Found: |  | 58.97 |  | 5.84 |  | 10.40 |

(37) 1-[3-(4-amidino-phenyl)propionyl]-6-(4-methoxy-benzenesulphonylamino)-1,2,3,4-tetrahydro-quinoline-hydrochloride
Prepared from the compound prepared according to Example 10(19)
Yield: 80% of theory,
$C_{26}H_{28}N_4O_4S \times HCl \times H_2O$ (547.08)

| Calc.: | C | 57.08 | H | 5.71 | N | 10.24 |
|---|---|---|---|---|---|---|
| Found: |  | 56.89 |  | 6.19 |  | 9.27 |

(38) 1-[3-(4-amidino-phenyl)-propionyl]-6-(3-aminocarbonylbenzene-sulphonylamino)-1,2,3,4-tetrahydro-quinoline-hydrochloride
Yield: 32% of theory,
$C_{26}H_{27}N_5O_4S \times HCl \times H_2O$ (560.08)

| Calc.: | C | 55.76 | H | 5.40 | N | 12.50 |
|---|---|---|---|---|---|---|
| Found: |  | 54.15 |  | 5.74 |  | 10.75 |

(39) 1-[3-(4-amidino-phenyl)-propionyl]-6-(N-benzoyl-methylamino)-1,2,3,4-tetrahydro-quinoline-hydrochloride
Prepared from the compound prepared according to Example 11(2)
Yield: 65% of theory,
Melting point: 90–92° C.
$C_{27}H_{28}N_4O_2 \times HCl \times 2H_2O$ (512.03)

| Calc.: | C | 63.34 | H | 6.30 | N | 10.94 |
|---|---|---|---|---|---|---|
| Found: |  | 63.21 |  | 6.48 |  | 10.92 |

(40) 1-[3-(4-amidino-phenyl)-propionyl]-6-[N-(4-chlorobenzoyl)-methylamino]-1,2,3,4-tetrahydro-quinoline-hydrochloride
Prepared from the compound prepared according to Example 11(3)
Yield: 76% of theory,
$C_{27}H_{27}N_4O_2Cl \times HCl \times H_2O$ (529.47)

| Calc.: | C | 61.24 | H | 5.71 | N | 10.58 |
|---|---|---|---|---|---|---|
| Found: |  | 61.70 |  | 5.88 |  | 10.37 |

(41) 1-[3-(4-amidino-phenyl)-propionyl]-6-[N-(1-naphthoyl)-methylamino]-1,2,3,4-tetrahydro-quinoline-hydrochloride
Prepared from the compound prepared according to Example 11(4)
Yield: 71% of theory,
$C_{31}H_{30}N_4O_2 \times HCl \times 1.5\ H_2O$ (554.09)

| Calc.: | C | 67.19 | H | 6.18 | N | 10.11 |
|---|---|---|---|---|---|---|
| Found: |  | 67.22 |  | 6.12 |  | 10.19 |

(42) 1-[3-(4-amidino-phenyl)-propionyl]-6-[N-(2-naphthoyl)-methylamino]-1,2,3,4-tetrahydro-quinoline-hydrochloride
Prepared from the compound prepared according to Example 11(5)
Yield: 72% of theory,
$C_{31}H_{30}N_4O_2 \times HCl \times H_2O$ (545.09)

| Calc.: | C | 68.30 | H | 6.10 | N | 10.27 |
|---|---|---|---|---|---|---|
| Found: |  | 68.03 |  | 6.28 |  | 10.27 |

(43) 1-[3-(4-amidino-phenyl)-propionyl]-6-(N-butyryl-methylamino)-1,2,3,4-tetrahydro-quinoline-hydrochloride
Prepared from the compound prepared according to Example 11(6)
Yield: 59% of theory, $C_{24}H_{30}N_4O_2 \times HCl \times H_2O$ (461.01)

| | | | | | | |
|---|---|---|---|---|---|---|
| Calc.: | C | 62.52 | H | 7.21 | N | 12.15 |
| Found: | | 62.66 | | 7.28 | | 11.84 |

(44) 1-[3-(4-amidino-2-nitro-phenyl)-propionyl]-6-phenyl-sulphonylamino-1,2,3,4-tetrahydro-quinoline-hydrochloride
Prepared from the compound prepared according to Example 9(28)
Yield: 35% of theory,
$R_f$ value: 0.44 (silica gel; methylene chloride/methanol= 4:1)

(45) 1-[3-(4-amidino-3-amino-phenyl)-propionyl]-6-phenyl-sulphonylamino-1,2,3,4-tetrahydro-quinoline-hydrochloride
Yield: 53% of theory,
$C_{25}H_{27}N_5O_3 \times 2$ HCl (514.65)

| | | | | | | |
|---|---|---|---|---|---|---|
| Calc.: | C | 54.49 | H | 5.30 | N | 12.70 |
| Found: | | 54.60 | | 5.61 | | 12.47 |

(46) 1-[3-(4-amidino-2-acetylamino-phenyl)-propionyl]-6-phenylsulphonylamino-1,2,3,4-tetrahydro-quinoline-hydrochloride
Prepared from the compound prepared according to Example 11(7)
Yield: 59% of theory,
$C_{27}H_{29}N_5O_4S \times HCl$ (556.08)

| | | | | | | |
|---|---|---|---|---|---|---|
| Calc.: | C | 53.32 | H | 5.44 | S | 5.76 |
| Found: | | 52.93 | | 5.87 | | 5.50 |

(47) 1-[3-(4-amidino-2-(2-ethoxycarbonylethylcarbonylamino)-phenyl)-propionyl]-6-phenylsulphonylamino-1,2,3,4-tetrahydro-quinoline-hydrochloride
Prepared from the compound prepared according to Example 11(8)
Yield: 35% of theory,
$C_{31}H_{35}N_35 O_6 S \times HCl$ (642.18)

| | | | | | | |
|---|---|---|---|---|---|---|
| Calc.: | C | 57.98 | H | 5.49 | N | 10.90 |
| Found: | | 55.39 | | 5.91 | | 10.43 |

(48) 1-(4-amidino-benzoyl)-6-phenylsulphonylamino-1,2,3,4-tetrahydro-quinoline-hydrochloride
Prepared from the compound prepared according to Example 9(29)
Yield: 62% of theory,
$C_{23}H_{22}N_4O_3S \times HCl \times H_2O$ (489.00)

| | | | | | | |
|---|---|---|---|---|---|---|
| Calc.: | C | 56.49 | H | 5.15 | N | 11.46 |
| Found: | | 55.80 | | 5.04 | | 11.15 |

(49) 1-[3-(4-amidino-3-fluoro-phenyl)-propionyl]-6-phenylsulphonylamino-1,2,3,4-tetrahydro-quinoline-hydrochloride
Prepared from the compound prepared according to Example 9(31)
Yield: 55% of theory,
$C_{25}H_{25}FN_4O_3S \times HCl$ (517.03)

| | | | | | | |
|---|---|---|---|---|---|---|
| Calc.: | C | 58.08 | H | 5.07 | N | 10.84 |
| Found: | | 57.63 | | 5.18 | | 10.75 |

(50) 1-[3-(2-amidino-pyridin-5-yl)-propionyl]-6-phenyl-sulphonylamino-1,2,3,4-tetrahydro-quinoline-hydrochloride
Prepared from the compound prepared according to Example 9(32)
Yield: 68% of theory,
$C_{24}H_{25}N_5O_3S \times HCl \times H_2O$ (518.04)

| | | | | | | |
|---|---|---|---|---|---|---|
| Calc.: | C | 55.65 | H | 5.45 | N | 13.52 |
| Found: | | 55.23 | | 5.54 | | 12.75 |

(51) 1-[3-(4-amidino-phenyl)-acroyl]-6-phenylsulphonylamino-1,2,3,4-tetrahydro-quinoline-hydrochloride
Prepared from the compound prepared according to Example 9(33)
Yield: 18% of theory,
$C_{25}H_{24}N_4O_3S \times HCl \times H_2O$ (515.04)

| | | | | | | | | |
|---|---|---|---|---|---|---|---|---|
| Calc.: | C | 58.30 | H | 5.28 | N | 10.88 | S | 6.23 |
| Found: | | 56.82 | | 5.29 | | 10.84 | | 6.29 |

(52) 1-[3-(4-amidino-phenyl)-propionyl]-6-piperidinocarbonyl-1,2,3,4-tetrahydro-quinoline-hydrochloride
Prepared from the compound prepared according to Example 9(34)
Yield: 65% of theory,
$C_{25}H_{30}N_4O_2 \times HCl \times 1.5$ $H_2O$ (481.99)

| | | | | | | |
|---|---|---|---|---|---|---|
| Calc.: | C | 62.29 | H | 7.11 | N | 11.62 |
| Found: | | 61.78 | | 6.94 | | 11.40 |

(53) 1-[3-(4-amidino-phenyl)-propionyl]-6-benzylaminocarbonyl-1,2,3,4-tetrahydro-quinoline-hydrochloride
Yield: 3% of theory,
$C_{27}H_{28}N_4O_2$ (440.55)
mass spectrum: $(M+H)^+ = 442$

(54) 1-[3-(4amidino-phenyl)-propionyl]-6-(N-methyl-phenyl-aminocarbonyl)-1,2,3,4-tetrahydro-quinoline-hydrochloride
Prepared from the compound prepared according to Example 9(36)
Yield: 5% of theory,
$C_{27}H_{28}N_4O_2 \times HCl \times H_2O$ (494.99)

| Calc.: | C | 65.51 | H | 6.31 | N | 11.32 |
|---|---|---|---|---|---|---|
| Found: | | 65.60 | | 6.26 | | 11.23 |

(55) 1-[3-(4-amidino-phenyl)-propionyl]-6-diethylamino-carbonyl-1,2,3,4-tetrahydro-quinoline-hydrochloride Prepared from the compound prepared according to Example 9(37)

Yield: 7% of theory, $C_{24}H_{30}N_4O_2 \times HCl \times 2.5\ H_2O$ (487.98)

| Calc.: | C | 59.07 | H | 7.44 | N | 11.48 |
|---|---|---|---|---|---|---|
| Found: | | 59.05 | | 7.06 | | 11.12 |

(56) 1-[3-(4-amidino-phenyl)-propionyl]-6-(3,5-dimethyl-piperidinocarbonyl)-1,2,3,4-tetrahydro-quinoline-hydrochloride Prepared from the compound prepared according to Example 9(38)

Yield: 7% of theory, $C_{27}H_{34}N_4O_2 \times HCl \times 2\ H_2O$ (519.04)

| Calc.: | C | 61.41 | H | 7.63 | N | 10.61 |
|---|---|---|---|---|---|---|
| Found: | | 60.76 | | 7.36 | | 10.35 |

(57) 1-[3-(4-amidino-phenyl)-propionyl]-6-(N-phenyl-butyl-aminocarbonyl) 1,2,3,4-tetrahydro-quinoline-hydrochloride Prepared from the compound prepared according to Example 12

Yield: 15% of theory, $C_{30}H_{34}N_4O_2 \times HCl \times H_2O$ (537.07)

| Calc.: | C | 67.08 | H | 6.94 | N | 10.43 |
|---|---|---|---|---|---|---|
| Found: | | 67.07 | | 6.85 | | 10.23 |

(58) 1-[3-(4amidino-phenyl)-propionyl]-6-[N-(4-chlorophenyl)-methylaminocarbonyl)-1,2,3,4-tetrahydro-quinoline-hydrochloride Prepared from the compound prepared according to Example 12(1)

Yield: 33% of theory, $C_{27}H_{27}N_4O_2 \times HCl \times H_2O$ (529.43)

| Calc.: | C | 61.25 | H | 5.71 | N | 10.58 |
|---|---|---|---|---|---|---|
| Found: | | 60.74 | | 5.70 | | 10.24 |

(59) 1-[3-(4-amidino-phenyl)-propionyl]-6-(N-phenyl-ethyl-aminocarbonyl)-1,2,3,4-tetrahydro-quinoline-hydrochloride Prepared from the compound prepared according to Example 12(2)

Yield: 64% of theory, $C_{28}H_{30}N_4O_2 \times HCl \times H_2O$ (509.02)

| Calc.: | C | 66.06 | H | 6.53 | N | 11.01 |
|---|---|---|---|---|---|---|
| Found: | | 66.55 | | 6.49 | | 10.82 |

(60) 1-[3-(4-amidino-phenyl)-propionyl]-6-diphenylamino-carbonyl-1,2,3,4-tetrahydro-quinoline-hydrochloride Prepared from the compound prepared according to Example 12(3)

Yield: 41% of theory, $C_{32}H_{30}N_4O_2 \times 2\ HCl \times 2\ H_2O$ (611.57)

| Calc.: | C | 62.85 | H | 5.94 | N | 9.17 |
|---|---|---|---|---|---|---|
| Found: | | 61.57 | | 5.99 | | 8.61 |

(61) 1-[3-(4-amidino-phenyl)-propionyl]-6-(N-phenyl-benzyl-aminocarbonyl)-1,2,3,4-tetrahydro-quinoline-hydrochlorid Prepared from the compound prepared according to Example 12(4)

Yield: 33% of theory,

Melting point: decomposition from 130° C.

(62) 1-[3-(4-amidino-phenyl)-propionyl]-6-(N-ethoxycarbonyl-methyl-phenylaminocarbonyl)-1,2,3,4-tetrahydro-quinoline-hydrochloride Prepared from the compound prepared according to Example 12(5)

Yield: 64% of theory, $C_{30}H_{32}N_4O_2 \times HCl$ (549.05)

| Calc.: | C | 65.62 | H | 6.06 | N | 10.20 |
|---|---|---|---|---|---|---|
| Found: | | 66.23 | | 6.29 | | 10.12 |

(63) 1-[3-(4-amidino-phenyl)-propionyl]-6-(N-cyclohexyl-methylaminocarbonyl)-1,2,3,4-tetrahydro-quinoline-hydrochloride Prepared from the compound prepared according to Example 12(6)

Yield: 30% of theory, $C_{27}H_{34}N_4O_2 \times HCl \times 0.5\ H_2O$ (492.04)

| Calc.: | C | 65.90 | H | 7.38 | N | 11.39 |
|---|---|---|---|---|---|---|
| Found: | | 65.88 | | 7.41 | | 11.14 |

(64) 1-[3-(4-amidino-phenyl)-propionyl]-6-(4-methyl-piperidino-carbonyl-1,2,3,4-tetrahydro-quinoline-hydrochloride Prepared from the compound prepared according to Example 9(22)

Yield: 38% of theory, $C_{26}H_{32}N_4O_2 \times HCl \times 2.5\ H_2O$ (514.02)

| Calc.: | C | 60.75 | H | 7.45 | N | 10.90 |
|---|---|---|---|---|---|---|
| Found: | | 60.51 | | 7.14 | | 10.70 |

(65) 1-[3-(4-amidino-phenyl)-propionyl]-6-morpholinocarbonyl-1,2,3,4-tetrahydro-quinoline-hydrochloride Prepared from the compound prepared according to Example 9(23)
Yield: 70% of theory,
$C_{24}H_{28}N_4O_3 \times HCl \times 2.5\ H_2O$ (501.96)

| Calc.: | C | 57.42 | H | 6.83 | N | 11.16 |
|---|---|---|---|---|---|---|
| Found: |  | 57.86 |  | 6.63 |  | 10.73 |

(66) 1-[3-(4-amidino-phenyl)-propionyl]-6-(N-ethoxycarbonylmethyl-cyclohexylaminocarbonyl)-1,2,3,4-tetrahydro-quinoline-hydrochloride
Prepared from the compound prepared according to Example 12(7)
Yield: 77% of theory,
$C_{30}H_{38}N_4O_4 \times HCl \times 0.5\ H_2O$ (564.10)

| Calc.: | C | 63.87 | H | 7.15 | N | 9.93 |
|---|---|---|---|---|---|---|
| Found: |  | 63.43 |  | 7.18 |  | 9.43 |

(67) 1-[3-(4-amidino-phenyl)-propionyl]-6-(2-ethoxycarbonyl-pyrrolidinocarbonyl)-1,2,3,4-tetrahydro-quinoline-hydrochloride
Prepared from the compound prepared according to Example 12(8)
Yield: 61% of theory,
$C_{27}H_{32}N_4O_4 \times HCl \times H_2O$ (531.02)

| Calc.: | C | 61.06 | H | 6.64 | N | 10.55 |
|---|---|---|---|---|---|---|
| Found: |  | 60.50 |  | 6.57 |  | 10.50 |

(68) 1-[3-(4-amidino-phenyl)-propionyl]-6-(2-ethoxycarbonyl-piperidinocarbonyl)-4,2,3,4-tetrahydro-quinoline-hydrochloride
Prepared from the compound prepared according to Example 12(9)
Yield: 63% of theory,
$C_{28}H_{34}N_4O_4 \times HCl \times H_2O$ (545.05)

| Calc.: | C | 61.69 | H | 6.84 | N | 10.28 |
|---|---|---|---|---|---|---|
| Found: |  | 61.45 |  | 6.67 |  | 9.96 |

(69) 1-[3-(4-amidino-phenyl)-propionyl]-6-(3-ethoxycarbonyl-piperidinocarbonyl)-1,2,3,4-tetrahydro-quinoline-hydrochloride
Prepared from the compound prepared according to Example 12(10)
Yield: 70% of theory,
$C_{28}H_{34}N_4O_4 \times HCl \times H_2O$ (545.05)

| Calc.: | C | 61.69 | H | 6.84 | N | 10.28 |
|---|---|---|---|---|---|---|
| Found: |  | 61.69 |  | 6.82 |  | 10.21 |

(70) 1-[3-(4-amidino-phenyl)-propionyl]-6-[N-(2-acetylaminoethyl)-phenylaminocarbonyl]-1,2,3,4-tetrahydro-quinoline-hydrochloride
Prepared from the compound prepared according to Example 12(11)
Yield: 22% of theory,
$C_{30}H_{33}N_5O_3 \times HCl \times 1.5\ H_2O$ (575.1)

| Calc.: | C | 62.61 | H | 6.44 | N | 12.18 |
|---|---|---|---|---|---|---|
| Found: |  | 62.76 |  | 6.35 |  | 12.04 |

(71) 1-[3-(4-amidino-phenyl)-propionyl]-6-[N-(2-aminoethyl)-phenylaminocarbonyl]-1,2,3,4-tetrahydro-quinoline-hydrochloride
Prepared from the compound prepared according to Example 13
Yield: 36% of theory,
mass spectrum: FAB-MS $(M+H)^+=470$

(72) 1-[3-(4-amidino-phenyl)-propionyl]-6-benzylamino-1,2,3,4-tetrahydro-quinoline-hydrochloride
Prepared from the compound prepared according to Example 14
Yield: 66% of theory,
$C_{26}H_{28}N_4O \times HCl \times 1.5\ H_2O$ (476.04)

| Calc.: | C | 65.60 | H | 6.77 | N | 11.77 |
|---|---|---|---|---|---|---|
| Found: |  | 65.17 |  | 6.81 |  | 11.36 |

(73) 1-[3-(4-amidino-phenyl)-propionyl]-6-(naphth-1-yl-methyl-amino)-1,2,3,4-tetrahydro-quinoline-hydrochloride
Prepared from the compound prepared according to Example 14(1)
Yield: 45% of theory,
$C_{30}H_{30}N_4O \times HCl \times 2\ H_2O$ (535,1)

| Calc.: | C | 67.33 | H | 6.59 | N | 10.47 |
|---|---|---|---|---|---|---|
| Found: |  | 66.07 |  | 6.85 |  | 9.42 |

(74) 1-[3-(4-amidino-phenyl)-propionyl]-6-(naphthalin-2-ylmethyl-amino)-1,2,3,4-tetrahydro-quinoline-hydrochloride
Prepared from the compound prepared according to Example 14(2)
Yield: 72% of theory,
$C_{30}H_{30}N_4O \times HCl \times 2\ H_2O$ (535,1)

| Calc.: | C | 67.33 | H | 6.59 | N | 10.47 |
|---|---|---|---|---|---|---|
| Found: |  | 67.21 |  | 6.64 |  | 10.05 |

(75) 1-[3-(4-amidino-phenyl)-propionyl]-6-(N-methyl-benzylamino)-1,2,3,4-tetrahydro-quinoline-hydrochloride
Prepared from the compound prepared according to Example 14(3)
Yield: 59% of theory
$C_{27}H_{30}N_4O \times HCl \times H_2O$ (481.06)

| Calc.: | C | 67.41 | H | 6.91 | N | 11.64 |
|---|---|---|---|---|---|---|
| Found: |  | 67.44 |  | 7.03 |  | 11.28 |

(76) 1-[3-(4-amidino-phenyl)-propionyl]-6-(N-ethoxycarbonylmethyl-benzylamino)-1,2,3,4-tetrahydro-quinoline-hydrochloride Prepared from the compound prepared according to Example 6(1)
Yield: 52% of theory,
$C_{30}H_{34}N_4O_3 \times HCl \times H_2O$ (553.13)

| Calc.: | C | 64.10 | H | 6.81 | N | 9.96 |
|---|---|---|---|---|---|---|
| Found: | | 64.17 | | 6.76 | | 10.04 |

(77) 1-[3-(4-amidino-phenyl)-propionyl]-6-[N-(ethoxycarbonylmethyl)-N-(naphth-2-yl-methyl)-amino]-1,2,3,4-tetrahydro-quinoline-hydrochloride
Prepared from the compound prepared according to Example 6(2)
Yield: 84% of theory,
$C_{34}H_{36}N_4O_3 \times HCl \times 1.5\ H_2O$ (612.19)

| Calc.: | C | 66.70 | H | 6.58 | N | 9.15 |
|---|---|---|---|---|---|---|
| Found: | | 66.81 | | 6.40 | | 9.46 |

(78) 1-[3-(4-amidino-phenyl)-propionyl]-6-[N-(ethoxycarbonylmethyl)-N-(naphth-1-yl-methyl)-amino]-1,2,3,4-tetrahydro-quinoline-hydrochloride
Prepared from the compound prepared according to Example 6(3)
Yield: 69% of theory,
$C_{34}H_{36}N_4O_3 \times HCl \times 1.5\ H_2O$ (612.19)

| Calc.: | C | 66.70 | H | 6.58 | N | 9.15 |
|---|---|---|---|---|---|---|
| Found: | | 66.83 | | 6.44 | | 9.14 |

(79) 1-[3-(4-amidino-phenyl)-propionyl]-6-(N-acetyl-N-benzylamino)-1,2,3,4-tetrahydro-quinoline-hydrochloride
Prepared from the compound prepared according to Example 11 (9)
Yield: 46% of theory,
$C_{28}H_{30}N_4O_2 \times HCl \times 2\ H_2O$ (527.07)

| Calc.: | C | 63.80 | H | 6.69 | N | 10.63 |
|---|---|---|---|---|---|---|
| Found: | | 63.69 | | 6.86 | | 10.21 |

(80) 1-[3-(4-amidino-phenyl)-propionyl]-6-(N-pentanoyl-N-benzyl-amino)-1,2,3,4-tetrahydro-quinoline-hydrochloride
Yield: 63% of theory,
Prepared from the compound prepared according to Example 11(10)
$C_{31}H_{36}N_4O_2 \times HCl \times H_2O$ (551.15)

| Calc.: | C | 67.55 | H | 7.13 | N | 10.16 |
|---|---|---|---|---|---|---|
| Found: | | 66.99 | | 7.30 | | 10.08 |

(81) 1-[3-(4-amidino-phenyl)-propionyl]-6-[N-(2-ethoxycarbonylethylcarbonyl)-benzylamino]-1,2,3,4-tetrahydro-quinoline-hydrochloride
Prepared from the compound prepared according to Example 11(11)
Yield: 66% of theory,
$C_{32}H_{36}N_4O_4 \times HCl \times 0.5\ H_2O$ (586.16)

| Calc.: | C | 65.57 | H | 6.53 | N | 9.55 |
|---|---|---|---|---|---|---|
| Found: | | 65.07 | | 6.34 | | 9.79 |

(82) 1-[3-(4-amidino-phenyl)-propionyl]-6-(N-methanesulphonyl-benzylamino)-1,2,3,4-tetrahydro-quinoline-hydrochloride
Prepared from the compound prepared according to Example 10(22)
Yield: 60% of theory,
$C_{27}H_{30}N_4O_3S \times HCl$ (527.12)

| Calc.: | C | 61.52 | H | 5.92 | N | 10.62 |
|---|---|---|---|---|---|---|
| Found: | | 61.18 | | 6.26 | | 10.45 |

(83) 1-[3-(4-amidino-phenyl)-propionyl]-6-[N-(ethylamino-carbonylmethyl)-benzylamino]-1,2,3,4-tetrahydro-quinolinehydrochloride
Prepared from the compound prepared according to Example 14
Yield: 57% of theory,
$C_{30}H_{35}N_5O_2 \times HCl \times 2\ H_2O$ (570.14)

| Calc.: | C | 63.20 | H | 7.00 | N | 12.28 |
|---|---|---|---|---|---|---|
| Found: | | 63.06 | | 7.00 | | 11.61 |

(84) 1-[3-(4-amidino-phenyl)-propionyl]-6-[N-(N,N-dipropyl-aminocarbonylmethyl)-benzylamino]-1,2,3,4-tetrahydroquinoline-hydrochloride
Prepared from the compound prepared according to Example 14(1)
Yield: 62% of theory,
$C_{34}H_{43}N_5O_2 \times HCl \times H_2O$ (608.25)

| Calc.: | C | 67.14 | H | 7.62 | N | 11.51 |
|---|---|---|---|---|---|---|
| Found: | | 67.72 | | 7.67 | | 11.17 |

(85) 1-[3-(4-amidino-phenyl)-propionyl]-6-[N-(benzylaminocarbonylmethyl)-benzylamino]-1,2,3,4-tetrahydro-quinoline-hydrochloride
Prepared from the compound prepared according to Example 15(2)
Yield: 50% of theory,
$C_{35}H_{37}N_5O_2 \times HCl \times 2\ H_2O$ (632.21)

| Calc.: | C | 66.49 | H | 6.69 | N | 11.07 |
|---|---|---|---|---|---|---|
| Found: | | 66.65 | | 6.78 | | 10.56 |

(86) 1-[3-(4-amidino-phenyl)-propionyl]-6-[N-(phenylamino-carbonylmethyl)-benzylamino]-1,2,3,4-tetrahydro-quinoline-hydrochloride
Prepared from the compound prepared according to Example 15(3)
Yield: 78% of theory, $C_{34}H_{35}N_5O2 \times HCl \times H_2O$ (600.19)

| Calc.: | C | 68.04 | H | 6.38 | N | 11.66 |
|---|---|---|---|---|---|---|
| Found: | | 67.92 | | 6.58 | | 11.37 |

(87) 1-[3-(4-amidino-phenyl)-propionyl]-6-phenyl-aminosulphonyl-1,2,3,4-tetrahydro-quinoline-hydrochloride Prepared from the compound prepared according to Example 16b)

Yield: 21% of theory, $C_{25}H_{26}NO_3S \times 2\ HCl \times H_2O$ (553.51)

| Calc.: | C | 54.25 | H | 5.46 | N | 10.12 |
|---|---|---|---|---|---|---|
| Found: | | 54.52 | | 5.54 | | 10.16 |

(88) 1-[3-(4-amidino-phenyl)-propionyl]-6-benzyl-aminosulphonyl-1,2,3,4-tetrahydro-quinoline-hydrochloride Prepared from the compound prepared according to Example 16(1)

Yield: 28% of theory, $C_{26}H_{28}N_4O_3S \times HCl \times 2\ H_2O$ (549.09)

| Calc.: | C | 56.87 | H | 6.06 | N | 10.20 |
|---|---|---|---|---|---|---|
| Found: | | 57.40 | | 5.74 | | 9.94 |

(89) 1-[3-(4-amidino-phenyl)-propionyl]-6-phenylsulphonyl-1,2,3,4-tetrahydro-quinoline-hydrochloride Prepared from the compound prepared according to Example 16(2)

Yield: 48% of theory, $C_{25}H_{25}N_3O_3S \times HCl \times H_2O$ (502.01)

| Calc.: | C | 59.81 | H | 5.62 | N | 8.37 |
|---|---|---|---|---|---|---|
| Found: | | 59.94 | | 5.59 | | 8.26 |

(90) 1-[3-(4-amidino-phenyl)-propionyl]-6-benzoyl-1,2,3,4-tetrahydro-quinoline-hydrochloride Prepared from the compound prepared according to Example 16(3)

Yield: 56% of theory, $C_{26}H_{25}N_3O_2 \times HCl \times 1.5\ H_2O$ (474.95)

| Calc.: | C | 65.75 | H | 6.15 | N | 8.85 |
|---|---|---|---|---|---|---|
| Found: | | 66.12 | | 5.93 | | 9.05 |

(91) 1-[3-(4-amidino-phenyl)-propionyl]-6-(2,2-diphenyl-ethylamino)-1,2,3,4-tetrahydro-quinoline-hydrochloride Prepared from the compound prepared according to Example 14(4)

Yield: 82% of theory, $C_{33}H_{34}N_4O \times HCl \times 2\ H_2O$ (575.16)

| Calc.: | C | 68.91 | H | 6.81 | N | 9.74 |
|---|---|---|---|---|---|---|
| Found: | | 67.62 | | 6.82 | | 9.26 |

(92) 1-[3-(4-amidino-phenyl)-propionyl]-6-(N-ethoxycarbonylmethyl-2,2-diphenylethylamino)-1,2,3,4-tetrahydro-quinoline-hydrochloride Prepared from the compound prepared according to Example 6(4)

Yield: 84% of theory, $C_{37}H_{40}N_4O_3 \times HCl \times H_2O$ (643.25)

| Calc.: | C | 68.62 | H | 6.73 | N | 8.71 |
|---|---|---|---|---|---|---|
| Found: | | 69.13 | | 6.75 | | 8.83 |

(93) 1-[3-(4-amidino-phenyl)-propionyl]-6-(2-oxo-pyrrolidino)-1,2,3,4-tetrahydro-quinoline-hydrochloride Prepared from the compound prepared according to Example 11(12)

Yield: 59% of theory, $C_{23}H_{26}N_4O_2 \times HCl \times 1.5\ H_2O$ (453.98)

| Calc.: | C | 60.84 | H | 6.66 | N | 12.34 |
|---|---|---|---|---|---|---|
| Found: | | 60.86 | | 6.88 | | 11.45 |

(94) 1-[3-(4-amidino-phenyl)-propionyl]-6-(2-oxo-piperidino)-1,2,3,4-tetrahydro-quinoline-hydrochloride Prepared from the compound prepared according to Example 11(13)

Yield: 59% of theory, $C_{24}H_{28}N_4O_2 \times HCl \times 1.5\ H_2O$ (468.01)

| Calc.: | C | 61.59 | H | 6.90 | N | 11.97 |
|---|---|---|---|---|---|---|
| Found: | | 61.78 | | 7.02 | | 11.46 |

(95) 1-[N-(4-amidino-benzyl)-methylaminocarbonyl]-6-phenyl-sulphonylamino-1,2,3,4-tetrahydro-quinoline-hydrochloride Prepared from the compound prepared according to Example 17

Yield: 59% of theory, $C_{25}H_{27}N_5O_3S$ (477.60)

mass spectrum: FAB-MS: $(M+H)^+=478$

EXAMPLE 25

1-[3-(4-amidino-phenyl)-propionyl]-6-[N-(3-methoxycarbonyl-propyl)-naphth-1-yl-sulphonylamino]-1,2,3,4-tetrahydro-quinoline 0.89 g of 1-[3-(4-benzyloxycarbonylamidino-phenyl)-propionyl]-6-[N-(3-methoxycarbonylpropyl)-naphth-1-yl-sulphonylamino]-1,2,3,4-tetrahydro-quinoline (see Example 7(3)) are dissolved in 30 ml of methanol and 1.1 ml of 1 N hydrochloric acid and hydrogenated over palladium/charcoal at ambient temperature for 3 hours with 3 bars of hydrogen. Then the catalyst is filtered off, the solution is evaporated down and the residue is chromatographed over a silica gel column with methylene chloride/methanol (8.5:1.5). The main fraction is concentrated by rotary evaporation and material obtained is dried.

Yield: 0.39 g (53% of theory),
$C_{34}H_{36}N_4O_5S \times HCl \times H_2O$ (667.23)

| Calc.: | C | 61.21 | H | 5.89 | N | 8.40 |
|---|---|---|---|---|---|---|
| Found: | | 61.50 | | 5.98 | | 8.52 |

The following are prepared analogously:

(1) 1-[3-(4-amidino-phenyl)-propionyl]-6-[N-(1-ethoxycarbonyl-ethyl)-naphth-1-yl-sulphonylamino]-1,2,3,4-tetrahydro-quinoline-hydrochloride
Yield: 63% of theory,
$C_{34}H_{36}N_4O_5S \times HCl \times H_2O$ (667.23)

| Calc.: | C | 61.21 | H | 5.89 | N | 8.40 |
|---|---|---|---|---|---|---|
| Found: | | 60.46 | | 5.71 | | 8.18 |

(2) 1-[3-(4-amidino-phenyl)-propionyl]-6-[N-(naphth-1-yl-sulphonyl-methylamino]-1,2,3,4-tetrahydro-quinoline-hydrochloride
Yield: 70% of theory,
$C_{30}H_{30}N_4O_3S \times HCl \times 1.5\ H_2O$ (590.15)

| Calc.: | C | 61.06 | H | 5.81 | N | 9.49 |
|---|---|---|---|---|---|---|
| Found: | | 60.73 | | 5.74 | | 9.51 |

(3) 1-[3-(4-amidino-phenyl)propionyl]-6-[N-(naphth-1-yl-sulphonyl-benzylamino]-1,2,3,4-tetrahydro-quinoline-hydrochloride
Yield: 81% of theory,
$C_{36}H_{34}N_4O_3S \times HCl \times 1.5\ H_2O$ (666.25)

| Calc.: | C | 64.90 | H | 5.75 | N | 8.41 |
|---|---|---|---|---|---|---|
| Found: | | 65.09 | | 5.78 | | 8.44 |

(4) 1-[3-(4-amidino-phenyl)-propionyl]-6-[N-(naphth-1-yl-sulphonyl)-N-(2-morpholinoethyl)-amino]-1,2,3,4-tetrahydro-quinoline-hydrochloride
Prepared from 1-[3-(4-benzyloxycarbonylamidino-phenyl)-propionyl]-6-[N-(naphth-1-yl-sulphonyl)-N-(2-morpholinoethyl)-amino]-1,2,3,4-tetrahydro-quinoline
Yield: 40% of theory,
$C_{35}H_{37}N_5O_5S \times HCl \times 2.5\ H_2O$ (721.28)

| Calc.: | C | 58.28 | H | 6.01 | N | 9.71 |
|---|---|---|---|---|---|---|
| Found: | | 58.21 | | 5.88 | | 9.48 |

(5) 1-[3-(4-amidino-phenyl)-propionyl]-6-[N-(naphth-1-yl-sulphonyl)-N-(ethoxycarbonylmethyl)-amino]-1,2,3,4-tetrahydro-quinoline-hydrochloride
Yield: 70% of theory,
$C_{33}H_{34}N_4O_5S \times HCl \times H_2O$ (653.20)

| Calc.: | C | 60.68 | H | 5.71 | N | 8.58 |
|---|---|---|---|---|---|---|
| Found: | | 60.01 | | 5.69 | | 8.54 |

(6) 1-[3-(4-amidino-phenyl)propionyl]-6-[N-(naphth-1-yl-sulphonyl)-N,N-(di(methoxycarbonylmethyl)-aminocarbonyl-methyl)-amino]-1,2,3,4-tetrahydro-quinoline Prepared from the compound prepared according to Example 7(8)
Yield: 67% of theory,
$C_{37}H_{39}N_5O_8S \times HCl \times H_2O$ (768.29)

| Calc.: | C | 57.84 | H | 5.51 | N | 9.12 |
|---|---|---|---|---|---|---|
| Found: | | 57.49 | | 5.52 | | 9.07 |

EXAMPLE 26

1-[3-(4-amidino-phenyl)-propionyl]-6-(2,4,6-trimethyl-benzenesulphonylamino)-1,2,3,4-tetrahydro-quinoline-hydroiodide 1.32 g (2.7 mmol) of 1-[3-(4-cyano-phenyl)-propionyl]-6-(2,4,6-trimethyl-benzenesulphonylamino)-1,2,3,4-tetrahydro-quinoline (see Example 10(13)) are dissolved in 20 ml of pyridine and combined with 2 ml of triethylamine. Then 3.6 g of hydrogen sulphide are piped in whilst cooling with ice and the solution is stirred overnight. Then nitrogen is blown through the solution for 2 hours and the solution is concentrated by evaporation. The residue is taken up in and 3 ml of concentrated hydrochloric acid and extracted 3 times with ethyl acetate. The organic phase is dried and concentrated by rotary evaporation. The crude thioamide derivative is dissolved in 50 ml of acetone and stirred for 2.5 hours with 8 ml of methyliodide at 45° C. and finally concentrated by rotary evaporation. Then the residue is dissolved in 50 ml of methanol or ethanol, combined with 3 g ammonium acetate, and stirred for 6 hours at 45° C. and then concentrated by evaporation. The amidine formed is purified over a silica gel column.

Yield: 46% of theory,
Melting point: from 124° C.
$C_{28}H_{32}N_4O_3S \times HI$ (632.57)

| Calc.: | C | 53.17 | H | 5.26 | N | 8.86 |
|---|---|---|---|---|---|---|
| Found: | | 51.05 | | 5.44 | | 8.57 |

The following are prepared analogously:
(1) 1-[3-(4-amidino-phenyl)-propionyl]-6-[N-(quinoline-8-sulphonyl)-N-ethoxycarbonylmethyl)-amino]-1,2,3,4-tetrahydro-quinoline-hydroiodide
Prepared from 1-[3-(4-cyano-phenyl)-propionyl]-6-[N-(quinoline-8-sulphonyl)-N-ethoxycarbonylmethyl)-amino]-1,2,3,4-tetrahydro-quinoline (see Example 10(20)).
Yield: 48% of theory,
$C_{32}H_{33}JN_5O_5S \times HI \times 0.5\ H_2O$ (736.63)

| Calc.: | C | 52.18 | H | 4.79 | N | 9.51 |
|---|---|---|---|---|---|---|
| Found: | | 52.13 | | 4.90 | | 9.39 |

(2) 1-[3-(4-amidino-phenyl)-propionyl]-6-[N-(isoquinoline-5-sulphonyl)-N-(ethoxycarbonylmethyl)-amino]-1,2,3,4-tetrahydro-quinoline-hydroiodide
Prepared from 1-[3-(4cyano-phenyl)-propionyl]-6-[N-(isoquinoline-5-sulphonyl)-N-(ethoxycarbonylmethyl)-amino]-1,2,3,4-tetrahydro-quinoline (see Example 7)
Yield: 17% of theory, $C_{32}H_{33}N_5O_5S \times HI \times H_2O$ (745.63)

| | | | | | | |
|---|---|---|---|---|---|---|
| Calc.: | C | 51.55 | H | 4.87 | N | 9.39 |
| Found: | | 51.30 | | 4.96 | | 8.87 |

(3) 1-[3-(4-amidino-phenyl)propionyl]-6-[N-(phenylmethanesulphonyl)-N-(ethoxycarbonylmethyl)-amino]-1,2,3,4-tetrahydro-quinoline-hydroiodide Prepared from the compound prepared according to Example 10(24)
Yield: 57% of theory,
Melting point: sinters from 110° C.
$C_{30}H_{34}N_4O_5S \times HI \times 0.5\ H_2O$ (699.61)

| | | | | | | |
|---|---|---|---|---|---|---|
| Calc.: | C | 51.50 | H | 5.19 | N | 8.01 |
| Found: | | 51.52 | | 5.27 | | 7.79 |

(4) 1-[3-(4-amidino-phenyl)propionyl]-6-[N-(n-butyl-sulphonyl)-N-(ethoxycarbonylmethyl)-amino]-1,2,3,4-tetrahydro-quinoline-hydroiodide Prepared from the compound prepared according to Example 7(1)
Yield: 56% of theory,
$C_{27}H_{36}N_4O_5S \times HI$ (656.59)

| | | | | | | |
|---|---|---|---|---|---|---|
| Calc.: | C | 49.39 | H | 5.68 | N | 8.53 |
| Found: | | 48.88 | | 5.77 | | 8.38 |

(5) 1-[(4-amidino-phenoxy)-acetyl]-6-[N-(1-naphthylsulphonyl)-ethoxycarbonylmethylamino]-1,2,3,4-tetrahydro-quinoline-hydroiodide Prepared from the compound prepared according to Example 9(27)
Yield: 48% of theory,
$C_{32}H_{32}N_4O_6S \times HI$ (728.59)

| | | | | | | |
|---|---|---|---|---|---|---|
| Calc.: | C | 52.75 | H | 4.56 | N | 7.69 |
| Found: | | 52.33 | | 4.79 | | 7.52 |

(6) 1-[3-(4-amidino-phenyl)-propionyl]-6-(N-benzoyl-ethoxy-carbonylmethylamino]-1,2,3,4-tetrahydro-quinoline-hydroiodide Prepared from the compound prepared according to Example 11
Yield: 35% of theory,
Melting point: 130° C. with decomposition
$C_{30}H_{32}N_4O_4 \times HI \times H_2O$ (658.54)

| | | | | | | |
|---|---|---|---|---|---|---|
| Calc.: | C | 54.72 | H | 5.36 | N | 8.51 |
| Found: | | 55.04 | | 5.45 | | 8.41 |

(7) 1-[3-(4-amidino-phenyl)-propionyl]-6-[N-(naphtho-1-yl)-exthoxycarbonylmethylamino]-1,2,3,4-tetrahydro-quinoline-hydroiodide Prepared from the compound prepared according to Example 11(1)
Yield: 60% of theory, $C_{34}H_{34}N_4O_4 \times HI \times H_2O$ (708.60)

| | | | | | | |
|---|---|---|---|---|---|---|
| Calc.: | C | 57.63 | H | 5.26 | N | 17.81 |
| Found: | | 57.59 | | 5.33 | | 18.87 |

(8) 1-[3-(4-amidino-phenyl)-propionyl]-6-[N-(2-naphthyl-sulphonyl)-ethoxycarbonylmethylamino]-1,2,3,4-tetrahydro-quinoline-hydroiodide Prepared from the compound prepared according to Example 10(21)
Yield: 51% of theory,
Melting point: decomposition from 120° C.
$C_{33}H_{34}N_4O_5S \times HI$ (726.64)

| | | | | | | |
|---|---|---|---|---|---|---|
| Calc.: | C | 54.55 | H | 4.86 | N | 7.71 |
| Found: | | 53.63 | | 4.97 | | 7.63 |

(9) 1-[3-(4-amidino-3-methyl-phenyl)-propionyl]-6-phenylsulphonylamino-1,2,3,4-tetrahydro-quinoline-hydroiodide Prepared from the compound prepared according to Example 9(30)
Yield: 10% of theory.
$R_f$ value: 0.48 (silica gel; methylene chloride/ethanol=9:1)

EXAMPLE 27

1-[3-[4-(N-methoxycarbonyl-amidino)phenyl]-propionyl]-6-phenyl-sulphonamido-1,2,3,4-tetrahydro-quinoline 630 mg of 1-[3-(4-amidino-phenyl)propionyl]-6-phenyl-sulpho-namido-1,2,3,4-tetrahydro-quinoline-hydrochloride are dissolved in 10 ml of tetrahydrofuran and 1 ml of water, then 260 mg of sodium carbonate are added. Finally, 120 mg of methyl chloroformate in 1.5 ml of tetrahydrofuran are added dropwise and stirring is continued for 4 hours. Then the mixture is combined with 20 ml of water and 30 ml of ethyl acetate. The organic phase is then separated off, washed with water, dried and concentrated by evaporation. The residue is chromatographed over a silica gel column with an ethyl acetatelmethylene chloride mixture (7:3).
Yield: 350 mg (56% of theory),
Melting point: foam
$C_{27}H_{29}N_4O_5S$ (520.61)

| | | | | | | | | |
|---|---|---|---|---|---|---|---|---|
| Calc.: | C | 62.29 | H | 5.42 | N | 10.76 | S | 6.16 |
| Found: | | 61.85 | | 5.61 | | 10.00 | | 6.40 |

EXAMPLE 28

1-[3-(4-amidino-phenyl)propionyl]-6-methylamino-1,2,3,4-tetrahydro-quinoline-hydrochloride and
1-[3-(4-amidino-phenyl)propionyl]-6-(N-methyl-phenyl-sulphonamido)-1,2,3,4-tetrahydro-quinoline-hydrochloride Prepared analogously to Example 24 from 1-[3-(4-cyano-phenyl)propionyl]-6-(N-methyl-phenylsulphonamido)-1,2,3,4-tetrahydroquinoline (see Example 9(8)) and subsequent chromatographic separation over a silica gel column using methylene chloride/methanol (8:2).

a) 1-[3-(4amidino-phenyl)propionyl]-6-methylamino-1,2,3,4-tetrahydro-quinoline-hydrochloride
Yield: 25% of theory, Melting point: sinters from 130° C.
$C_{20}H_{24}N_4O_3$ (390.92)×HCl (390.92)

| Calc.: | C | 61.45 | H | 6.96 | N | 14.33 |
|---|---|---|---|---|---|---|
| Found: |  | 61.27 |  | 6.91 |  | 14.05 | b) 1-[3-(4-amidino-phenyl)propionyl]-6-(N-methyl-phenyl-sulphonamido)-1,2,3,4-tetrahydro-quinoline-benzenesulphonate
Yield: 6% of theory,
Melting point: sintering from 90° C.
$C_{26}H_{28}N_4O_3S \times C_6H_5SO_3H \times H_2O$ (652.79)

| Calc.: | C | 58.88 | H | 5.56 | N | 8.58 |
|---|---|---|---|---|---|---|
| Found: |  | 58.53 |  | 5.37 |  | 7.94 |

The following are prepared analogously:
(1a) 1-[3-(4-amidino-phenyl)propionyl]-6-(2-phenylethylamino)-1,2,3,4-tetrahydro-quinoline-hydrochloride
Prepared from the compound prepared according to Example 9(11)
Yield: 22% of theory,
Melting point: from 90° C.
$C_{27}H_{30}N_4O \times 2.5$ HCl×2 $H_2O$ (553.76)

| Calc.: | C | 58.56 | H | 6.64 | N | 10.12 |
|---|---|---|---|---|---|---|
| Found: |  | 56.69 |  | 6.30 |  | 9.64 |

(1b) 1-[3-(4-amidino-phenyl)propionyl]-6-[N-(2-phenylethyl)-phenylsulphonamido]-1,2,3,4-tetrahydro-quinoline-hydrochloride
Yield: 41% of theory,
Melting point: from 105° C.
$C_{33}H_{39}N_4O_3S \times HCl \times 0.5$ $H_2O$ (612.20)

| Calc.: | C | 64.75 | H | 5.93 | N | 9.15 | S | 5.24 |
|---|---|---|---|---|---|---|---|---|
| Found: |  | 64.66 |  | 6.04 |  | 9.01 |  | 5.51 |

(2a) 1-[3-(4-amidino-phenyl)propionyl]-6-(N-ethoxycarbonyl-methylamino)-1,2,3,4-tetrahydro-quinoline-hydrochloride
Prepared from the compound prepared according to Example 9(10)
Yield: 13.0% of theory,
Melting point: from 135° C. (decomp.)
$C_{23}H_{28}N_4O_3 \times HCl \times 7.5$ $H_2O$ (471.99)

| Calc.: | C | 58.53 | H | 6.83 | N | 11.87 |
|---|---|---|---|---|---|---|
| Found: |  | 58.44 |  | 6.44 |  | 11.58 |

(2b) 1-[3-(4-amidino-phenyl)propionyl]-6-(N-ethoxycarbonylmethyl-phenylsulphonamido)-1,2,3,4-tetrahydro-quinoline-benzenesulphonate
Yield: 21% of theory,
Melting point: from 105° C.
$C_{29}H_{32}N_4O_5S \times 0.5$ $C_6H_5SO_3H \times H_2O \times 0.5$ HCl (664.00)

| Calc.: | C | 57.83 | H | 5.69 | N | 8.44 |
|---|---|---|---|---|---|---|
| Found: |  | 56.96 |  | 5.60 |  | 8.47 |

EXAMPLE 29
1-[3-(4-amidino-phenyl)propionyl]-6-(N-carboxymethyl-phenyl-sulphonamido)-1,2,3,4-tetrahydro-quinoline 370 mg of 1-[3-(4-amidino-phenyl)propionyl]-6-(N-ethoxycarbonylmethyl-phenylsulphonamido)-1,2,3,4-tetrahydro-quinoline are dissolved in 5 ml of ethanol and stirred overnight with 1.6 ml of 1N sodium hydroxide solution. Then the mixture is neutralised with hydrochloric acid, concentrated by evaporation and the residue is chromatographed with methanol over a silica gel column.
Yield: 190 mg (65% of theory),
$C_{27}H_{28}N_4O_5S$ (520.61)

| Calc.: | C | 62.29 | H | 5.42 | N | 10.76 |
|---|---|---|---|---|---|---|
| Found: |  | 61.13 |  | 5.59 |  | 10.48 |

EXAMPLE 30
1-[3-(4-aminomethyl-phenyl)propionyl]-6-phenylsulphonamido-1,2,3,4-tetrahydro-quinoline 900 mg of 1-[3-(4-cyano-phenyl)propionyl]-6phenyl-sulphonamido-1,2,3,4-tetrahydro-quinoline are hydrogenated in 20 ml of methanolic ammonia solution at 3 bars for 17 hours over Raney nickel. Then the catalyst is removed by suction filtering, the mixture is concentrated by evaporation, the residue obtained is dissolved in water and made alkaline. It is extracted with methylene chloride, the organic phase is separated off, dried and concentrated by evaporation in vacuo.
Yield: 0.6 g (67% of theory),
Melting point: 130–132° C.
$C_{25}H_{27}N_3O_3S$ (449.58)

| Calc.: | C | 66.79 | H | 6.05 | N | 9.35 | S | 7.13 |
|---|---|---|---|---|---|---|---|---|
| Found: |  | 66.73 |  | 6.16 |  | 9.44 |  | 7.12 |

The following are prepared analogously:
(1) 1-[3-(4-aminomethyl-phenyl)propionyl]-6-(1-naphthyl-sulphonamido)-1,2,3,4-tetrahydro-quinoline
(2) 1-[3-(4-aminomethyl-phenyl)propionyl]-6-(4-fluoro-phenyl-sulphonamido)-1,2,3,4-tetrahydro-quinoline
(3) 1-[3-(4-aminomethyl-phenyl)propionyl]-6-butylsulphonamido-1,2,3,4-tetrahydro-quinoline
(4) 1-[3-(4-aminomethyl-phenyl)propionyl]-6-(N-methyl-phenyl-sulphonamido)-1,2,3,4-tetrahydro-quinoline
(5) 1-[3-(4-aminomethyl-phenyl)propionyl]-6-benzyl-sulphonamido-1,2,3,4-tetrahydro-quinoline
(6) 1-[3-(4-aminomethyl-phenyl)propionyl]-6-benzoylamino-1,2,3,4-tetrahydro-quinoline

EXAMPLE 31
1-[3-(4-amidino-phenyl)-propionyl]-6-[N-(quinoline-8-sulphonyl)-hydroxycarbonylmethyl]-1,2,3,4-tetrahydro-quinoline 590 mg of 1-[3-(4-amidino-phenyl)-propionyl]-6-[N-(quinoline-8-sulphonyl)-N-ethoxycarbonylmethyl-amino]-

1,2,3,4-tetrahydro-quinoline (see Example 26(1)) are dissolved in 15 ml of ethanol and 2.4 ml of 1N sodium hydroxide solution and stirred for 2.5 hours at ambient temperature. Then the mixture is neutralised with 0.1N hydrochloric acid and concentrated by evaporation. The residue is stirred with water and ethanol and dried.

Yield: 200 mg (41% of theory),
Melting point: 215–217° C. with decomposition
$C_{30}H_{29}N_5O_5S \times 1.5\ H_2O$ (598.68)

| Calc.: | C | 60.19 | H | 5.39 | N | 11.70 |
|---|---|---|---|---|---|---|
| Found: |   | 59.70 |   | 5.45 |   | 11.34 |

The following are prepared analogously:

(1) 1-[3-(4-amidino-phenyl)-propionyl]-6-[N-(isoquinoline-5-sulphonyl)-hydroxycarbonylmethylamino]-1,2,3,4-tetrahydro-quinoline
Prepared from the compound prepared according to Example 26(2)
Yield: 45% of theory,
Melting point: 213–215° C. with decomposition
$C_{30}H_{29}N_5O_5S \times 1.5\ H_2O$ (598.68)

| Calc.: | C | 60.19 | H | 5.39 | N | 11.70 |
|---|---|---|---|---|---|---|
| Found: |   | 60.20 |   | 5.39 |   | 11.37 |

(2) 1-[3-(4-amidino-phenyl)-propionyl]-6-[N-(phenylmethanesulphonyl)-hydroxycarbonylmethylamino]-1,2,3,4-tetrahydro-quinoline
Prepared from the compound prepared according to Example 26(3)
Yield: 81% of theory,
$C_{28}H_{30}N_4O_5S \times H_2O$ (552.64)

| Calc.: | C | 60.85 | H | 5.84 | N | 10.14 |
|---|---|---|---|---|---|---|
| Found: |   | 61.25 |   | 5.94 |   | 10.16 |

(3) 1-[3-(4-amidino-phenyl)-propionyl]-6-[N-(n-butylsulphonyl)-hydroxycarbonylmethylamino]-1,2,3,4-tetrahydro-quinoline
Prepared from the compound prepared according to Example 26(4)
Yield: 68% of theory,
$C_{25}H_{32}N_4O_5S \times 0.5\ H_2O$ (509.63)

| Calc.: | C | 58.92 | H | 6.53 | N | 10.99 |
|---|---|---|---|---|---|---|
| Found: |   | 58.82 |   | 6.61 |   | 10.96 |

(4) 1-[(4-amidino-phenoxy)-acetyl]-6-[N-(1-naphthylsulphonyl)-hydroxycarbonylmethylamino]-1,2,3,4-tetrahydro-quinoline-hydrochloride
Prepared from the compound prepared according to Example 26(5)
Yield: 59% of theory,
$C_{30}H_{28}N_4O_6S \times HCl \times 0.5\ H_2O$ (618.14)

| Calc.: | C | 57.17 | H | 5.18 | N | 8.51 |
|---|---|---|---|---|---|---|
| Found: |   | 57.45 |   | 4.82 |   | 8.93 |

(5) 1-[3-(4-amidino-phenyl)-propionyl]-6-(N-benzoyl-hydroxycarbonylmethylamino]-1,2,3,4-tetrahydro-quinoline
Prepared from the compound prepared according to Example 26(6)
Yield: 31% of theory,
$C_{28}H_{28}N_4O_4 \times H_2O$ (658.54)

| Calc.: | C | 66.92 | H | 6.02 | N | 11.15 |
|---|---|---|---|---|---|---|
| Found: |   | 66.23 |   | 6.18 |   | 10.98 |

(6) 1-[3-(4-amidino-phenyl)-propionyl]-6-[N-(1-naphthoyl)-hydroxycarbonylmethlylamino]-1,2,3,4-tetrahydro-quinoline
Prepared from the compound prepared according to Example 26(7)
$C_{32}H_{30}N_4O_4 \times H_2O$ (552.63)

| Calc.: | C | 69.55 | H | 5.84 | N | 10.14 |
|---|---|---|---|---|---|---|
| Found: |   | 68.84 |   | 5.84 |   | 9.93 |

(7) 1-[3-(4-amidino-2-(2-hydroxycarbonylethylcarbonylamino)-phenyl)-propionyl]-6-phenylsulphonylamino-1,2,3,4-tetrahydro-quinoline-hydrochloride
Prepared from the compound prepared according to Example 24(47)
Yield: 87% of theory, (8) 1-[3-(4-amidino-phenyl)-propionyl]-6-[N-(naphth-2-yl-sulphonyl)-ethoxycarbonylmethylamino]-1,2,3,4-tetrahydro-quinoline
Yield: 82% of theory,
$C_{31}H_{30}N_4O_5S \times 1.5\ H_2O$ (597.70)

| Calc.: | C | 62.30 | H | 5.57 | N | 9.37 |
|---|---|---|---|---|---|---|
| Found: |   | 62.15 |   | 5.47 |   | 9.39 |

(9) 1-[3-(4-amidino-phenyl)-propionyl]-6-[N-(naphth-1-yl-sulphonyl)-N-(3-hydroxycarbonylpropyl)-amino]-1,2,3,4-tetrahydro-quinoline
Prepared from the compound prepared according to Example 25
Yield: 48% of theory,
$C_{33}H_{34}N_4O_5S$ (598.72)
mass spectrum: FAS-MS: (M+H)$^+$=599

(10) 1-[3-(4-amidino-phenyl)-propionyl]-6-[N-(naphth-1-yl-sulphonyl)-N-(1-hydroxycarbonylethyl)-amino]-1,2,3,4-tetrahydro-quinoline-hydrochloride
Prepared from the compound prepared according to Example 25(1)
Yield: 80% of theory, $C_{32}H_{32}N_4O_5S \times HCl \times 1.5\ H_2O$ (611.72)

| Calc.: | C | 62.83 | H | 5.77 | N | 9.16 |
|---|---|---|---|---|---|---|
| Found: | | 62.97 | | 5.73 | | 9.16 |

(11) 1-[3-(4-amidino-phenyl)-propionyl]-6-[N-(naphth-1-yl-sulphonyl)-hydroxycarbonylmethylamino]-1,2,3,4-tetrahydro-quinoline-hydrochloride Prepared from the compound prepared according to Example 25(2)

Yield: 77% of theory, $C_{31}H_{30}N_4O_5S \times HCl \times H_2O$ (625.15)

| Calc.: | C | 63.25 | H | 5.48 | N | 9.52 |
|---|---|---|---|---|---|---|
| Found: | | 63.45 | | 5.83 | | 9.76 |

(12) 1-[3-(4-amidino-phenyl)-propionyl]-6-[N-(naphth-1-yl-sulphonyl)-N-(N,N-di(hydroxycarbonylmethyl)-aminocarbonyl)-amino]-1,2,3,4-tetrahydro-quinoline-hydrochloride Prepared from the compound prepared according to Example 25(6)

Yield: 91% of theory, $C_{35}H_{35}N_5O_8S \times H_2O$ (703.78)

| Calc.: | C | 59.73 | H | 5.30 | N | 9.95 |
|---|---|---|---|---|---|---|
| Found: | | 59.92 | | 5.25 | | 9.97 |

(13) 1-[3-(4-amidino-phenyl)-propionyl]-6-(N-hydroxycarbonylmethyl-phenylamino)-1,2,3,4-tetrahydro-quinoline-hydrochloride Prepared from the compound prepared according to Example 24(62)

Yield: 26% of theory, $C_{28}H_{28}N_4O_4 \times HCl \times 1.5\ H_2O$ (548.02)

| Calc.: | C | 61.36 | H | 5.89 | N | 10.12 |
|---|---|---|---|---|---|---|
| Found: | | 61.34 | | 5.67 | | 9.85 |

(14) 1-[3-(4-amidino-phenyl)-propionyl]-6-(N-hydroxycarbonylmethyl-cyclohexylaminocarbonyl)-1,2,3,4-tetrahydro-quinoline-hydrochloride Prepared from the compound prepared according to Example 24(66)

Yield: 58% of theory, $C_{28}H_{34}N_4O_4 \times HCl \times 0.5\ H_2O$ (536.05)

| Calc.: | C | 62.74 | H | 6.77 | N | 10.45 |
|---|---|---|---|---|---|---|
| Found: | | 63.24 | | 6.78 | | 9.76 |

(15) 1-[3-(4-amidino-phenyl)-propionyl]-6-(2-hydroxycarbonylpyrrolidino)-1,2,3,4-tetrahydro-quinoline-hydrochloride Prepared from the compound prepared according to Example 24(67)

Yield: 35% of theory, $C_{25}H_{28}N_4O_4 \times HCl \times H_2O$ (502.96)

| Calc.: | C | 59.70 | H | 6.21 | N | 11.16 |
|---|---|---|---|---|---|---|
| Found: | | 60.02 | | 6.31 | | 10.17 |

(16) 1-[3-(4-amidino-phenyl)-propionyl]-6-(2hydroxycarbonylpiperidino)-1,2,3,4-tetrahydro-quinoline-hydrochloride Prepared from the compound prepared according to Example 24(68)

Yield: 46% of theory, $C_{26}H_{30}N_4O_4 \times HCl \times H_2O$ (517.03)

| Calc.: | C | 60.40 | H | 6.43 | N | 10.84 |
|---|---|---|---|---|---|---|
| Found: | | 60.73 | | 6.35 | | 9.94 |

(17) 1-[3-(4-amidino-phenyl)-propionyl]-6-(3-hydroxycarbonylpiperidino)-1,2,3,4-tetrahydro-quinoline-hydrochloride Prepared from the compound prepared according to Example 24(69)

Yield: 47% of theory, $C_{26}H_{30}N_4O_4 \times HCl \times H_2O$ (517.03)

| Calc.: | C | 60.40 | H | 6.43 | N | 10.84 |
|---|---|---|---|---|---|---|
| Found: | | 61.28 | | 6.50 | | 10.39 |

(18) 1-[3-(4-amidino-phenyl)-propionyl]-6-[N-(naphthalin-2-ylmethyl)-hydroxycarbonylmethylamino]-1,2,3,4-tetrahydro-quinoline-hydrochloride Prepared from the compound prepared according to Example 24(77)

Yield: 70% of theory, $C_{32}H_{32}N_4O_3 \times HCl$ (557.13)

| Calc.: | C | 66.98 | H | 5.96 | N | 10.05 |
|---|---|---|---|---|---|---|
| Found: | | 67.81 | | 6.45 | | 8.86 |

(19) 1-[3-(4-amidino-phenyl)-propionyl]-6-[N-(naphth-1-yl-methyl)-hydroxycarbonylmethylamino]-1,2,3,4-tetrahydro-quinoline-hydrochloride Prepared from the compound prepared according to Example 24(78)

Yield: 69% of theory, $C_{32}H_{32}N_4O_3 \times HCl \times H_2O$ (575.13)

| Calc.: | C | 66.82 | H | 6.13 | N | 9.74 |
|---|---|---|---|---|---|---|
| Found: | | 67.43 | | 6.75 | | 8.46 |

(20) 1-[3-(4-amidino-phenyl)-propionyl]-6-[N-(2-hydroxycarbonylethylcarbonyl)-benzylamino]-1,2,3,4-tetrahydro-quinoline-hydrochloride Prepared from the compound prepared according to Example 24(81)

Yield: 98% of theory, $C_{30}H_{32}N_4O_4 \times HCl \times H_2O$ (567.11)

| Calc.: | C | 63.53 | H | 6.22 | N | 9.87 |
|---|---|---|---|---|---|---|
| Found: | | 63.53 | | 6.38 | | 9.11 |

(21) 1-[3-(4-amidino-phenyl)-propionyl]-6-(N-hydroxy-carbonylmethyl-benzylamino)-1,2,3,4-tetrahydro-quinoline-hydrochloride
Prepared from the compound prepared according to Example 24(76)
Yield: 79% of theory,
$C_{28}H_{30}N_4O_3 \times HCl \times 1.5\ H_2O$ (534.07)

| Calc.: | C | 62.97 | H | 6.41 | N | 10.49 |
|---|---|---|---|---|---|---|
| Found: | | 63.17 | | 6.83 | | 8.67 |

(22) 1-[3-(4-amidino-phenyl)-propionyl]-6-[N-hydroxy-carbonylmethyl-N-(2,2-diphenyl-ethyl)-amino]-1,2,3,4-tetrahydro-quinoline-hydrochloride
Prepared from the compound prepared according to Example 24(92)
Yield: 90% of theory,
$C_{35}H_{36}N_4O_3 \times HCl$ (597.20)

| Calc.: | C | 69.79 | H | 6.04 | N | 8.46 |
|---|---|---|---|---|---|---|
| Found: | | 70.39 | | 6.24 | | 9.38 |

EXAMPLE 32

1-[3-(4-benzyloxycarbonylamidino-phenyl)-propionyl]-6-(1-naphthyl-sulphonamido)-1,2,3,4-tetrahydro-quinoline 15.5 g of 1-[3-(4-amidino-phenyl)propionyl]-6-(1-naphthyl-sulphonamido)-1,2,3,4-tetrahydro-quinoline-hydrochloride are dissolved in 250 ml of tetrahydrofuran and 25 ml of water and combined with 6.9 g of sodium carbonate. Then 5.8 g (0.032 mol) of benzyl chloroformate are added dropwise at ambient temperature over 30 minutes and the solution is stirred overnight. Then it is decanted from the precipitate, the solution is concentrated to about 50 ml by evaporation and extracted three times with ethyl acetate. The organic phase is dried, concentrated by rotary evaporation and the residue is filtered over a silica gel column with methylene chloride/ethyl acetate (7:3).
Yield: 14.0 g (77% of theory),
Melting point: 172–174° C.
The following are prepared analogously:
(1) 1-[3-(4-benzyloxycarbonylamidino-phenyl)-propionyl]-6-phenylsulphonylamino-1,2,3,4-tetrahydro-quinoline
Prepared from the compound prepared according to Example 22
Yield: 75% of theory,
Melting point: 172–174° C.
$C_{33}H_{32}N_4O_5S \times 0.5\ H_2O$ (605.72)

| Calc.: | C | 65.44 | H | 5.49 | N | 9.25 |
|---|---|---|---|---|---|---|
| Found: | | 65.58 | | 5.60 | | 8.93 |

(2) 1-[3-(4-methoxycarbonylamidino-phenyl)-propionyl]-6-[N-(quinoline-8-sulphonyl)-N-ethoxycarbonylmethyl-amino]-1,2,3,4-tetrahydro-quinoline (3) 1-[3-(4-octyloxycarbonylamidino-phenyl)-propionyl]-6-[N-(quinoline-8-sulphonyl)-N-ethoxycarbonylmethyl-amino]-1,2,3,4-tetrahydro-quinoline
(4) 1-[3-(4-hexyloxycarbonylamidino-phenyl)-propionyl]-6-phenylsulphonylamino-1,2,3,4-tetrahydro-quinoline
(5) 1-[3-(4-ethyloxycarbonylamidino-phenyl)-propionyl]-6-phenylsulphonylamino-1,2,3,4-tetrahydro-quinoline
(6) ethyl 1-[3-(4-heptyloxycarbonylamidino-phenyl)-propionyl]-6-[N-(naphth-1-yl-sulphonyl)-N-ethoxycarbonylmethyl-amino]-1,2,3,4-tetrahydro-quinoline-6-yl)-( )-amino]-acetate
(7) 1-[3-(4-ethyloxycarbonylamidino-phenyl)-propionyl]-6-[N-(naphth-1-yl-sulphonyl)-N-ethoxycarbonylmethyl-amino]-1,2,3,4-tetrahydro-quinoline
(8) 1-[3-(4-octyloxycarbonylamidino-phenyl)-propionyl]-6-(N-phenylsulphonyl-N-ethoxycarbonylmethyl-amino)-1,2,3,4-tetrahydro-quinoline
(9) 1-[3-(4-methyloxycarbonylamidino-phenyl)-propionyl]-6-(N-phenylsulphonyl-N-ethoxycarbonylmethyl-amino)-1,2,3,4-tetrahydro-quinoline
(10) 1-[3-(4-ethyloxycarbonylamidino-phenyl)-propionyl]-6-(N-benzoyl-N-ethoxycarbonylmethyl-amino)-1,2,3,4-tetrahydro-quinoline
(11) 1-[3-(4-Octyloxycarbonylamidino-phenyl)-propionyl]-6-(N-ethoxycarbonylmethyl-phenylamino)-1,2,3,4-tetrahydro-quinoline
(12) 1-[3-(4methyloxycarbonylamidino-phenyl)-propionyl]-6-(N-ethoxycarbonylmethyl-phenylamino)-1,2,3,4-tetrahydro-quinoline

EXAMPLE 33

Dry ampoule containing 75 mg of active substance per 10 ml
Composition

| Active substance | 75.0 mg |
|---|---|
| Mannitol | 50.0 mg |
| water for injections | ad 10.0 ml |

Preparation
Active substance and mannitol are dissolved in water. After packaging the solution is freeze-dried. To produce the solution ready for use, the product is dissolved in water for injections.

EXAMPLE 34

Dry ampoule containing 35 mg of active substance per 2 ml
Composition

| Active substance | 35.0 mg |
|---|---|
| Mannitol | 100.0 mg |
| water for injections | ad 2.0 ml |

Preparation
Active substance and mannitol are dissolved in water. After packaging, the solution is freeze-dried.
To produce the solution ready for use, the product is dissolved in water for injections.

EXAMPLE 35

Tablet containing 50 mg of active substance
Composition

| (1) Active substance | 50.0 mg |
|---|---|
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation (1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 9 mm.

EXAMPLE 36

Tablet containing 350 mg of active substance
Preparation

| (1) Active substance | 350.0 mg |
|---|---|
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

EXAMPLE 37

Capsules containing 50 mg of active substance
Composition

| (1) Active substance | 50.0 mg |
|---|---|
| (2) Dried maize starch | 58.0 mg |
| (3) Powdered lactos | 50.0 mg |
| (4) Magnesium stearate | 2.0 mg |
| | 160.0 mg |

Preparation (1) is triturated with (3). This trituration is added to the mixture of (2) and (4) with vigorous mixing.

This powder mixture is packed into size 3 hard gelatine capsules in a capsule filling machine.

EXAMPLE 38

Capsules containing 350 mg of active substance
Composition

| (1) Active substance | 350.0 mg |
|---|---|
| (2) Dried maize starch | 46.0 mg |
| (3) Powdered lactose | 30.0 mg |
| (4) Magnesium stearate | 4.0 mg |
| | 430.0 mg |

Preparation (1) is triturated with (3). This trituration is added to the mixture of (2) and (4) with vigorous mixing.

This powder mixture is packed into size 0 hard gelatine capsules in a capsule filling machine.

EXAMPLE 39

Suppositories containing 100 mg of active substance
1 suppository contains

| Active substance | 100.0 mg |
|---|---|
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

Method

The polyethyleneglycol is melted together with polyethylene sorbitan monostearate. At 40° C. the ground active substance is homogeneously dispersed in the melt. It is cooled to 38° C. and poured into slightly chilled suppository moulds.

What is claimed is:

1. A compound of the formula I

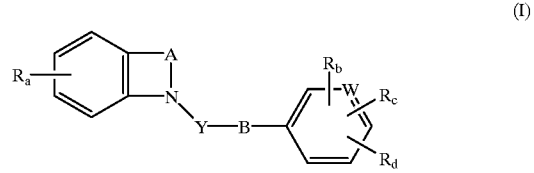

wherein:

$R_a$ is a hydrogen atom, a carboxy, $C_{1-3}$-alkoxycarbonyl, benzoyl, phenylsulphonyl, nitro, $R_1NR_2$, $R_1NR_2$—X—, or $(R_3X)NR_1$— group, wherein:

$R_1$ is a hydrogen atom, a $C_{1-5}$-alkyl group optionally substituted by a phenyl, carboxy, $C_{1-4}$-alkoxycarbonyl, or aminocarbonyl group, wherein the amino group of the aminocarbonyl group is optionally additionally mono- or disubstituted by $C_{1-4}$-alkyl, phenyl-$C_{1-3}$-alkyl, phenyl, carboxy-$C_{1-3}$-alkyl-, or $C_{1-3}$-alkoxycarbonyl-$C_{1-3}$-alkyl groups wherein the substituents are identical or different, or a straight-chained $C_{2-3}$-alkyl group terminally substituted by an amino, $C_{1-3}$-alkylamino, di-($C_{1-3}$-alkyl)amino, $C_{1-4}$-alkanoylamino, phenylamino, N-benzyloxycarbonyl-phenylamino, pyrrolidino, piperidino, or morpholino group, $R_2$ is a hydrogen atom, a $C_{1-3}$-alkyl group optionally substituted by one or two phenyl groups or by a naphthyl group, or a phenyl group optionally substituted by a fluorine, chlorine, or bromine atom or by a straight-chained $C_{2-3}$-alkyl group terminally substituted by an amino, $C_{1-3}$-alkylamino, $C_{1-3}$-alkanoylamino, di-($C_{1-3}$-alkyl)amino, pyrrolidino, piperidino, or morpholino group, or $R_1$ and $R_2$ together with the nitrogen atom between them are a pyrrolidino or piperidino group optionally substituted by a $C_{1-3}$-alkyl, carboxy, or $C_{1-3}$-alkoxycarbonyl group, a pyrrolidino or piperidino group substituted by two $C_{1-3}$-alkyl groups, or a morpholino group, $R_3$ is a straight-chained or branched $C_{1-7}$-alkyl group optionally substituted in the 1, 2, or 3 position by a phenyl group or in the 2 to 7 position by a fluorine, chlorine, or bromine atom, by a carboxy, or $C_{1-3}$-alkoxycarbonyl group, a trifluoromethyl group, a phenyl, naphthyl, or chromanyl group optionally substituted in each case by a fluorine, chlorine, or bromine atom, by a trifluoromethyl, $C_{1-3}$-alkyl, $C_{1-3}$-alkoxy, amino, $C_{1-3}$-alkylamino, di-($C_{1-3}$-alkyl) amino, or aminocarbonyl group, wherein the above-mentioned phenyl, naphthyl, or chromanyl groups are optionally additionally substituted by one to three methyl groups, a phenyl or aminophenyl group substituted by two chlorine or bromine atoms, a thienyl group optionally substituted by a chlorine or bromine atom or by a methyl group, a $C_{3-8}$-cycloalkyl, $C_{8-12}$-bicycloalkanone, quinolyl, isoquinolyl, or benzimidazolyl group, or $R_1$ and $R_3$ together are an n-alkylene group with 3 to 5 carbon atoms, wherein an ethylene group linked to the $SO_2$— or CO— group is optionally replaced by a 1,2-phenylene group, and X is a carbonyl or sulphonyl group, or $R_a$ is a $C_{2-3}$-alkanoyl group substituted in the alkyl moiety by a carboxy-$C_{1-3}$-alkyl or $C_{1-3}$-alkoxycarbonyl-$C_{1-3}$-alkyl group and a benzoyl, naphthoyl, phenylsulphonyl, or naphthylsulphonyl group;

$R_b$ is an amidino group optionally substituted by a $C_{1-10}$-alkoxycarbonyl or phenyl-$C_{1-3}$-alkoxycarbonyl group, or a cyano or aminomethyl group, $R_c$ and $R_d$, which are identical or different, are each a hydrogen, fluorine, chlorine, bromine, or iodine atom, a methyl, methoxy, nitro, amino, or aminocarbonyl group, or an amino group optionally substituted by a straight-chained $C_{2-4}$-alkanoyl group, wherein the alkanoyl moiety is optionally terminally substituted by a carboxy or $C_{1-3}$-alkoxycarbonyl group, A is an n-propylene group optionally substituted by one or two $C_{1-3}$-alkyl groups, wherein in the n-propylene group of A,
  a methylene group, if linked to the nitrogen atom, is optionally replaced by a carbonyl group, or
  a methylene group, if linked to the phenyl nucleus, is optionally replaced by an oxygen or sulfur atom, by a sulphinyl or sulphonyl group, or by an imino group optionally substituted by a $C_{1-3}$-alkyl group, B is a bond, or a methylene, ethylene, ethenylene or n-propylene group optionally substituted by one or two $C_{1-3}$-alkyl groups, wherein
  in the methylene, ethylene, or n-propylene group of B, if Y is a carbonyl or thiocarbonyl group, a methylene group is optionally replaced by an oxygen atom or by an imino group optionally substituted by a $C_{1-3}$-alkyl group, or
  in the ethylene or n-propylene group of B, if Y is a methylene group, a methylene group in the 3 or 4 position relative to the nitrogen atom is optionally replaced by an oxygen atom or by an imino group optionally substituted by a $C_{1-3}$-alkyl group;

W is a methane group or a nitrogen atom; and

Y is a methylene, carbonyl; or thiocarbonyl group, or a tautomer or a pharmaceutically acceptable salt thereof.

2. The compound of the formula I according to claim 1, wherein:

$R_b$ is an amidino group optionally substituted by a $C_{1-10}$-alkoxycarbonyl or phenyl-$C_{1-3}$-alkoxycarbonyl group, or a pharmaceutically acceptable salt thereof.

3. The compound of the formula I according to claim 1, wherein:

$R_a$ is an $R_1NR_2$, $R_1'NR_2'$—X, or $(R_3X)NR_1$— group, wherein:

$R_1$ is a hydrogen atom, a $C_{1-4}$-alkyl group optionally substituted by a phenyl, carboxy, $C_{1-2}$-alkoxycarbonyl, or aminocarbonyl group, wherein the amino group of the aminocarbonyl group is optionally additionally mono- or disubstituted by $C_{1-4}$-alkyl, phenyl, benzyl, carboxy-$C_{1-2}$-alkyl, or $C_{1-2}$-alkoxycarbonyl-$C_{1-2}$-alkyl groups and wherein the substituents are identical or different, or an ethyl group terminally substituted by an amino, acetylamino, morpholino, phenylamino, or N-benzyloxycarbonyl-phenylamino group, $R_2$ is a hydrogen atom, a $C_{1-3}$-alkyl group optionally substituted by one or two phenyl groups or by a naphthyl group, a cyclohexyl group, or a phenyl group optionally substituted by a chlorine atom or by a 2-aminoethyl or 2-acetylamino group, $R_1'$ and $R_2'$ have the meanings given hereinbefore for $R_1$ and $R_2$ or together with the nitrogen atom between them are a pyrrolidino or piperidino group optionally substituted by a methyl, carboxy, or $C_{1-2}$-alkoxycarbonyl group, a pyrrolidino or piperidino group substituted by two methyl groups, or a morpholino group, $R_3$ is a straight-chained or branched $C_{1-5}$-alkyl group optionally substituted in the 1, 2, or 3 position by a phenyl, carboxy, or $C_{1-3}$-alkoxycarbonyl group or in the 2 or 3 position by a chlorine atom, a trifluoromethyl group, a phenyl, or naphthyl group, optionally substituted in each case by a fluorine, chlorine, or bromine atom, by a trifluoromethyl, $C_{1-3}$-alkyl, $C_{1-3}$-alkoxy, amino, $C_{1-3}$-alkylamino, di-($C_{1-3}$-alkyl) amino, or aminocarbonyl group, wherein the above-mentioned phenyl groups are optionally additionally substituted by one to three methyl groups, a phenyl or aminophenyl group substituted by two chlorine or bromine atoms, a thienyl group substituted by a chlorine or bromine atom, a $C_{3-7}$-cycloalkyl, quinolyl, isoquinolyl, or benzimidazolyl group, or $R_1$ and $R_3$ together are an n-alkylene group with 3 to 5 carbon atoms, wherein an ethylene group linked to the $SO_2$ or CO— group is optionally replaced by a 1,2-phenylene group, and X is a carbonyl or sulphonyl group, or $R_a$ also is a $C_{2-3}$-alkanoyl group substituted in the alkyl moiety by a carboxy-$C_{1-3}$-alkyl or $C_{1-3}$-alkoxycarbonyl-$C_{1-3}$-alkyl group and a benzoyl, naphthoyl, phenylsulphonyl, or naphthylsulphonyl group;

$R_b$ is an amidino group optionally substituted by a $C_{1-10}$-alkoxycarbonyl or phenyl-$C_{1-3}$-alkoxycarbonyl group;

$R_c$ is a hydrogen, fluorine, chlorine, bromine, or iodine atom, a methyl, methoxy, aminocarbonyl, amino, or nitro group, or an amino group optionally substituted by a straight-chained $C_{2-4}$-alkanoyl group, wherein the alkanoyl moiety is optionally terminally substituted by a carboxy or $C_{1-3}$-alkoxycarbonyl group;

$R_d$ is a hydrogen atom;

A is an n-propylene group optionally substituted by one or two methyl groups, wherein in the n-propylene group of A, a methylene group, if linked to the nitrogen atom, is optionally replaced by a carbonyl group;

B is a bond, or a methylene, ethylene, ethenylene, or n-propylene group optionally substituted by one or two methyl groups, wherein
in the methylene, ethylene, or n-propylene group of B, if Y is a carbonyl or thiocarbonyl group, a methylene group is optionally replaced by an oxygen atom or by an imino group optionally substituted by a methyl group, or
in the ethylene or n-propylene group of B, if Y is a methylene group, a methylene group in the 3 or 4 position relative to the nitrogen atom is optionally replaced by an oxygen atom or by an imino group optionally substituted by a methyl group;

W is a methine group; and

Y is a methylene, carbonyl, or thiocarbonyl group, or a pharmaceutically acceptable salt thereof.

4. The compound of the formula I according to claim 1, wherein:

$R_a$ is a $(R_3SO_2)NR_1$— group, or the optical antipode, or the pharmaceutically acceptable salt thereof.

5. The compound of formula I according to claim 1, wherein:

$R_a$ is a $(R_3SO_2)NR_1$— group, wherein $R_1$ and $R_3$ are defined as in claim 4;

$R_b$ is an amidino group optionally substituted by a $C_{1-10}$-alkoxycarbonyl or phenyl-$C_{1-3}$-alkoxycarbonyl group;

$R_c$ and $R_d$ are each a hydrogen atom;

A is an n-propylene group optionally substituted by a methyl group;

B is an ethylene group;

W is a methine group; and

Y is a carbonyl group, or a pharmaceutically acceptable salt thereof.

6. A compound selected from the group consisting of:
(a) 1-[3-(4-amidino-phenyl)propionyl]-6-(4-fluoro-phenylsulphonamido)-1,2,3,4-tetrahydro-quinoline,
(b) 1-[3-(4-amidino-phenyl)propionyl]-6-butylsulphonamido-1,2,3,4-tetrahydro-quinoline,
(c) 1-[3-(4-amidino-phenyl)propionyl]-5-phenylsulphonamido-1,2,3,4-tetrahydro-quinoline,
(d) 1-[3-(4-amidino-phenyl)propionyl]-3-methyl-6-phenylsulphonamido-1,2,3,4-tetrahydro-quinoline,
(e) 1-[3-(4-amidino-phenyl)propionyl]-6-(5-chloro-thien-2-ylsulphonamido)-1,2,3,4-tetrahydro-quinoline,
(f) 1-[3-(4-amidino-phenyl)propionyl]-6-phenylsulphonamido-1,2,3,4-tetrahydro-quinoline,
(g) 1-[3-(4-amidino-phenyl)propionyl]-6-(N-methyl-phenylsulphonamido)-1,2,3,4-tetrahydro-quinoline,
(h) 1-[3-(4-amidino-phenyl)propionyl]-6-(N-ethoxycarbonyl-methyl-phenysulphonamido)-1,2,3,4-tetrahydro-quinoline,
(i) 1-[3-(4-amidino-phenyl)propionyl]-6-(N-carboxymethyl-phenylsulphonamido)-1,2,3,4-tetrahydro-quinoline,
(j) 1-[3-(4-aminomethyl-phenyl)propionyl]-6-phenylsulphonamido-1,2,3,4-tetrahydro-quinoline,
(k) 1-[3-(4-amidino-phenyl)propyl]-6-phenylsulphonamido-1,2,3,4-tetrahydro-quinoline,
(l) 1-[3-(4methyloxycarbonyl-amidino-phenyl)propionyl]-6-phenylsulphonamido-1,2,3,4-tetrahydro-quinoline,
(m) 1-[3-(4-amidino-phenyl)-propionyl]-6-(N-phenyl-methyl-aminocarbony)-1,2,3,4-tetrahydro-quinoline,
(n) 1-[(4-amidino-phenoxy)-acetyl]-6-[N-(1-naphthylsulphonyl)-hydroxycarbonylmethylamino]-1,2,3,4-tetrahydro-quinoline,
(o) 1-[3-(4-amidino-phenyl)-propionyl]-6-diethylaminocarbonyl-1,2,3,4-tetrahydro-quinoline,
(p) 1-[3-(4-amidino-phenyl)-propionyl]-6-(N-benzoyl-methylamino)-1,2,3,4-tetrahydro-quinoline,
(q) 1-[3-(4-amidino-phenyl)-propionyl]-6-(N-benzoyl-methylamino)-1,2,3,4-tetrahydro-quinoline,
(r) 1-[3-(4-amidino-phenyl)-propionyl]-6-[N-(naphth-1-yl-sulphonyl)-hydroxycarbonylmethylamino]-1,2,3,4-tetrahydro-quinoline,
(s) 1-[3-(4-amidino-phenyl)-propionyl]-6-[N-(1-naphthoyl)-hydroxycarbonylmethylamino]-1,2,3,4-tetrahydro-quinoline,
(t) 1-[3-(4-amidino-phenyl)-propionyl]-6-(N-benzoyl-hydroxycarbonylmethylamino]-1,2,3,4-tetrahydro-quinoline,
(u) 1-[3-(4-amidino-phenyl)-propionyl]-6-[N-(quinoline-8-sulphonyl)-hydroxycarbonylmethylamino]-1,2,3,4-tetrahydro-quinoline and
(v) 1-[3-(4-amidino-phenyl)-propionyl]-6-[N-(n-butylsulphonyl)-hydroxycarbonylmethylamino]-1,2,3,4-tetrahydro-quinoline, or a pharmaceutically acceptable salt thereof.

7. A pharmaceutically acceptable salt of a compound of the formula I, in accordance with one of claims 1, 2, 3, 4, 5, or 6.

8. A pharmaceutical composition comprising a compound of the formula I in accordance with one of claims 1, 2, 3, 4, 5 or 6, wherein $R_b$ is not cyano, or a pharmaceutically acceptable salt thereof, and a pharmaceutically acceptable carrier.

9. A method for treating or inhibiting thrombus formation which comprises administering to a host in need thereof an antithrombotic amount of a compound of the formula I, in accordance with one of claims 1, 2, 3, 4, 5 or 6, wherein $R_b$ is not cyano, or a pharmaceutically acceptable salt thereof.

10. A method for treating a fibrin-dependent inflammatory condition which comprises administering to a host in need thereof a therapeutic amount of a compound of the formula I, in accordance with one of claims 1, 2, 3, 4, 5 or 6, wherein $R_b$ is not cyano, or a pharmaceutically acceptable salt thereof.

* * * * *

UNITED STATES PATENT AND TRADEMARK OFFICE
CERTIFICATE OF CORRECTION

PATENT NO.    : 6,300,342 B1
DATED         : October 9, 2001
INVENTOR(S)   : Armin Heckel, Rainer Soyka, Wolfgang Grell, Eric Haaksma, Klaus Binder and Rainer Zimmerman Page 1 of 1

It is certified that error appears in the above-identified patent and that said Letters Patent is hereby corrected as shown below:

Title page,
Assignee, shown as "Boehringer Ingelheim Pharm KG" should read -- Boehringer Ingelheim Pharma KG".

Column 4,
Line 14, "sub-stituted" should read -- substituted --.

Column 14,
Line 13, "di-o-to-lyltartaric" should read -- di-o-tolyltartaric --.

Column 35,
Line 1, "me-thylene" should read -- methylene --.

Column 50,
Line 22, "hydrochlorid" should read -- hydrochloride --.

Column 60,
Line 43, "acetate/methylene" should read -- acetate methylene --

Column 69,
Line 47, "lactos" should read -- lactose --

Signed and Sealed this

Ninth Day of April, 2002

Attest:

Attesting Officer

JAMES E. ROGAN
Director of the United States Patent and Trademark Office